United States Patent
Smith et al.

(10) Patent No.: US 12,133,867 B2
(45) Date of Patent: *Nov. 5, 2024

(54) UNIVERSAL ANTI-CD22 CHIMERIC ANTIGEN RECEPTOR ENGINEERED IMMUNE CELLS

(71) Applicant: CELLECTIS SA, Paris (FR)

(72) Inventors: Julianne Smith, New York, NY (US); Phillippe Duchateau, Draveil (FR); Murielle Derrien, Paris (FR)

(73) Assignee: CELLECTIS SA, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/393,322

(22) Filed: Dec. 21, 2023

(65) Prior Publication Data

US 2024/0189354 A1 Jun. 13, 2024

Related U.S. Application Data

(63) Continuation of application No. 16/498,899, filed as application No. PCT/EP2018/058367 on Mar. 30, 2018, now Pat. No. 11,944,643.

(30) Foreign Application Priority Data

| Mar. 31, 2017 | (DK) | 201770239 |
|---|---|---|
| Mar. 31, 2017 | (DK) | 201770240 |
| Jun. 30, 2017 | (DK) | 201770542 |

(51) Int. Cl.

| A61K 35/17 | (2015.01) |
|---|---|
| A61K 31/365 | (2006.01) |
| A61K 39/395 | (2006.01) |
| A61P 35/02 | (2006.01) |
| C07K 14/705 | (2006.01) |
| C07K 14/725 | (2006.01) |
| C07K 16/28 | (2006.01) |

(52) U.S. Cl.
CPC ............ *A61K 35/17* (2013.01); *A61K 31/365* (2013.01); *A61K 39/39558* (2013.01); *A61P 35/02* (2018.01); *C07K 14/7051* (2013.01); *C07K 14/70517* (2013.01); *C07K 14/70578* (2013.01); *C07K 16/2803* (2013.01); *C07K 2317/34* (2013.01); *C07K 2317/53* (2013.01); *C07K 2317/622* (2013.01)

(58) Field of Classification Search
CPC . A61K 35/17; A61K 2239/10; A61K 2239/23
USPC ...................................................... 424/133.1
See application file for complete search history.

(56) References Cited

U.S. PATENT DOCUMENTS

| 4,683,195 A | 7/1987 | Mullis et al. |
|---|---|---|
| 5,037,743 A | 8/1991 | Welch et al. |
| 5,143,830 A | 9/1992 | Holland et al. |
| 5,858,358 A | 1/1999 | June et al. |
| 5,883,223 A | 3/1999 | Gray |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 9,334,331 B2 | 5/2016 | Igawa et al. |
| 10,421,807 B2 | 9/2019 | Gonzales et al. |
| 11,690,873 B2 * | 7/2023 | Schiffer-Mannioui ............ A61P 35/02 424/93.71 |
| 11,944,643 B2 * | 4/2024 | Smith .................. A61K 31/365 |
| 2006/0121005 A1 | 6/2006 | Berenson et al. |
| 2021/0100839 A1 | 4/2021 | Schiffer-Mannioui et al. |
| 2022/0233588 A1 | 7/2022 | Sourdive et al. |
| 2023/0248825 A1 * | 8/2023 | Das ................ A61K 39/464419 424/93.21 |

FOREIGN PATENT DOCUMENTS

| CN | 105958210 A | 9/2016 |
|---|---|---|
| WO | WO-2014065961 A1 | 5/2014 |
| WO | WO-2015092024 A2 | 6/2015 |
| WO | WO-2016120216 A1 | 8/2016 |
| WO | WO-2018178377 A1 | 10/2018 |

OTHER PUBLICATIONS

Clinical trial.gov NCT04150497; pp. 1-6, Apr. 5, 2024.*
Hu et al.(Clin Cancer Res May 15, 2021;27(10):2764-2772; Epub Feb. 24, 2021.*
Edwards et al.: The remarkable flexibility of the human antibody repertoire; isolation of over one thousand different antibodies to a single protein, BLyS. J. Mol. Biol. 334(1):103-118 (2003).
Eyquem et al.: Targeting a CAR to the TRAC locus with CRISPR/Cas9 enhances tumour rejection. Nature. 543(7643):113-117 (2017).
Goel et al.: Plasticity within the Antigen-Combining Site May Manifest as Molecular Mimicry in the Humoral Immune Response. J. Immunol. 173:7358-7367 (2004).

(Continued)

*Primary Examiner* — Lynn A Bristol
(74) *Attorney, Agent, or Firm* — Wilson Sonsini Goodrich & Rosati

(57) ABSTRACT

The present invention relates to an engineered immune cell endowed with CD22 Chimeric Antigen Receptors (CD22 CAR) with a deletion in the TRAC gene that is able to redirect immune cell specificity and reactivity toward selected tumor cells. The engineered immune cells endowed with such CARs are particularly suited for treating relapsed refractory CD22 expressing cancers.

24 Claims, 9 Drawing Sheets
Specification includes a Sequence Listing.

(56) References Cited

OTHER PUBLICATIONS

Gouble et al.: UCART22:allogenic adoptive immunotherapy of leukemia by targeting CD22 with CAT T-cells. Cancer Res. 77(13):3763 (2017).
Haso et al.: Anti-CD22-chimeric antigen receptors targeting B-cell precursor acute lymphoblastic leukemia. Blood. 121(7):1165-1174 (2013).
Khan et al.: J. Immunol. 192:5398-5404 (2014).
Lloyd et al., "Modelling the Human Immune Response: Performance of a 10" Human Antibody Repertoire Against a Broad Panel of Therapeutically Relevant Antigens," Protein Engineering Design & Selection 22(3):159-168 (2009) (Published online Oct. 29, 2008).
Long et al.: Lessons learned from a highly-active CD22-specific chimeric antigen receptor. Oncoimmunology. 2(4):e23621 (2013).
PCT/EP2018/058367 International Search Report and Written Opinion dated Jul. 16, 2018.
Philip et al.: A highly compact epitope-based marker/suicide gene for easier and safer T-cell therapy. Blood. 124(8):1277-1287 (2014).
Poosarla et al.: Computational de novo design of antibodies binding to a peptide with high affinity. Biotechn. Bioeng. 114(6):1331-1342 (2017).
Qaraghuli et al.: Antibody-protein binding and conformational changes: identifying allosteric signalling pathways to engineer a better effector response. Nature Scientific Reports. 10(1):13969 pp. 1-10 (2020).
Wells et al.: Pre-Clinical Activity of Allogeneic Anti-CD22 CAR-T Cells for the Treatment of B-Cell Acute Lymphoblastic Leukemia. ASH Atlanta XP002781137 (2017).
Wells et al.: Pre-clinical Activity of Allogeneic Anti-CD22 CAR-T Cells for the Treatment of B-Cell Acute Lymphoblastic Leukemia. Blood. American Society of Hemotology. 130(1):808 (2017).
Brentjens et al. CD19-targeted T cells rapidly induce molecular remissions in adults with chemotherapy-refractory acute lymphoblastic leukemia. Sci Transl Med. Mar. 2, 20130;5(177):177ra38. 9 pages.
Faderl et al.: Augmented hyper-CVAD based on dose-intensified vincristine, dexamethasone, and asparaginase in adult acute lymphoblastic leukemia salvage therapy. Clin Lymphoma Myeloma Leuk. 11(1):54-59 (2011).
Fielding, et al., Outcome of 609 adults after relapse of acute lymphoblastic leukemia (ALL); an MRC UKALL12/ECOG 2993 study. Blood 109(3):944-951 (2007).
Greenlee et al.: Cancer Statistics, 2000. CA Cancer J. Clin. 50:7-33 (2000).
Grupp et al. Chimeric antigen receptor-modified T cells for acute lymphoid leukemia. NEJM 368:1509-1518 (2013).
Ho et al.: Isolation of anti-CD22 Fv with high affinity by Fv display on human cells. PNAS. 103(25):9637-9642 (2006).
Inaba et al.: Acute lymphoblastic leukaemia. Lancet. 381(9881):1943-1955 (2013).
Juillerat et al.: An oxygen sensitive self-decision making engineered CAR T-cell. Sci. Rep. 7:39833 (2017).
Kebriaei et al. Phase I trials using Sleeping Beauty to generate CD19-specific Car T cells. J Clin Invest 126(9):3363-3376 (2016).
Kochenderfer et al., Chemotherapy-refractory diffuse large B-cell lymphoma and indolent B-cell malignancies can be effectively treated with autologous T cells expressing an anti-CD19 chimeric antigen receptor, Journal of Clinical Oncology 33(6):540-549 (Feb. 20, 2015).
Kuhn et al.: Inducible gene targeting in mice. Science. vol. 269(5229):1427-1429 (1995).
Lee et al. T cells expressing CD19 chimeric antigen receptors for acute lymphoblastic leukaemia in children and young adults: A phase 1 dose-escalation trial. The Lancet 385(9967):517-528 (2014).
Macleod et al., Integration of a CD19 Car into the TCR Alpha Chain Locus Streamlines Production of Allogeneic Gene-Edited Car T Cells, Molecular Therapy, vol. 25, No. 4, pp. 949-961, Apr. 2017.
Maude et al. CD19-targeted chimeric antigen receptor T-cell therapy for acute lymphoblastic leukemia. Blood 125(26):4017-4024 (2015).
Mullighan CG: Genome sequencing of lymphoid malignancies. Blood. 122(24):3899-3907 (2013).
Mullighan CG: Genomic characterization of childhood acute lymphoblastic leukemia. Semin Hematol. 50(4):314-324 (2013).
Kochenderfer et al., Eradication of B-lineage cells and regression of lymphoma in a patient treated with autologous T cells genetically engineered to recognize CD19 (Blood, 2010, 116:4099-4102) (Year: 2010).
Oriol et al.: Outcome after relapse of acute lymphoblastic leukemia in adult patients included in four consecutive risk-adapted trials by the PETHEMA Study Group. Haematologica. 95(4):589-596 (2010).
Park et al., CD19-targeted CAR T-cell therapeutics for hematologic malignancies: interpreting clinical outcomes to date, Blood. 2016; 127(26):3312-3320.
Porter et al. Chimeric antigen receptor-modified T cells in chronic lymphoid leukemia. NEJM 365:725-733 (2011).
Tavernier et al.: Outcome of treatment after first relapse in adults with acute lymphoblastic leukemia initially treated by the LALA-94 trial. Leukemia : official journal of the Leukemia Society of America. Leukemia Research Fund, U.K. 21(9):1907-1914 (2007).
Valton et al.: A Multidrug-resistant Engineered Car T Cell for Allogeneic Combination Immunotherapy. Mol Ther. 23(9):1507-1518. doi:10.1038/mt.2015.104 (2015).
Xiao et al.: Identification and characterization of fully human anti-CD22 monoclonal antibodies. mAbs 1:297-303 (2009).

\* cited by examiner

Single chain anti-CD22 and/or CD19 CAR

CD22 scfv  CD19 scfv
Or CD19 scfv  CD22 scfv

Multi-chain anti-CD22 or -22/19 CAR

UNIVERSAL ANTI-CD22 CHIMERIC ANTIGEN RECEPTOR ENGINEERED IMMUNE CELLS

CROSS REFERENCE TO RELATED APPLICATIONS

This application is a continuation application of U.S. application Ser. No. 16/498,899, filed Sep. 27, 2019, which is a national phase application under 35 U.S.C. § 371 of PCT International Application No. PCT/EP2018/058367, filed Mar. 30, 2018, which claims priority to PCT International Application No. PCT/EP2017/076800, filed Oct. 19, 2017, Danish Application No. PA201770542, filed Jun. 30, 2017, Danish Application No. PA201770240, filed Mar. 31, 2017, and Danish Application No. PA201770239, filed Mar. 31, 2017, each of which is hereby incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 103,441 Bytes (XML) file named "2024-04-17-_66524-702.301_SL," created on Apr. 17, 2024.

FIELD OF THE INVENTION

The present invention generally relates to the field of immunotherapy, and more specifically to Universal chimeric antigen receptor T cells specific for CD22 (UCART22) that are engineered human primary immune cells comprising at least one edited gene, preferably a gene coding a TCR subunit or a CD52 gene, and a Chimeric Antigen Receptors (CAR) specific for the cluster of differentiation 22 (CD22), (CAR CD22), and to methods for engineering said cells. The invention further relates to UCART22 for their use in patients who may or may not be the initial donor of cells ("allogenic" or "autologous" CD22 CAR engineered primary human immune cells) as a treatment for relapse refractory hematological cancers. The cells expressing a CD22 according to the invention are particularly efficient and safe for immunotherapy in particular against aggressive or relapsed cancer.

BACKGROUND OF THE INVENTION

More than 45,000 deaths were expected from hematological cancer (non-Hodgkin's lymphoma, leukemia) in the United States in 2000 (Greenlee et al., CA Cancer J. Clin., 50:7-33 (2000)). The numbers published in 2014 were similar and despite advances in treatments such as chemotherapy, the prognosis for such cancers remains basically unchanged. (E. K. Mai, U. Bertsch, J. Drig, C. Kunz, M. Haenel, I. W. Blau, M. Munder, A. Jauch, B. Schurich, T. Hielscher, M. Merz, B. Huegle-Doerr, A. Seckinger, D. Hose, J. Hillengass, M. S. Raab, K. Neben, H-W Lindemann, M. Zeis, C. Gerecke, I. G. H. Schmidt-Wolf, K. Weisel, C. Scheid, H. Salwender and H. Goldschmidt. Phase III trial of bortezomib, cyclophosphamide and dexamethasone (VCD) versus bortezomib, doxorubicin and dexamethasone (PAd) in newly diagnosed myeloma. *Leukemia* (19 Mar. 2015) doi:10.1038/leu.2015.80.

Unique among the new investigational treatments for these hematologic cancers is the genetic modification of cells with cytolytic capacity such as T cells through the gene-transfer of a chimeric antigen receptor (CAR) (Jena, Dotti et al., 2010).

CARs are synthetic receptors consisting of a targeting moiety that is associated with one or more signaling intracellular domains in a single molecule or in multiple transmembrane domains forming a multimer. In particular CAR, the binding moiety consists of an antigen-binding domain from a single-chain antibody (scFv), comprising the variable fragments of a monoclonal antibody joined by a linker. Binding moieties based on receptor or ligand domains have also been used successfully to prepare a CAR.

Signaling domains from co-stimulatory molecules of the T cell receptor (TCR), as well as particular transmembrane and hinge domains have been added to form CARs of second and third generations, leading to successful therapeutic trials in humans. In these studies, T-cells from a patient suffering a hematological ("liquid") cancer were redirected against malignant cells expressing for example CD19 or CD22 (June et al., 2011, Haso et al., 2013) and reinjected into the same patient. (Haso W, Lee D W, Shah N N, Stetler-Stevenson M, Yuan C M, Pastan I H, Dimitrov D S, Morgan R A, FitzGerald DJ, Barrett D M, Wayne A S, Mackall C L, Orentas R J. Anti-CD22-chimeric antigen receptors targeting B-cell precursor acute lymphoblastic leukemia. *Blood*. 2013 Feb. 14; 121(7):1165-74. doi: 10.1182/blood-2012-06-438002. Epub 2012 Dec. 14).

Methods allowing immune cells from one individual to be engineered before reinjection to the same individual—usually suffering from a cancer—are not well adapted in particular for aggressive forms of cancers that may be a race against time. Moreover, such method may be problematic or uncertain in patient whose immune system is altered.

To palliate this problem, immunotherapy using CAR-expressing so called "allogeneic" T cells (also called universal or "off the shelf" T cells) was recently implemented and the two first patients treated with such cells are still in remission about two years after treatment.

Nevertheless, there are still aspects of such therapy that may be improved, such as efficiency in the presence of anti-T cell drugs, efficiency against escaping cancer cells, persistence, means of control, etc. Indeed, it seems that cancer cells—by downregulating the expression of surface antigen recognized by CARs, may escape the treatment and subsist, despite the persistence of redirected immune in treated patients. Further, one the primary adverse, and sometimes lethal, effect observed in patients treated either with autologous or allogeneic T cells, is the cytokine release syndrome.

Thus, there is still a need for developing efficient and safe treatments for these pathologies, in particular for their aggressive or refractory/relapsed forms of hematological cancers.

BRIEF SUMMARY OF THE INVENTION

Here, the inventors have developed a new efficient treatment ("UCART22") comprising engineered primary human T cell with at least a deletion of the TRAC gene, endowed with a chimeric antigen receptor targeting CD22 and a safety marker allowing the number of said cells to be controlled in vivo and consequently the activity of said cells. In the new efficient treatment ("UCART22") comprising engineered primary human T cell with at least a deletion of the TRAC gene, at least one additional deletion in CD52, dCK, or J2 Microglobulin gene is contemplated.

These new UCART22 are particularly efficient for adoptive transfer in a patient suffering a CD22 mediated pathology, whether or not said patient is the initial donor of immune cells and whether or not said patient is already under therapy that affects immunity.

UCART22 cells of the invention are resistant to at least one chemical or antibody drug usually used to treat CD22-mediated pathology, such as CAMPATH® and/or Purine nucleotide analogs (PNAs). UCART22 cells of the invention can survive and be active in the presence of said drug used at a dose that kills more than 80% of the cells.

Significant and unexpected clinical advantages of the engineered isolated primary immune cells UCART22 are observed, including low cytokine release, no or very mild graft versus host disease and still a significant activity against the refractory relapsed forms of hematological cancer cells.

Other advantages will be disclosed in this study. This study which provides:

1. An engineered human T Cell Receptor Knock Out (TCR KO) cell endowed with a Chimeric Antigen Receptor (CAR) specific for CD22 (UCART22), a safety switch, preferably expressed at the cell surface, said anti-CD22 CAR (CD22 CAR) comprising:
   i) at least one extracellular domain comprising:
      a hinge domain from CD8alpha, and
      an antigen binding domain specific for CD22, optionally a leader sequence,
   ii) a transmembrane domain from CD8alpha, and
   iii) an intracellular signaling domain said CD22 CAR having a polypeptide sequence with at least 80% identity with SEQ ID NO: 15, said safety switch comprising:
      a RQR8 temporarily linked to the CD22 CAR by a peptide 2A, or
      at least two rituximab mAb-specific epitopes, preferably located between the VH and the Hinge domain, or 3 rituximab mAb-specific epitopes or 3 rituximab mAb-specific epitopes and a QBEND-10 mAb-specific epitopes linked to the CD22 CAR.

2. The UCART22 of embodiment 1 wherein a polynucleotide sequence having at least 80% identity with SEQ ID SEQ ID NO: 11 is inserted into the genome, and further comprising an inactivated TRAC gene with an insertion, a deletion or a mutation within SEQ ID NO: 18, with
   undetectable level of T Cell Receptor (TCR) at the cell surface as measured by flow cytometry, and undetectable level of off-site events as measured by guide sequence technique.

The UCART22 according to 2 wherein said anti-CD22 CAR is inserted preferably into the TRAC gene, preferably with SEQ ID NO: 18.

3. The UCART22 according to any one of embodiment 1 to 2 comprising another inactivated gene selected from dCK gene, B2M gene, CD52 gene, preferably CD52 gene.

The UCART22 according to any one of embodiment 1 to 3 wherein and at least one additional gene is inactivated, said gene is selected from a gene encoding aryl hydrocarbon receptor (AHR), Transforming growth factor beta receptor) (TGF beta receptor), Interleukin 10 receptor (IL-10 R), Programmed cell death protein 1, a combination thereof.

The UCART22 according to any one of embodiment 1 to 4 wherein a gene encoding β₂ Microglobulin (B2M), is inactivated.

The UCART22 according to any one of embodiment 1 to 5 wherein a gene encoding aryl hydrocarbon receptor (AHR), is inactivated.

The UCART22 according to any one of embodiment 1 to 6 wherein a gene encoding
Transforming growth factor beta receptor) (TGF beta receptor), is inactivated.

8. The UCART22 according to any one of embodiment 1 to 7 wherein a gene encoding Interleukin 10 receptor (IL-10 R), is inactivated.

9. The UCART22 according to any one of embodiment 1 to 8 wherein a gene encoding Programmed cell death protein 1 (PD1), is inactivated.

5. The UCART22 according to any one of embodiment 1 to 4 comprising an additional scFv specific for any one of the following tumor-associated surface antigens selected from CD19, CD20, CD30, a major histocompatibility complex (MHC) molecule, an Immunoglobulin (Ig), CD3, CD5, CD34, CD79, preferably CD79b, CD138, B7-1 (CD80), BCMA (CD269, TNFRSF 17), FLT-3, or PAX5, preferably CD19.

6. The UCART22 according to any one of embodiment 1 to 5 wherein said CD22CAR further comprises an antigen binding domain specific for CD19 or wherein said UCART22 further comprises a CD19CAR, preferably a CD19 CAR having at least 80% identity with SEQ ID N° 25 or a SEQ ID NO: 26.

7. The UCART22 according to any one of embodiment 1 to 5 wherein the anti-CD22 CAR is a single-chain CAR or a multi-chain CAR.

8. The UCART22 according to any one of embodiment 5 or 6 wherein the anti-CD19 CAR is a single-chain CAR or a multi-chain CAR.

The UCART22 according to any one of the above wherein the anti-CD22 CAR is a single-chain CAR comprising an additional scFv specific for CD19.

The UCART22 according to any one of the above wherein the anti-CD22 CAR is a single-chain CAR comprising an additional scFv specific for CD20.

The UCART22 according to any one of the above wherein the anti-CD22 CAR is a single-chain CAR comprising an additional scFv specific for CD30.

The UCART22 according to any one of the above wherein the anti-CD22 CAR is a single-chain CAR comprising an additional scFv specific for a major histocompatibility complex (MHC) molecule.

The UCART22 according to any one of the above wherein the anti-CD22 CAR is a single-chain CAR comprising an additional scFv specific for an Immunoglobulin (Ig).

The UCART22 according to any one of the above wherein the anti-CD22 CAR is a single-chain CAR comprising an additional scFv specific for CD3.

The UCART22 according to any one of the above wherein the anti-CD22 CAR is a single-chain CAR comprising an additional scFv specific for CD5.

The UCART22 according to any one of the above wherein the anti-CD22 CAR is a single-chain CAR comprising an additional scFv specific for CD34.

The UCART22 according to any one of the above wherein the anti-CD22 CAR is a single-chain CAR comprising an additional scFv specific for CD79, preferably CD79b.

The UCART22 according to any one of the above wherein the anti-CD22 CAR is a single-chain CAR comprising an additional scFv specific for CD138.

The UCART22 according to any one of the above wherein the anti-CD22 CAR is a single-chain CAR comprising an additional scFv specific for CD80.

The UCART22 according to any one of the above wherein the anti-CD22 CAR is a single-chain CAR comprising an additional scFv specific for BCMA (CD269).

The UCART22 according to any one of the above wherein the anti-CD22 CAR is a single-chain CAR comprising an additional scFv specific for TNFRSF 17, The UCART22 according to any one of the above wherein the anti-CD22 CAR is a single-chain CAR comprising an additional scFv specific for FLT-3.

The UCART22 according to any one of the above wherein the anti-CD22 CAR is a multi-chain CAR comprising an additional scFv specific for CD19.

The UCART22 according to any one of the above wherein the anti-CD22 CAR is a multi-chain CAR, comprising an additional scFv specific for CD79 a or CD79b.

The UCART22 according to any one of the above wherein the anti-CD22 CAR is a multi-chain CAR comprising an additional scFv specific for CD20.

The UCART22 according to any one of the above wherein the anti-CD22 CAR is a multi-chain CAR comprising an additional scFv specific for CD30.

The UCART22 according to any one of the above wherein the anti-CD22 CAR is a multi-chain CAR comprising an additional scFv specific for a major histocompatibility complex (MHC) molecule.

The UCART22 according to any one of the above wherein the anti-CD22 CAR is a multi-chain CAR comprising an additional scFv specific for an Immunoglobulin (Ig).

The UCART22 according to any one of the above wherein the anti-CD22 CAR is a multi-chain CAR comprising an additional scFv specific for CD3.

The UCART22 according to any one of the above wherein the anti-CD22 CAR is a multi-chain CAR comprising an additional scFv specific for CD5.

The UCART22 according to any one of the above wherein the anti-CD22 CAR is a multi-chain CAR comprising an additional scFv specific for CD34.

The UCART22 according to any one of the above wherein the anti-CD22 CAR is a multi-chain CAR comprising an additional scFv specific for CD138.

The UCART22 according to any one of the above wherein the anti-CD22 CAR is a multi-chain CAR comprising an additional scFv specific for CD80.

The UCART22 according to any one of the above wherein the anti-CD22 CAR is a multi-chain CAR comprising an additional scFv specific for BCMA (CD269).

The UCART22 according to any one of the above wherein the anti-CD22 CAR is a multi-chain CAR comprising an additional scFv specific for TNFRSF 17.

The UCART22 according to any one of the above wherein the anti-CD22 CAR is a multi-chain CAR comprising an additional scFv specific for FLT-3.

9. A population of UCART cells comprising the UCART22 according to any one of embodiment 1 to 8.

10. The population of UCART cells according to embodiment 9 comprising a UCART 19, preferably a UCART19 expressing an anti-CD19 CAR comprising a sequence of SEQ ID NO: 25 or SEQ ID NO: 26 at the cell surface.

11. A kit comprising a UCART22 and a UCART19 for a successive (at least once) or a concomitant or a successive (at least once) and then concomitant administration in a patient in need thereof.

12. The kit of embodiment 11 wherein the UCART19 is used first at least once, twice, three, four or several times, and then the UCART22, alone or with the UCART19.

13. The kit of embodiment 11 or 12 wherein the UCART22 is used first at least once, twice, three, four or several times, and then the UCART19, alone or with the UCART22.

14. The kit according to any one of embodiment 11 to 13 further comprising a lymphodepleting treatment, administered before the UCART.

15. The kit according to any one of embodiment 11 to 14 wherein lymphodepletion is achieved using fludarabine and cyclophosphamide, preferably fludarabine 25 mg/m$^2$ i.v.×5 doses on days −6 to −2 and cyclophosphamide 60 mg/kg i.v. for 1 dose on day −5.

16. The kit according to any one of embodiment 11 to 15 comprising at least one other UCART cell directed against a cancer antigen selected from CD79a, CD79b, CD20, CD30, CD52, CD40, CD80, CD86, CD74, VEGF.

17. A pharmaceutical composition comprising the UCART22 according to any one of embodiment 1 to 8 or a population of cells comprising said UCART22 according to embodiment 9 or 10 and a pharmaceutically acceptable excipient.

18. The pharmaceutical composition of embodiment 17 further comprising a bryostatin, preferably bryostatin-1.

19. The pharmaceutical composition of embodiment 17 or 18 or the kit according to any one of embodiment 11 to 16 for its use as a medication for preventing or treating a patient suffering a CD22+-mediated cancer or a CD22+-mediated inflammatory disease.

20. The pharmaceutical composition of according to any one of embodiment 17 to 18 or the kit according to any one of embodiment 11 to 16 for its use as a medication for preventing or treating a patient suffering a CD19+-mediated cancer or a CD19+-mediated inflammatory disease.

21. The pharmaceutical composition of according to any one of embodiment 17 to 18 or the kit according to any one of embodiment 11 to 16 for its use as a medication for preventing or treating a patient suffering a CD19+ CD22+-mediated cancer or a CD19+CD22+-mediated inflammatory disease.

22. The pharmaceutical composition of according to any one of embodiment 17 to 18 or the kit according to any one of embodiment 11 to 16 for its use according any one of embodiment 19 or 21, wherein treating a patient comprises a step of administering the pharmaceutical composition at least twice (re dosing) to avoid a relapse/refractory development of the cancer.

23. The pharmaceutical composition of according to any one of embodiment 17 to 18 or the kit according to any one of embodiment 11 to 16 for its use according any one of embodiment 19 or 21, for the treatment of a CD22-mediated hematological cancer selected from lymphoma, Hodgkin lymphoma, non-Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, preferably a CD22 expressing hematological cancer selected from (lymphoma, Hodgkin lymphoma, non-Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, more preferably a relapse refractory CD22-expressing hematological cancer, even more preferably an aggressive form of said CD22-related hematological cancer. 24. The pharmaceutical composition of according to any one of embodiment 17 to 18 or the kit according to any one of embodiment 11 to 16 for its use according any one of embodiment 20 or 21 for the treatment of a CD19-mediated hematological cancer selected from lymphoma, Hodgkin lymphoma, non-Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, preferably a CD19 expressing hematological cancer selected from (lymphoma, Hodgkin lymphoma, non-Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, more preferably a relapse refractory CD19-expressing hematological cancer, even more preferably an aggressive form of said CD19-related hematological cancer.

25. The pharmaceutical composition of according to any one of embodiment 17 to 18 or the kit according to any one of embodiment 11 to 16 for its use according any one of embodiment 19 to 22 for the treatment of a relapse or refractory expressing B ALL, preferably as a pediatric indication.

26. The pharmaceutical composition of according to any one of embodiment 17 to 18 or the kit according to any one of embodiment 11 to 16 for its use according any one of embodiment 19 to 25, wherein treating a patient comprises administering at least one monoclonal antibody (mAb), preferably QBEND-10 and or Rituximab, in a patient, at a dose allowing contacting said UCART22 with at least one specific mAb.

Embodiments for a Cd22 Car

The invention provides an anti-CD22 CAR comprising a hinge domain selected from FcRIIIα, CD8alpha, IgG1, IgG4, and PD1, preferably from CD8 alpha or IgG4.

The anti-CD22 CAR according the above wherein a scFv specific for CD22 comprising a VH and a VL linked to each other by a linker L1, preferably a linker comprising 1 to 3 "GGGGS" (SEQ ID NO: 29) motif, more preferably one GGGGS" (SEQ ID NO: 29) motif.

The anti-CD22 CAR according to any one of the above wherein said scFv specific for CD22 is linked to a transmembrane domain by a hinge selected from a hinge from FcRIIIa, CD8alpha, IgG1, preferably from CD8 alpha.

The anti-CD22 CAR according to any one of the above comprising an intracellular domain, said an intracellular domain comprising a CD3zeta signaling domain and a 4-1BB signaling domain.

The anti-CD22 CAR as any one of the above wherein the anti-CD22 CAR comprises at least one, preferably two, three or four monoclonal antibody (mAb)-specific epitopes, preferably two inserted into the linker L of the scFv specific for CD22 and/or into the hinge.

The anti-CD22 CAR as any one of the above, wherein the mAb-specific epitope is a polypeptide selected from: CPYSNPSLC (SEQ ID NO: 19), NSELLSLINDMPITNDQKKLMSNN (SEQ ID NO: 30), CQFDLSTRRLKC (SEQ ID NO: 31), CQYNLSSRALKC (SEQ ID NO: 32), CVWQRWQKSYVC (SEQ ID NO: 33), CVWQRWQKSYVC (SEQ ID NO: 34), SFVLNWYRMSPSNQTDKLAAFPEDR (SEQ ID NO: 35), SGTYLCGAISLAPKAQIKE (SEQ ID NO: 36), ELPTQGTFSNVSTNVSPAKPTTTA (SEQ ID NO: 37), GQNDTSQTSSPS (SEQ ID NO: 38), preferably ELPTQGTFSNVSTNVSPAKPTTTA (SEQ ID NO: 37) and/or CPYSNPSLC (SEQ ID NO: 19).

The invention provides a polynucleotide encoding an anti-CD22 CAR according to any one of the above or a polynucleotide having at least 80% identity with said a polynucleotide encoding an anti-CD22 CAR, a vector comprising a polynucleotide according to any one of the above polynucleotides.

As disclosed herein below, other genes are edited in said UCART22 in particular the dCK gene, the B2M gene, or the CD52 gene.

Ucart Provided

The UCART22 as above is provided wherein and at least one additional gene is edited or engineered, said gene is selected from a gene encoding aryl hydrocarbon receptor (AHR), Transforming growth factor beta receptor) (TGF beta receptor), Interleukin 10 receptor (IL-10 R), Programmed cell death protein 1, and a combination thereof.

The UCART22 as above wherein and at least one additional gene comprises a mutation, a deletion or an insertion inactivating its activity and/or expression said gene selected from a gene encoding aryl hydrocarbon receptor (AHR), Transforming growth factor beta receptor) (TGF beta receptor), Interleukin 10 receptor (IL-10 R), Programmed cell death protein 1, a combination thereof.

The UCART22 as above wherein and at least one additional gene comprises a mutation, a deletion or an insertion inactivating its activity and/or expression said gene selected from a gene encoding aryl hydrocarbon receptor (AHR), Transforming growth factor beta receptor) (TGF beta receptor), Interleukin 10 receptor (IL-10 R), a combination thereof.

The UCART22 as above wherein and at least one additional gene comprises a mutation, a deletion or an insertion inactivating its activity and/or expression said gene selected from a gene encoding Transforming growth factor beta receptor) (TGF beta receptor), Interleukin 10 receptor (IL-10 R), Programmed cell death protein 1, and a combination thereof.

The UCART22 as above wherein and at least one additional gene comprises a mutation, a deletion or an insertion inactivating its activity and/or expression said gene selected from a gene encoding aryl hydrocarbon receptor (AHR), Interleukin 10 receptor (IL-10 R), Programmed cell death protein 1, and a combination thereof.

The UCART22 as above wherein and at least one additional gene comprises a mutation, a deletion or an insertion inactivating its activity and/or expression said gene selected from a gene encoding aryl hydrocarbon receptor (ATHR), Transforming growth factor beta receptor) (TGF beta receptor), Programmed cell death protein 1, and a combination thereof.

Gene in which said CAR may be inserted are described below in Table 1.

TABLE 1

List of genes encoding immune checkpoint proteins that may be inactivated according to the present invention in the CD22 CAR engineered T cells of the invention

| Pathway | | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1 (PD-1, CD279) | PDCD1 |
| | CD223 (lag3) | LAG3 |
| | HAVCR2 (tim3) | HAVCR2 |
| | BTLA(cd272) | BTLA |
| | CD160(by55) | CD160 |
| | IgSFfamily | TIGIT |
| | | CD96 |
| | | CRTAM |
| | LAIR1(cd305) | LAIR1 |
| | SIGLECs | SIGLEC7 |
| | | SIGLEC9 |
| | CD244(2b4) | CD244 |
| Death receptors | TRAIL | TNFRSF10B, TNFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL6ST |
| Prevention of TCR signalling | | CSK, PAG1 SIT1 |
| Induced Treg | induced Treg | FOXP3 |
| Transcription factors controlling exhaustion | transcription factors controlling exhaustion | PRDM1 (=blimp1, heterozygotes mice control chronic viral infection better than wt or conditional KO) BATF |
| Hypoxia mediated tolerance | iNOS induced guanylated cyclase | GUCY1A2, GUCY1A3, GUCY1B2, GUCY1B3 |

In bold are the preferred gene inactivated in the UCART of the invention

The UCART22 as above comprising an anti-CD22 CAR (UCART22) according to any one of the above and a polynucleotide coding said anti-CD22 CAR (UCART22) inserted into the genome, into the CD25 gene.

The UCART22 according to any one of the above wherein the anti-CD22 CAR is a single-chain CAR or a multi-chain CAR.

The UCART22 according to any one of the above wherein the anti-CD22 CAR is a single-chain CAR comprising an additional scFv specific for any one of the following tumor-associated surface antigens selected from CD19, CD20, CD30, a major histocompatibility complex (MHC) molecule, an Immunoglobulin (Ig), CD3, CD5, CD34, CD79, preferably CD79b, CD138, B7-1 (CD80), BCMA (CD269, TNFRSF 17), FLT-3, or PAX5, preferably CD19.

The UCART22 according to any one of the above wherein the anti-CD22 CAR is a single-chain CAR comprising an additional scFv specific for CD19.

The UCART22 according to any one of the above expressing an anti-CD22 CAR and an anti-CD19CAR, preferably of SEQ ID NO: 94 or of SEQ ID NO: 95.

The UCART22 according to any one of the above wherein the anti-CD22 CAR is a single-chain CAR comprising an additional scFv specific for CD20.

The UCART22 according to any one of the above wherein the anti-CD22 CAR is a single-chain CAR comprising an additional scFv specific for CD30.

The UCART22 according to any one of the above wherein the anti-CD22 CAR is a single-chain CAR comprising an additional scFv specific for a major histocompatibility complex (MHC) molecule.

The UCART22 according to any one of the above wherein the anti-CD22 CAR is a single-chain CAR comprising an additional scFv specific for an Immunoglobulin (Ig).

The UCART22 according to any one of the above wherein the anti-CD22 CAR is a single-chain CAR comprising an additional scFv specific for CD3.

The UCART22 according to any one of the above wherein the anti-CD22 CAR is a single-chain CAR comprising an additional scFv specific for CD5.

The UCART22 according to any one of the above wherein the anti-CD22 CAR is a single-chain CAR comprising an additional scFv specific for CD34.

The UCART22 according to any one of the above wherein the anti-CD22 CAR is a single-chain CAR comprising an additional scFv specific for CD79, preferably CD79b.

The UCART22 according to any one of the above wherein the anti-CD22 CAR is a single-chain CAR comprising an additional scFv specific for CD138.

The UCART22 according to any one of the above wherein the anti-CD22 CAR is a single-chain CAR comprising an additional scFv specific for CD80.

The UCART22 according to any one of the above wherein the anti-CD22 CAR is a single-chain CAR comprising an additional scFv specific for BCMA (CD269).

The UCART22 according to any one of the above wherein the anti-CD22 CAR is a single-chain CAR comprising an additional scFv specific for TNFRSF 17, The UCART22 according to any one of the above wherein the anti-CD22 CAR is a single-chain CAR comprising an additional scFv specific for FLT-3.

The UCART22 according to any one of the above wherein the anti-CD22 CAR is a multi-chain CAR.

The UCART22 according to any one of the above wherein the anti-CD22 CAR is a multi-chain CAR comprising an additional scFv specific for CD19.

The UCART22 according to any one of the above wherein the anti-CD22 CAR is a multi-chain CAR, comprising an additional scFv specific for CD79 a or CD79b.

The UCART22 according to any one of the above wherein the anti-CD22 CAR is a multi-chain (mc) CAR comprising an additional scFv specific for CD19.

The UCART22 according to any one of the above expressing an anti-CD22 mcCAR and an anti-CD19CAR, preferably of SEQ ID NO: 94 or of SEQ ID NO: 95.

The UCART22 according to any one of the above wherein the anti-CD22 CAR is a multi-chain CAR comprising an additional scFv specific for CD20.

The UCART22 according to any one of the above wherein the anti-CD22 CAR is a multi-chain CAR comprising an additional scFv specific for CD30.

The UCART22 according to any one of the above wherein the anti-CD22 CAR is a multi-chain CAR comprising an additional scFv specific for a major histocompatibility complex (MHC) molecule.

The UCART22 according to any one of the above wherein the anti-CD22 CAR is a multi-chain CAR comprising an additional scFv specific for an Immunoglobulin (Ig).

The UCART22 according to any one of the above wherein the anti-CD22 CAR is a multi-chain CAR comprising an additional scFv specific for CD3.

The UCART22 according to any one of the above wherein the anti-CD22 CAR is a multi-chain CAR comprising an additional scFv specific for CD5.

The UCART22 according to any one of the above wherein the anti-CD22 CAR is a multi-chain CAR comprising an additional scFv specific for CD34.

The UCART22 according to any one of the above wherein the anti-CD22 CAR is a multi-chain CAR comprising an additional scFv specific for CD138.

The UCART22 according to any one of the above wherein the anti-CD22 CAR is a multi-chain CAR comprising an additional scFv specific for CD80.

The UCART22 according to any one of the above wherein the anti-CD22 CAR is a multi-chain CAR comprising an additional scFv specific for BCMA (CD269).

The UCART22 according to any one of the above wherein the anti-CD22 CAR is a multi-chain CAR comprising an additional scFv specific for TNFRSF 17, The UCART22 according to any one of the above wherein the anti-CD22 CAR is a multi-chain CAR comprising an additional scFv specific for FLT-3.

A population of cells comprising the UCART22 according to any one of the above.

A population of cells comprising the UCART22 according to any one of the above and wherein cells expressing said anti-CD22 CAR also express an anti-CD19 CAR, preferably said anti-CD19 CAR comprises a sequence of SEQ ID NO: 25 or SEQ ID NO: 26 at the cell surface.

A CD22 CAR T cell (UCART22), optionally combined to a protein kinase C inhibitor such as bryostatin 1 as a pharmaceutical composition of the invention, is particularly useful in for the treatment of CLL, ALL, Multiple myeloma, (MM), Blastic plasmacytoid dendritic cell neoplasm (BPDCN), especially refractory/relapse ALL, refractory/relapse CLL and or aggressive forms of these diseases, more preferably refractory or relapse B-ALL.

A CD22 CAR T cell (UCART22), derived from m971, optionally combined to a protein kinase C inhibitor such as bryostatin 1 as a pharmaceutical composition of the invention, is particularly useful in for the treatment of CLL, ALL, Multiple myeloma, (MM), Blastic plasmacytoid dendritic cell neoplasm (BPDCN), especially refractory/relapse ALL, refractory/relapse CLL and or aggressive forms of these diseases, more preferably refractory or relapse B-ALL.

The engineered immune cells of the present invention not only display high level of in vivo activity toward malignant cells, less cytokine release but also their number and activity is controlled conferring safety and efficiency for immunotherapy.

The present invention provides an engineered human T Cell Receptor Knock Out (TCR KO) cell endowed with a Chimeric Antigen Receptor specific for CD22 (CD22 CAR) (UCART22), preferably expressed at the cell surface, wherein said CD22 CAR comprises:
  i) at least one extracellular domain comprising:
    a hinge domain from CD8alpha, and
    an antigen binding domain specific for CD22, optionally a leader sequence,
  ii) a transmembrane domain from CD8alpha, and
  iii) an intracellular signaling domain. said UCART22 comprising at least one additional edited gene, preferably a deletion in the CD52 gene.

The present invention also provides the UCART CD22 as above wherein the antigen binding domain comprises a scFv specific for CD22, derived from a m917 antibody (m971), preferably said scFv comprises a sequence selected from SEQ ID NO: 12, SEQ ID NO: 13, SEQ ID NO: 14 and from SEQ ID NO: 15, more preferably a sequence from SEQ ID NO: 15.

In one embodiment the present invention also provides an engineered human T Cell Receptor Knock Out (TCR KO) cell endowed with a Chimeric Antigen Receptor specific for CD22 (CD22 CAR) (UCART22), preferably expressed at the cell surface, wherein said CD22 CAR comprises:
  i) at least one extracellular domain comprising:
    a hinge domain from CD8alpha, and
    an antigen binding domain specific for CD22, optionally a leader sequence,
  ii) a transmembrane domain from CD8alpha, and
  iii) an intracellular signaling domain. said UCART22 comprising at least one additional edited gene, preferably a deletion in the CD52 gene and wherein the antigen binding domain comprises a scFv specific for the distal part of CD22, said CAR having a SEQ ID NO: 20.

The UCART CD22 according to the above comprising the following sequences: QVQLQQSGPGLVKPSQTLSLT-CAISGDSVSSNSAAWNWIRQSPSRGLEWLGRTYYR-SKWYN DYAVSVKSRITINPDTSKNQFSLQLNSVT-PEDTAVYYCAREVTGDLEDAFDIWGQGTMVTV SS (SEQ ID NO: 12) and DIQMTQSPSSLSASVGDRVTIT-CRASQTIWSYLNWYQQRPGKAPNLLIYAASSLQS GVPSRFS GRGSGTDFTLTISSLQAEDFATYYCQQSYS-IPQTFGQGTKLEIK (SEQ ID NO: 13) or having 80 to 99% homology with each of said sequences.

The present invention also provides a UCART22 as above comprising a polypeptide of SEQ ID NO: 15 and a safety switch comprising: a RQR8 temporarily linked to the CD22 CAR by a peptide 2A or at least two rituximab mAb-specific epitopes, preferably 3 rituximab mAb-specific epitopes and more preferably 3 rituximab mAb-specific epitopes and a QBEND-10 mAb-specific epitopes linked to the CD22 CAR [allowing both sorting and/or depletion of the immune cells endowed with said CD22 CAR].

The present invention also provides a UCART22 as above comprising at least one additional edited gene, preferably a deletion in CD52 gene, or in a dCK gene or a deletion in a β2 Microglobulin gene or in CTIIA gene, even more preferably a deletion in CD52 gene, and/or an insertion in the HIF-1alpha gene, conferring resistance to hypoxia.

The present invention provides a UCART22 as above comprising a deletion in CD52 gene, in combination with alemtuzumab.

The present invention also provides a UCART22 as above wherein said CD22 CAR is expressed under hypoxia (low O₂ concentration that is less than 5% O₂, preferably less than 1% O₂).

The present invention also provides a UCART22 as above comprising a polynucleotide encoding a polypeptide comprising a CD22 CAR and a safety switch. In a preferred embodiment, the present invention provides a UCART22 as above comprising a polynucleotide of SEQ ID NO: 22 and of SEQ ID NO: 18 in the same gene, preferably in the TRAC gene.

The present invention also provides a UCART22 as above comprising a polynucleotide encoding a polypeptide comprising a CD22 CAR and a safety switch. In a preferred embodiment, the present invention provides a UCART22 as above comprising a polynucleotide of SEQ ID NO: 20 and of SEQ ID NO: 18 in the same gene, preferably in the TRAC gene.

The present invention provides a population of cells comprising a UCART22 as above.

The present invention provides a pharmaceutical composition comprising either the UCART22 as above or a population of cells comprising said UCART22 any of the above and a pharmaceutically acceptable excipient.

In particular embodiments, a pharmaceutical composition comprising the UCART22 according to the invention or a population of cells comprising said UCART22 in combination with a UCART19 and a pharmaceutically acceptable excipient is provided. UCART19 and UCART22 may be given at the same time, concomitantly or successively starting by UCART 19 or by UCART22 as a function of CD19 and CD22 expression level a cancer cells of patients.

In particular embodiments, a pharmaceutical composition comprising the UCART22/19 or UCART19/22 (bispecific CAR single chain or multichain CAR or cells expressing both CD19CAR and CD22 CAR) and a pharmaceutically acceptable excipient, is provided. The present invention provides a pharmaceutical composition as above further comprising a compound of the bryostatin family, preferably bryostatin 1.

The present invention provides a therapeutically effective amount of UCART22 as above or of the pharmaceutical composition comprising said UCART22 as above for use as a medication for treating a patient.

The present invention provides a therapeutically effective amount of UCART22 as above or of the pharmaceutical composition as above for use as a medication for treating a patient wherein treating a patient comprises administering at least two times (re dosing) said therapeutically effective amount of UCART22 or said pharmaceutical composition for avoiding a relapsing.

In a particular embodiment, the present invention provides a UCART22 according to any one of the above or the pharmaceutical composition according to any one of the above for use as a medication for treating a patient wherein treating a patient comprises administering a UCART22 as above or a pharmaceutical composition as above at least two times for avoiding the relapsing.

The present invention provides a therapeutically effective amount of UCART22 as above or of the pharmaceutical composition as above for use as a medication for treating a patient as above for the treatment of a CD22-related pathology, preferably a CD22-related B-cell malignancy (eg CD22-related hematological cancer).

In a particular embodiment, the present invention provides:

The therapeutically effective amount of UCART22 as above or of the pharmaceutical composition as above for use as a medication for the treatment of a hematological cancer such as a hematological cancer selected from lymphoma, Hodgkin lymphoma, non-Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, preferably a CD22-expressing hematological cancer, more preferably a relapse refractory CD22-expressing hematological cancer, even more preferably an aggressive form of said CD22-related hematological cancer. Preferably the UCART22 is used for treating patients with relapse refractory B ALL.

The present invention provides a therapeutically effective amount of UCART22 as above or of a pharmaceutical composition as above for use as a medication for treating a patient wherein said patient suffers from a cancer selected from alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, cancer of the gallbladder, cancer of the pleura, cancer of the nose, cancer of the nasal cavity, cancer of the middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), hypopharynx cancer, kidney cancer, larynx cancer, liver cancer, lung cancer (e.g., non-small cell lung carcinoma), malignant mesothelioma, mastocytoma, melanoma, nasopharynx cancer, ovarian cancer, pancreatic cancer, peritoneum cancer, omentum cancer, mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer.

The present invention provides:

1. An engineered human T Cell Receptor Knock Out (TCR KO) cell endowed with a Chimeric Antigen Receptor (CAR) specific for CD22 (UCART22), preferably expressed at the cell surface, wherein said anti-CD22 CAR comprises:
   i) at least one extracellular domain comprising:
      a hinge domain from CD8alpha, and
      an antigen binding domain specific for CD22, optionally a leader sequence,
   ii) a transmembrane domain from CD8alpha, and
   iii) an intracellular signaling domain. said UCART22 comprising at least one additional edited gene, preferably a CD52 inactivated gene, a dCK inactivated gene, a β2 Microglobulin inactivated gene or an inserted HIF-1alpha gene.
2. The UCART CD22 according to 1 wherein the antigen binding domain comprises a scFv specific for CD22, said scFv is derived from a m917 antibody (m971), preferably said scFv comprises a sequence selected from SEQ ID NO: 12, SEQ ID NO: 13, SEQ ID NO: 14 or from SEQ ID NO: 15, more preferably a sequence from SEQ ID NO: 15.

3. The UCART22 according to any one of 1 to 2 comprising a polypeptide of SEQ ID NO: 15 and a safety switch, said safety switch comprising: a RQR8 temporarily linked to the CD22 CAR by a peptide 2A, or at least two rituximab mAb-specific epitopes, preferably 3 rituximab mAb-specific epitopes and more preferably 3 rituximab mAb-specific epitopes and a QBEND-10 mAb-specific epitopes linked to the CD22 CAR [allowing both sorting and/or depletion of the immune cells endowed with said CD22 CAR].

4. The UCART22 according to any one of 1 to 3 comprising a CD52 inactivated gene, even more preferably a CD52 inactivated gene and HIF-1alpha inserted gene conferring resistance alemtuzumab and to hypoxia.

5. The UCART22 according to any one of 1 to 4 wherein said anti-CD22 CAR is expressed at the cell surface under low $O_2$ concentration (<5% $O_2$).

6. The UCART22 according to any one of 1 to 5 comprising a polynucleotide encoding a polypeptide comprising an anti-CD22 CAR as in 1 to 5.

The UCART22 according to any one of the above comprising an anti-CD22 CAR at the cell surface, a polynucleotide encoding said anti-CD22 CAR inserted into the TRAC gene and an exogenous polynucleotide sequence encoding IL-12 inserted into the CD25 genomic sequence, the B2M genomic sequence or into the PD1 genomic sequence.

The UCART22 according to any one of the above comprising an anti-CD22 CAR at the cell surface, a polynucleotide encoding said anti-CD22 CAR inserted into the TRAC gene and an exogenous polynucleotide sequence encoding IL-12 inserted into the CD25 genomic sequence or into the PD1 genomic sequence and further comprising genomic KO gene selected from IL-10Receptor, TGFbeta receptor, TIM-3, and LAG-3 (see Table 1 above).

7. The UCART22 according to any one of 1 to 6 further comprising a polynucleotide of SEQ ID NO: 22, preferably comprising a sequence of SEQ ID NO: 18 and 22 in the same TRAC gene.

8. A population of cells comprising said UCART22 according to any one of 1 to 7.

9. A pharmaceutical composition comprising the UCART22 according to any one of 1 to 7 or a population of cells comprising said UCART22 according to 8 and a pharmaceutically acceptable excipient.

10. The pharmaceutical composition according to 9 further comprising a bryostatin, preferably bryostatin-1.

11. A therapeutically effective amount of UCART22 according to any one of 1 to 7 or of the pharmaceutical composition according to 9 or 10 for use as a medication for treating a patient.

12. The therapeutically effective amount of UCART22 according to any one of 1 to 7 or of the pharmaceutical composition according to 9 or 10 for use as a medication for treating a patient according to 11 wherein treating a patient comprises administering at least two times (re dosing) said therapeutically effective amount of UCART22 or said pharmaceutical composition for avoiding a relapsing.

13. The therapeutically effective amount of UCART22 according to any one of 1 to 7 or of the pharmaceutical composition according to 9 or 10 for use as a medication for treating a patient according to 11 or 12 for the treatment of a CD22-related pathology, preferably a CD22-related B-cell malignancy.

14. The therapeutically effective amount of UCART22 according to any one of 1 to 7 or of the pharmaceutical composition according to 9 or 10 for use as a medication for treating a patient according to any one of 11 to 13 for use in the treatment of a hematological cancer selected from (lymphoma, Hodgkin lymphoma, non-Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, preferably a CD22-expressing hematological cancer, more preferably a relapse or refractory CD22-expressing hematological cancer, even more preferably an aggressive form of said CD22-related hematological cancer.

15. The therapeutically effective amount of UCART22 according to any one of 1 to 7 or of the pharmaceutical composition according to 9 or 10 for use as a medication for treating a patient according to any one of 11 to 13 for use in the treatment of relapsed and/or refractory CD22 positive B-ALL.

16. The therapeutically effective amount of UCART22 according to any one of 1 to 7 or of the pharmaceutical composition according to 9 or 10 for use as a medication for treating a patient according to any one of 11 to 13 wherein said patient suffers from a cancer, preferably mediated by CD22+cells, selected from alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, cancer of the gallbladder, cancer of the pleura, cancer of the nose, cancer of the nasal cavity, cancer of the middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), hypopharynx cancer, kidney cancer, larynx cancer, liver cancer, lung cancer (e.g., non-small cell lung carcinoma), malignant mesothelioma, mastocytoma, melanoma, nasopharynx cancer, ovarian cancer, pancreatic cancer, peritoneum cancer, omentum cancer, mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer, preferably liver cancer and lung cancer.

BRIEF DESCRIPTION OF THE FIGURES

FIG. 2 illustrates examples of CD22 CAR according to the invention, comprising a scFv specific for CD22, optionally comprising a safety switch, a hinge and a transmembrane domain from CD8 alpha, an intracellular domains from 4-1BB and CD3 zeta, optionally a domain conferring resistance to hypoxia.

FIG. 4 represents one example of polypeptide which will be cleaved so that a safety switch (RQR8) and a CD22 CAR will be expressed at the cell surface. R=CD20 mimotope (bound by Rituximab), Q=CD34 epitope (bound by QBEND-10)

DETAILED DESCRIPTION OF THE INVENTION

Figure 1:
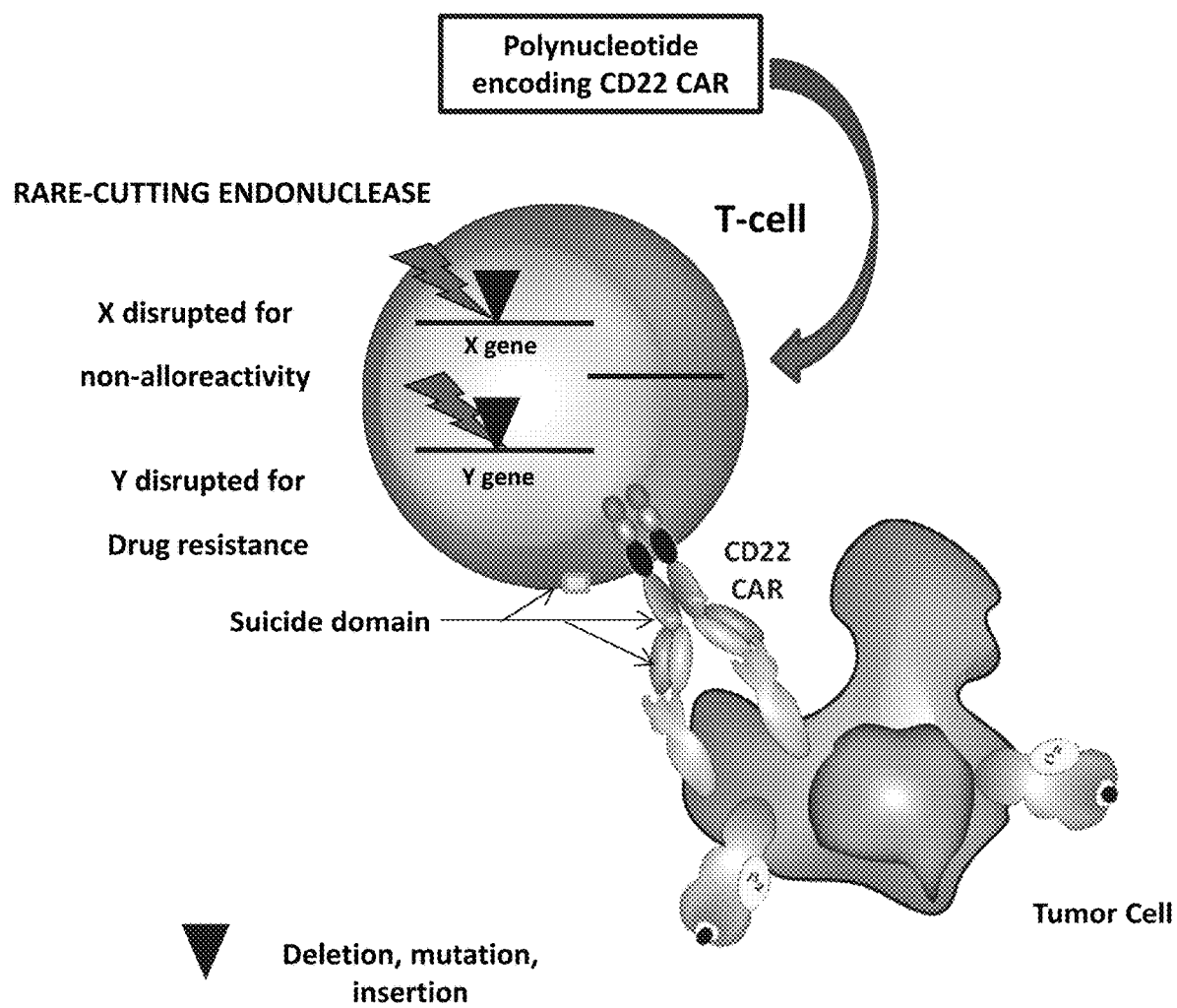
FIG. 1: Schematic representation of an engineered immune cell according to the invention. The engineered immune cell presented in FIG. 1 may be a T-cell endowed with a polynucleotide encoding a CAR of the invention. This T-cell is further engineered to allow a better and safer engraftment into the patient. X, or Y is an edited gene that may be mutated, deleted and/or having an insertion. For instance, a gene expressing a component of the T cell receptor (TCR) for example the TCRalpha or TCRbeta may be deleted or may comprise an insertion, Y may be a gene involved into the sensitivity of T-cells to immune-suppressive drugs like dCK (with respect to resistance to purine nucleotide analogues) or CD52 (with respect to CAMPATH®) or HPRT (with respect to 6-Thioguanine).

Unless specifically defined herein, all technical and scientific terms used have the same meaning as commonly understood by a skilled artisan in the fields of gene therapy, biochemistry, genetics, immunology and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription and Translation (B. D. Hames & S. J. Higgins eds. 1984); Culture of Animal Cells (R. I. Freshney, Alan R. Liss, Inc., 1987); Immobilized Cells and Enzymes (IRL Press, 1986); B. Perbal, A Practical Guide to Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors for Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Cd22 Specific Chimeric Antigen Receptors

The present invention relates to new designs of anti-CD22 chimeric antigen receptor (CAR or CD22 CAR or anti-CD22 CAR) which are chimeric antigen receptor capable of binding to CD22 in particular to the proximal domain of CD22.

The CD22 specific Chimeric Antigen Receptors of the invention comprises an extracellular domain comprising an extracellular ligand-binding domain and a hinge, optionally a suicide domain, a transmembrane domain and an intracellular domain comprising a signaling transducing domain.

Expressed at a cell surface, a CD22 CAR according to the present invention comprises an extracellular domain that comprises an extracellular ligand-binding domain.

The term "extracellular ligand-binding domain" as used herein is defined as an oligo- or polypeptide that is capable of binding at least one epitope of CD22. Preferably, the extracellular ligand-binding domain will be capable of interacting at least partially with a cell surface molecule interacting with CD22 and with another cell surface antigen or another membrane bound antigen, or of interacting directly with CD22, or of interacting with human CD22, more precisely of interacting directly with the proximal region of human CD22 (from amino acid 243 to amino acid 687).

In one embodiment, a CD22 CAR according to the present invention comprises an extracellular domain that comprises an extracellular ligand-binding domain capable of interacting with the proximal region of CD22 (from amino acid 243 to amino acid 687) and with the distal part of CD22 (from aa 20 to aa 425).

In the present invention, the full-length extracellular domain of CD22 is from amino acid (aa) 20-to aa 687, the membrane proximal domain of CD22 is from aa 243 to aa 687, the membrane distal domain of CD22 is from aa 20 to aa 425.

In one embodiment, the extracellular ligand-binding domain may be chosen to recognize a particular form (glycosylated) CD22 that acts as a cell surface marker on target cells associated with a particular disease state.

In a preferred embodiment, said extracellular ligand-binding domain comprises at least one single chain antibody fragment (scFv) comprising the light ($V_L$) and the heavy ($V_H$) variable fragment of a target antigen specific monoclonal anti CD22 antibody joined by a linker, in particular a flexible linker. Said $V_L$ and $V_H$ are preferably from the antibody m971 as in Table 2 below. They are preferably linked together by a flexible linker comprising for instance the sequence SEQ ID NO.10.

For the purpose of the present invention, specific parts of the fully human anti-CD22 antibody, m971 antibody (m971) previously identified using phage display methodology and characterized. (Xiao X, Ho M, Zhu Z, Pastan I, Dimitrov D S. Identification and characterization of fully human anti-CD22 monoclonal antibodies. *mAbs.* 2009; 1(3):297-303) were combined to specific sequences to produce new CD22 CARs, according to the invention. See, also, WO 2014065961, which is incorporated by reference.

A preferred embodiment of the invention provides CARs comprising an antigen-binding domain comprising, consisting of, or consisting essentially of, a single chain variable fragment (scFv) of the antigen binding domain of m971 with the following moieties as in Table 2.

TABLE 2

Sequence of different domains in CD22 CAR

| Functional domains | SEQ ID # | Raw amino acid sequence |
|---|---|---|
| CD8α signal peptide (or sequence leader) | SEQ ID NO. 1 | MALPVTALLLPLALLLHAARP |
| Alternative signal peptide | SEQ ID NO. 2 | METDTLLLWVLLLWVPGSTG |
| FcγRIIIα hinge | SEQ ID NO. 3 | GLAVSTISSFFPPGYQ |
| CD8α hinge | SEQ ID NO. 4 | TTTPAPRPPTPAPTIASQPLSLRPEACRPAAGGAVHTR GLDFACD |
| IgG1 hinge | SEQ ID NO. 5 | EPKSPDKTHTCPPCPAPPVAGPSVFLFPPKPKDTLMIA RTPEVTCVVVDVSHEDPEVKFNWYVDGVEVHNAKTK PREEQYNSTYRVVSVLTVLHQDWLNGKEYKCKVSNK ALPAPIEKTISKAKGQPREPQVYTLPPSRDELTKNQVSL TCLVKGFYPSDIAVEWESNGQPENNYKTTPPVLDSDG SFFLYSKLTVDKSRWQQGNVFSCSVMHEALHNHYTQ KSLSLSPGK |
| CD8α transmembrane domain | SEQ ID NO. 6 | IYIWAPLAGTCGVLLLSLVITLYC |
| 41BB transmembrane domain | SEQ ID NO. 7 | IISFFLALTSTALLFLLFFLTLRFSVV |
| 41BB intracellular domain | SEQ ID NO. 8 | KRGRKKLLYIFKQPFMRPVQTTQEEDGCSCRFPEEEE GGCEL |
| CD3ζ intracellular domain | SEQ ID NO. 9 | RVKFSRSADAPAYQQGQNQLYNELNLGRREEYDVLD KRRGRDPEMGGKPRRKNPQEGLYNELQKDKMAEAY SEIGMKGERRRGKGHDGLYQGLSTATKDTYDALHM QALPPR |
| Linker | SEQ ID NO. 10 | GGGGSGGGGSG GGGS |

TABLE 3

Sequence of the different CD22 scfv VH and VL

| ScFv sequences | SEQ ID # | Raw amino acid sequence |
|---|---|---|
| m971-heavy chain variable region | SEQ ID NO. 12 | QVQLQQSGPGLVKPSQTLSLTCAISGDSVSSNSAAWNWIR QSPSRGLEWLGRTYYRSKWYNDYAVSVKSRITINPDTSKN QFSLQLNSVTPEDTAVYYCAREVTGDLEDAFDIWGQGTM VTVSS |
| m971-light chain variable region | SEQ ID NO. 13 | DIQMTQSPSSLSASVGDRVTITCRASQTIWSYLNWYQQRP GKAPNLLIYAASSLQSGVPSRFSGRGSGTDFTLTISSLQAEDF ATYYCQQSYSIPQTFGQGTKLEIK |

TABLE 4

CD22 CAR of structure V-1

| CAR | CAR Structure | | | | | | |
|---|---|---|---|---|---|---|---|
| Designation V-1 | signal peptide | VH | VL | FcγRIIIα hinge | CD8α TM | 41BB-IC | CD3ζ CD |
| m971 (SEQ ID NO. 14) | SEQ ID NO. 1 | SEQ ID NO. 12 | SEQ ID NO. 13 | SEQ ID NO. 3 | SEQ ID NO. 6 | SEQ ID NO. 8 | SEQ ID NO. 9 |

TABLE 5

CAR of structure V-3

| CAR | CAR Structure | | | | | | |
|---|---|---|---|---|---|---|---|
| Designation V-3 | signal peptide | VH | VL | CD8αhinge | CD8α-TM | 41BB-IC | CD3ζ CD |
| m971(SEQ ID NO. 15) | SEQ ID NO. 1 | SEQ ID NO. 12 | SEQ ID NO. 13 | SEQ ID NO. 4 | SEQ ID NO. 6 | SEQ ID NO. 8 | SEQ ID NO. 9 |

In a preferred embodiment, the CD22 CAR of the invention comprises a sequence of SEQ ID NO: 15. In a preferred embodiment, the CD22 CAR of the invention comprises a sequence of SEQ ID NO: 23.

Sequences of CD22 CARs of the invention comprise a peptide signal, a TM domain from CD8alpha and a linker between the VH and VL domain from m971.

Scfv

In the present invention, a scFv is a fusion protein of the variable region of the heavy ($V_{H\ domain}$) and light chain ($V_{L\ domain}$) of an immunoglobulin or a part of an immunoglobulin specific for CD22, connected with a short linker peptide of 10 to 25 amino acids, preferably of SEQ ID NO: 10.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 12.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 13.

In a preferred embodiment, said CARs preferentially comprise an extracellular ligand-binding domain comprising a polypeptide sequence displaying at least 90%, 95%, 96%, 97%, 98%, 99% or 100% identity with an amino acid sequence SEQ ID NO: 12. and a polypeptide sequence displaying at least 90%, 91%, 92% 93% 94%, 95%, 96%, 97%, 98%, 99% or 100% identity with an amino acid sequence selected from the group consisting of SEQ ID NO: 13.

Hinge

The extracellular domain can further comprise a hinge region between said extracellular ligand-binding domain and said transmembrane domain. The term "hinge region" used herein generally means any oligo- or polypeptide that functions to link the transmembrane domain to the extracellular ligand-binding domain. In particular, hinge region is used to provide more flexibility and accessibility for the extracellular ligand-binding domain. A hinge region may comprise up to 300 amino acids, preferably 10 to 100 amino acids and most preferably 10 to 50 amino acids. Hinge region may be derived from all or part of naturally occurring molecules, such as from all or part of the extracellular region of CD8, or CD4, or from all or part of an antibody constant region. Alternatively, the hinge region may be a synthetic sequence that corresponds to a naturally occurring hinge sequence, or may be an entirely synthetic hinge sequence. In a preferred embodiment said hinge domain comprises a part of a human CD8 alpha chain, FcRIIIα receptor or IgG1, respectively referred to in this specification as SEQ ID NO: 4, SEQ ID NO: 5 and SEQ ID NO: 6, or in a more preferred embodiment, a hinge polypeptide which display at least 80%, preferably at least 90%, 95%, 97%, 99% or 100% sequence identity with SEQ ID NO: 4, even more preferably 100% sequence identity with SEQ ID NO: 4.

A hinge from IgG4 or from PD1 is part of the present invention and disclosed in WO2016120216 and may be used in the construction of a CD22 CAR according to the invention.

A CD22 CAR according to the present invention is anchored into the membrane of the cell. Thus, such CD22 CAR further comprises a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T-cell receptor such as α, β, or δ polypeptide constituting CD3 complex, IL2 receptor p55 (α chain), p75 (β chain) or chain, subunit chain of Fc receptors, in particular Fc receptor III or CD proteins. Alternatively, the transmembrane domain can be synthetic and can comprise predominantly hydrophobic residues such as leucine and valine. In a preferred embodiment said transmembrane domain is derived from the human CD8 alpha chain (e.g., NP_001139345.1).

A CD22CAR according to the invention generally further comprises a transmembrane domain (TM) more particularly from CD8a, showing identity with the polypeptides of SEQ ID NO: 6 or SEQ ID NO: 7. Preferably, a CAR according to the invention comprises a TM showing at least 70%, preferably at least 80%, more preferably at least 90%, 91%, 92%, 93%, 94%, 95%, 96%, 97%, 98%, 99% or 100% sequence identity with the polypeptides of SEQ ID NO: 6.

A CD22 CAR according to the invention generally further comprises a transmembrane domain (TM) from CD8a showing identity with the polypeptides of SEQ ID NO: 6. Preferably, a CAR according to the invention comprises a TM showing at least 70%, preferably at least 80%, more preferably at least 90%, 91%, 92%, 93%, 94%, 95%, 96%, 97%, 98%, 99% or 100% sequence identity with the polypeptides of SEQ ID NO: 6.

A CD22 CAR according to the present invention comprises an intracellular domain that comprises a signal transducing domain or intracellular signaling domain.

The signal transducing domain or intracellular signaling domain of a CD22 CAR according to the present invention is responsible for intracellular signaling following the binding of extracellular ligand binding domain to the target resulting in the activation of the immune cell and immune response (cytolytic activity against the target cell). In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function.

Preferred examples of signal transducing domain in a CD22 CAR of the invention can be the cytoplasmic sequences of the T cell receptor and co-receptors that act in concert to initiate signal transduction following antigen receptor engagement, as well as any derivate or variant of these sequences and any synthetic sequence that has the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the CAR can comprise the CD3zeta signaling domain which has amino acid sequence with at least 70%, preferably at least 80%, more preferably at least 90%, 95% 97% 99% or 100% sequence identity with amino acid sequence selected from the group consisting of (SEQ ID NO: 9). Optionally said CD3zeta signaling domain is comprising a polypeptide sequence displaying at least 90%, 91%, 92% 93%, 94%, 95%, 96%, 97%, 98%, 99% or 100% identity with SEQ ID NO: 9.

In a more preferred embodiment, the signaling transducing domain of the CD22 CAR consists in a CD3zeta signaling domain of SEQ ID NO: 9 and excludes any sequence from human CD28 signaling domain. In particular embodiment the signal transduction domain of the CAR of the present invention comprises a co-stimulatory signal molecule. A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, 4-1BB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to, an MHC class I molecule, BTLA and Toll ligand receptor. Examples of costimulatory molecules include CD27, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In a preferred embodiment, the signal transduction domain of the CAR of the present invention comprises a part of co-stimulatory signal molecule consisting of fragment of 4-1BB (GENBANK®: AAA53133.) In particular, the signal transduction domain of the CAR of the present invention comprises amino acid sequence which comprises at least 70%, preferably at least 80%, more preferably at least 90%, 95%, 97%, 99% or 100% sequence identity with amino acid sequence of SEQ ID NO: 8.

In a more preferred embodiment, the signal transduction domain of the CAR of the present invention comprises no sequence from CD28 (NP_006130.1).

In an even more preferred embodiment, all the embodiments of the present invention comprise no sequence from CD28 (NP_006130.1).

In an even more preferred embodiment, the signal transduction domain of the CD22 CAR of the present invention comprises a part of co-stimulatory signal molecule 4-1BB (GENBANK®: AAA53133) and no sequence from CD28 (NP_006130.1).

The present invention provides a CD22 specific chimeric antigen receptor (CD22 CAR) comprising:
An extracellular domain comprising:
  a binding domain specific for CD22, preferably a binding domain specific for human CD22, more preferably said binding domain specific for human CD22 is a single-chain variable fragment (scFv),
  a hinge, preferably from CD8 alpha,
  a transmembrane domain, preferably from CD8 alpha, and an intracellular domain comprising: a co-stimulatory signal molecule from human 4-1BB,
and an intracellular signaling domain comprising a human CD3zeta signaling domain.

In a preferred embodiment the CD22 CAR of the invention has no sequence from CD28.

In a preferred embodiment, the CD22 CAR of the invention does not contain any sequence from CD28 and comprises a sequence leader, a TM domain and a hinge from CD8a preferably no sequence from CD28 and comprises a sequence leader of SEQ ID NO: 1, a TM domain of SEQ ID NO: 6 and a hinge of SEQ ID NO: 4 from CD8a.

In one embodiment, the CD22 CAR of the invention comprises a leader sequence from human CD8α (SEQ ID NO: 1) or a leader sequence having at least 95% identity with SEQ ID NO: 1.

In another embodiment, The CD22 CAR of the invention comprises a leader sequence of SEQ ID NO: 2 or a leader sequence having at least 95% identity with SEQ ID NO: 2.

In one embodiment the present invention provides a CD22 specific chimeric antigen receptor (CD22 CAR) comprising:
a binding domain specific for CD22, preferably a binding domain specific for human CD22, more preferably said domain specific for human CD22 is a single-chain variable fragment (scFv), even more preferably comprising a VH and an VL from m971,
a hinge from human CD8 alpha (from CD8α),
a transmembrane domain from human CD8alpha (α),
a co-stimulatory signal molecule from human 4-1BB, and
an intracellular signaling domain comprising a human CD3zeta signaling domain.

In one embodiment the present invention provides a CD22 specific chimeric antigen receptor (CD22 CAR) comprising:
a binding domain specific for CD22, preferably a binding domain specific for human CD22, more preferably said domain specific for human CD22 is a single-chain variable fragment (scFv), even more preferably comprising a VH and an VL from m971,
a hinge from human FcRIIIα,
a transmembrane domain from human CD8alpha(a),
a co-stimulatory signal molecule from human 4-1BB, and
an intracellular signaling domain comprising a human CD3zeta signaling domain.

The present invention also provides a CD22 specific chimeric antigen receptor (CD22 CAR) comprising:
a binding domain specific for CD22, preferably a binding domain specific for human CD22, more preferably said domain specific for human CD22 is a single-chain variable fragment (scFv), even more preferably comprising a VH and an VL from m97,
a hinge from human IgG1,
a transmembrane domain from human CD8alpha(α),
a co-stimulatory signal molecule from human 4-1BB, and
an intracellular signaling domain comprising a human CD3zeta signaling domain.

These three last embodiments encompass a CD22 CAR with a signal peptide of SEQ ID NO: 1 or of SEQ ID NO: 2, preferably of SEQ ID NO: 1.

More preferably, said CD22 CAR has no sequence from CD28.

A scFv of the invention is derived from an antibody specific for CD22, it comprises a VH domain separated to a VL domain by a linker, said VH and/or VL domains contributing to the binding to CD22.

In a preferred embodiment the UCART22 of the invention comprises a scFv from m971 antibody with one GS4 linker between the VH and the VL and 2R between the VL and the CD8alpha hinge.

In the present invention, a scFv is a fusion protein of the variable regions of the heavy ($V_{H\ domain}$) of SEQ ID NO: 12; and light chains ($V_{L\ domain}$) of SEQ ID NO: 13: of an immunoglobulin specific for CD22, m971, connected with a linker peptide, preferably a linker of SEQ ID NO: 10.

In one embodiment said scFv of the invention further comprises a leader sequence (or signal peptide), preferably said leader sequence is linked to the VH domain.

An embodiment wherein said leader sequence is linked to the VL domain is part of the present invention.

In one embodiment, a VH domain is linked to a hinge, in another embodiment a VL domain is linked to said hinge.

The present invention provides a scFv linked to a hinge having different length preferably a hinge from CD8α, IgG1 or FcRIIIα (see, FIG. 2), more preferably from CD8 a.

Preferably, the present invention provides a CD22 CAR comprising: a signal peptide, for example a signal peptide of SEQ ID NO: 2 or from CD8alpha of SEQ ID NO: 1, a (scFv) comprising a VH domain separated from a VL domain by a linker, said VH and VL and linker contributing to the binding to CD22, a hinge from human CD8 alpha chain or a Hinge from human IgG1 or a hinge from FcRIIIα, preferably from CD8 alpha, a transmembrane domain (TM) from CD8alpha(a), a co-stimulatory signal molecule from human 4-1BB, and an intracellular signaling domain comprising the CD3zeta signaling domain.

One of the CD22 CAR of the invention consists in: a leader sequence (for example a CD8a leader sequence or a CD8a signal peptide), an anti-CD22 scFv comprising a VH, a linker, and a VL, or a VL, a linker, and a VH, said VH and VL are derived from m971, a CD8a hinge, a CD8a TM, a co-stimulatory signal molecule from 4-1BB, and an intracellular CD3zeta signaling domain.

One of the CD22 CAR of the invention comprises successively: a CD8a signal peptide, removable upon expression at the cell surface, an epitope recognized by QBEND-10 and an epitope recognized by rituximab, an anti-CD22 scFv comprising a VH, a linker, and a VL, said VH and VL from m971 two successive epitopes recognized by rituximab, a CD8a hinge, a CD8a TM, a co-stimulatory signal molecule from 4-1BB, and an intracellular CD3zeta signaling domain.

One of the CD22 CAR of the invention comprises successively: a CD8a signal peptide, removable upon expression at the cell surface, an epitope recognized by QBEND-10 and an epitope recognized by rituximab, an anti-CD22 scFv comprising a VH, a linker, and a VL, said VH and VL from m971 two successive epitopes recognized by rituximab, a CD8α TM, a co-stimulatory signal molecule from 4-1BB, and an intracellular CD3zeta signaling domain.

One of the CD22 CAR of the invention comprises successively: a CD8α signal peptide, removable upon expression at the cell surface, an anti-CD22 scFv comprising a VH, a linker, and a VL, said VH and VL from m971 two successive epitopes recognized by rituximab, a CD8a hinge, a CD8α TM, a co-stimulatory signal molecule from 4-1BB, and an intracellular CD3zeta signaling domain.

One of the CD22 CAR of the invention comprises successively: a CD8a signal peptide, removable upon expression at the cell surface, an anti-CD22 scFv comprising a VH, a linker, and a VL, said VH and VL from m971 two successive epitopes recognized by rituximab, a CD8a TM, a co-stimulatory signal molecule from 4-1BB, and an intracellular CD3zeta signaling domain.

One of the CD22 CAR of the invention comprises successively: a CD8a signal peptide, removable upon expression at the cell surface, an anti-CD22 scFv comprising a VH, a linker, and a VL, said VH and VL from m971, an anti-CD19 scFv, two successive epitopes recognized by rituximab, a CD8α hinge, a CD8a TM, a co-stimulatory signal molecule from 4-1BB, and an intracellular CD3zeta signaling domain.

One of the CD22 CAR of the invention comprises successively: a CD8α signal peptide, removable upon expression at the cell surface, an anti-CD22 scFv comprising a VH, a linker, and a VL, said VH and VL from m971, an anti-CD19 scFv, two successive epitopes recognized by rituximab, a CD8a TM, a co-stimulatory signal molecule from 4-1BB, and an intracellular CD3zeta signaling domain.

One of the CD22 CAR of the invention comprises successively: a CD8α signal peptide, removable upon expression at the cell surface, an anti-CD19 scFv and an anti-CD22 scFv comprising a VH, a linker, and a VL, said VH and VL from m971, two successive epitopes recognized by rituximab, a CD8α hinge, a CD8α TM, a co-stimulatory signal molecule from 4-1BB, and an intracellular CD3zeta signaling domain.

One of the CD22 CAR of the invention comprises successively: a CD8α signal peptide, removable upon expression at the cell surface, an anti-CD19 scFv and an anti-CD22 scFv comprising a VH, a linker, and a VL, said VH and VL from m971, two successive epitopes recognized by rituximab, a CD8α TM, a co-stimulatory signal molecule from 4-1BB, and an intracellular CD3zeta signaling domain.

Linker-Scfv

A linker according to the invention may be for example, a multimer of the pentapeptide (GGGGS)n (SEQ ID NO: 29) or (G4S)n or (Gly4Ser)n with n=1 to 4, preferably n=3, the 18-mer GGSSRSSSSGGGGSGGGG (SEQ ID NO: 41) (Andris-Widhopf et al., 2011) and the 20-mer (G4S)4 (Schaefer et al., 2010). A linker according to the invention may include sequences with added functionalities, e.g., an epitope tag (Sblattero & Bradbury, 2000 *Nature Biotechnology* 18, 75-80), at least on sequence of SEQ ID NO: 20, preferably 2, separated by a linker, sequences improving scFv properties of the present invention, often in the context of particular antibody sequences.

Amongst other linkers suitable within the present invention is the 15-mer peptide linker (RGRGRGRGRSRGGGS) (SEQ ID NO: 42) (Zhihong Shen, Heping Yan, Ying Zhang, Raymond L. Mernaugh, and Xiangqun Zeng (2008), *Anal Chem.* 80(6): 1910-1917).

In a preferred embodiment, a linker linking the VH to the VL sequence of m971 (or the VL to the VH sequence) is a linker of formula (G4S)n wherein n is 1 to 3; preferably n=3 of sequence (G4S)3 (SEQ ID NO: 10).

In one embodiment the present invention provides a CD22 CAR comprising: a human CD8α leader sequence (CD8α leader or CD8α signal peptide) of SEQ ID NO: 1, an anti-CD22 scFv comprising a VH of SEQ ID NO: 12, a linker of SEQ ID NO: 10, and a VL of SEQ ID NO 13, a human CD8a hinge of SEQ ID NO.4, a human CD8a TM of SEQ ID NO.6, a co-stimulatory signal molecule from 4-1BB of SEQ ID NO.8, and an intracellular CD3zeta signaling domain of SEQ ID NO: 9.

In one embodiment the present invention also provides a CD22 CAR comprising: a human CD8α leader sequence (CD8α leader or CD8α signal peptide) of SEQ ID NO: 1, an anti-CD22 scFv comprising a VH of SEQ ID NO: 12, a linker of SEQ ID N° 10, and a VL of SEQ ID NO 13, a human FcγRIIIα hinge of SEQ ID NO.3, a human CD8α TM of SEQ ID NO.6, a co-stimulatory signal molecule from 4-1BB of SEQ ID NO.8, and an intracellular CD3zeta signaling domain of SEQ ID NO: 9.

In one embodiment, the present invention provides an CD22 CAR comprising a human CD8α leader sequence (CD8α leader or CD8α signal peptide) of SEQ ID NO: 1, an anti-CD22 scFv comprising a VL of SEQ ID NO: 13, a linker of SEQ ID NO: 10, and a VH of SEQ ID NO: 12, a human FcγRIIIα hinge of SEQ ID NO.3, a human CD8α TM of SEQ ID NO.6, a co-stimulatory signal molecule from 4-1BB of SEQ ID NO.8, and an intracellular CD3zeta signaling domain of SEQ ID NO: 9.

In one embodiment, the present invention provides an CD22 CAR comprising a human CD8α leader sequence (CD8α leader or CD8α signal peptide) of SEQ ID NO: 1, an anti-CD22 scFv comprising a VL of SEQ ID NO 13, a linker of SEQ ID N° 10, and a VH of SEQ ID NO: 12, a human CD8α alpha hinge of SEQ ID NO.4, a human CD8α TM of SEQ ID NO.6, a co-stimulatory signal molecule from 4-1BB of SEQ ID NO.8, and an intracellular CD3zeta signaling domain of SEQ ID NO: 9.

In one embodiment, the present invention provides a CD22 specific chimeric antigen receptor (CD22 CAR) comprising:

a signal peptide having an amino acid sequence with at least 80%, more preferably at least 90%, 95%, 97%, 99% or 100% sequence identity with the polypeptide of SEQ ID NO: 1 or 2; preferably the signal peptide has an amino acid sequence with at least 80%, more preferably at least 90%, 95%, 97%, 99% or 100% sequence identity with the polypeptide of SEQ ID NO: 1;

a VH domain separated to a VL domain by a linker, said VH and VL contributing to the binding to CD22; said linker having at least 90%, 95%, 97%, 99% or 100% sequence identity with the polypeptide of SEQ ID NO 10;

Said VH domain having at least 90%, 95% 97%, 99% or 100% sequence identity with the polypeptide of SEQ ID NO 12;

Said VL domain having at least 90%, 95% 97% 99% or 100% sequence identity with the polypeptide of SEQ ID NO 13;

a hinge derived from human CD8 alpha chain having an amino acid sequence with at least 80%, more preferably at least 80%, $^{90}$%, 95% 97%, 99% or 100% sequence identity with the polypeptide of SEQ ID NO: 4;

a transmembrane domain derived from CD8alpha(a) having an amino acid sequence with at least 90%, 91%, 92%, 93%, 94%, 95%, 96%, 97%, 98%, 99% or 100% identity with the polypeptide of SEQ ID NO: 6;

a co-stimulatory signal molecule derived from human 4-1BB (or 4-1BB intracellular domain) having an amino acid sequence with at least 70%, preferably at least 80%, more preferably at least 90%, 95% 97%, 99% or 100% sequence identity with amino acid sequence selected from the group consisting of SEQ ID NO: 8; and an intracellular signaling domain comprising the CD3zeta signaling domain having an amino acid sequence with at least 70%, preferably at least 80%, more preferably at least 90%, 95% 97%, 99% or 100% sequence identity with amino acid sequence selected from the group consisting of SEQ ID NO: 9.

In a preferred embodiment, the CD22 specific chimeric antigen receptor (CD22 CAR) of the present invention does not comprise any sequence from human CD28, in particular from human CD28 intra signaling domain. In a more preferred embodiment, the CD22 specific chimeric antigen receptor (CD22 CAR) of the present invention does not comprise any sequence from human CD28, in particular from human CD28 intra signaling domain and further contains a signal peptide from CD8α, preferably fused to the VH domain of a scFv specific for CD22.

In one embodiment, the present invention provides a CD22 CAR of SEQ ID NO: 15.

In one embodiment, the present invention provides a CD22 CAR having an amino acid sequence with at least 90%, 91%, 92%, 93%, 94%, 95%, 96%, 97%, 98%, 99% or 100% identity with the polypeptide of SEQ ID NO: 15.

In one embodiment the present invention provides a CD22 CAR having a sequence with at least 90%, 91%, 92%, 93%, 94%, 95%, 96%, 97%, 98%, 99% or 100% identity with the polynucleotide of SEQ ID NO: 22.

The CD22 CAR of the invention encompasses the following sequences:

v1-m971 (FcγRIIIα-CD8αTM-41BB.1C-CD3ζ.IC):
(SEQ ID NO: 14)
MALPVTALLLPLALLLHAARPQVQLQQSGPGLVKPSQTLSLTCAISGDSV
SSNSAAWNWIRQSPSRGLEWLGRTYYRSKWYNDYAVSVKSRITINPDTSK
NQFSLQLNSVTPEDTAVYYCAREVTGDLEDAFDIWGQGTMVIVSSGGGGS
GGGGSGGGGSDIQMTQSPSSLSASVGDRVTITCRASQTIWSYLNWYQQRP
GKAPNLLIYAASSLQSGVPSRFSGRGSGTDFTLTISSLQAEDFATYYCQQ
SYSIPQTFGQGTKLEIKGLAVSTISSFFPPGYQIYIWAPLAGTCGVLLLS
LVITLYCKRGRKKLLYIFKQPFMRPVQTTQEEDGCSCRFPEEEEGGCELR
VKFSRSADAPAYQQGQNQLYNELNLGRREEYDVLDKRRGRDPEMGGKPRR
KNPQEGLYNELQKDKMAEAYSEIGMKGERRRGKGHDGLYQGLSTATKDTY
DALHMQALPPR.

V3-m971 (CD8α-CD8αTM-41BB.IC-CD3ζ.IC):
(SEQ ID NO: 15)
MALPVTALLLPLALLLHAARPQVQLQQSGPGLVKPSQTLSLTCAISGDSV
SSNSAAWNWIRQSPSRGLEWLGRTYYRSKWYNDYAVSVKSRITINPDTSK
NQFSLQLNSVTPEDTAVYYCAREVTGDLEDAFDIWGQGTMVIVSSGGGGS
GGGGSGGGGSDIQMTQSPSSLSASVGDRVTITCRASQTIWSYLNWYQQRP
GKAPNLLIYAASSLQSGVPSRFSGRGSGTDFTLTISSLQAEDFATYYCQQ
SYSIPQTFGQGTKLEIKTTTPAPRPPTPAPTIASQPLSLRPEACRPAAGG
AVHTRGLDFACDIYIWAPLAGTCGVLLLSLVITLYCKRGRKKLLYIFKQP
FMRPVQTTQEEDGCSCRFPEEEEGGCELRVKFSRSADAPAYQQGQNQLYN
ELNLGRREEYDVLDKRRGRDPEMGGKPRRKNPQEGLYNELQKDKMAEAYS
EIGMKGERRRGKGHDGLYQGLSTATKDTYDALHMQALPPR.

In a preferred embodiment the CD22 CAR of the invention comprises the following sequence:

(SEQ ID NO: 15)
MALPVTALLLPLALLLHAARPQVQLQQSGPGLVKPSQTLSLTCAISGDSV
SSNSAAWNWIRQSPSRGLEWLGRTYYRSKWYNDYAVSVKSRITINPDTSK
NQFSLQLNSVTPEDTAVYYCAREVTGDLEDAFDIWGQGTMVIVSSGGGGS
GGGGSGGGGSDIQMTQSPSSLSASVGDRVTITCRASQTIWSYLNWYQQRP
GKAPNLLIYAASSLQSGVPSRFSGRGSGTDFTLTISSLQAEDFATYYCQQ
SYSIPQTFGQGTKLEIKTTTPAPRPPTPAPTIASQPLSLRPEACRPAAGG
AVHTRGLDFACDIYIWAPLAGTCGVLLLSLVITLYCKRGRKKLLYIFKQP
FMRPVQTTQEEDGCSCRFPEEEEGGCELRVKFSRSADAPAYQQGQNQLYN
ELNLGRREEYDVLDKRRGRDPEMGGKPRRKNPQEGLYNELQKDKMAEAYS
EIGMKGERRRGKGHDGLYQGLSTATKDTYDALHMQALPPR.

Sequences of CD22 CAR with a peptide signal from SEQ ID NO.2, a TM domain from CD8α and a linker between the VH and VL domain:

(SEQ ID NO: 61)
METDTLLLWVLLLWVPGSTGEVQLVQSGGGVVRPGGSLRLPCAASGFTFDDYGMSWVRQAPGK
GLEWVSGINWNGGSTGYADSVKGRFTISRDNAKNSLYLQMNSLRAEDTALYHCARGGDDAFDIW
GQGTMVTVSSGGGGSGGGGSGGGGSRIVMTQSPGTLSVSPGETATLSCRASQSFSNMLAWYQQ
KSGQPPRLLIYGVSTRAAGVPARFSGSGSGTEFTLTISNLQSEDFAVYYCQQYGDWPRYTFGQGTKV
ERKGLAVSTISSFFPPGYQIYIWAPLAGTCGVLLLSLVITLYCKRGRKKLLYIFKQPFMRPVQTTQEEDG
CSCRFPEEEEGGCELRVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDTYDALHMQALPPR.

(SEQ ID NO: 62)
METDTLLLWVLLLWVPGSTGEVQLVQSGGGVVRPGGSLRLPCAASGFTFDDYGMSWVRQAPGK
GLEWVSGINWNGGSTGYADSVKGRFTISRDNAKNSLYLQMNSLRAEDTALYHCARGGDDAFDIW
GQGTMVTVSSGGGGSGGGGSGGGGSRIVMTQSPGTLSVSPGETATLSCRASQSFSNMLAWYQQ
KSGQPPRLLIYGVSTRAAGVPARFSGSGSGTEFTLTISNLQSEDFAVYYCQQYGDWPRYTFGQGTKV
ERKTTTPAPRPPTPAPTIASQPLSLRPEACRPAAGGAVHTRGLDFACDIYIWAPLAGTCGVLLLSLVIT

-continued

LYCKRGRKKLLYIFKQPFMRPVQTTQEEDGCSCRFPEEEEGGCELRVKFSRSADAPAYQQGQNQLY

NELNLGRREEYDVLDKRRGRDPEMGGKPRRKNPQEGLYNELQKDKMAEAYSEIGMKGERRRGKG

HDGLYQGLSTATKDTYDALHMQALPPR

M971 V1:
(SEQ ID NO: 63)
METDTLLLWVLLLWVPGSTGQVQLQQSGPGLVKPSQTLSLTCAISGDSVSSNSAAWNWIRQSPSR

GLEWLGRTYYRSKWYNDYAVSVKSRITINPDTSKNQFSLQLNSVTPEDTAVYYCAREVTGDLEDAFD

IWGQGTMVTVSSGGGGSGGGGSGGGGSDIQMTQSPSSLSASVGDRVTITCRASQTIWSYLNWYQ

QRPGKAPNLLIYAASSLQSGVPSRFSGRGSGTDFTLTISSLQAEDFATYYCQQSYSIPQTFGQGTKLEI

KGLAVSTISSFFPPGYQIYIWAPLAGTCGVLLLSLVITLYCKRGRKKLLYIFKQPFMRPVQTTQEEDGCS

CRFPEEEEGGCELRVKFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYDALHMQALPPR.

M971 V3:
(SEQ ID NO: 64)
METDTLLLWVLLLWVPGSTGQVQLQQSGPGLVKPSQTLSLTCAISGDSVSSNSAAWNWIRQSPSR

GLEWLGRTYYRSKWYNDYAVSVKSRITINPDTSKNQFSLQLNSVTPEDTAVYYCAREVTGDLEDAFD

IWGQGTMVIVSSGGGGSGGGGSGGGGSDIQMTQSPSSLSASVGDRVTITCRASQTIWSYLNWYQ

QRPGKAPNLLIYAASSLQSGVPSRFSGRGSGTDFTLTISSLQAEDFATYYCQQSYSIPQTFGQGTKLEI

KTTTPAPRPPTPAPTIASQPLSLRPEACRPAAGGAVHTRGLDFACDIYIWAPLAGTCGVLLLSLVITLY

CKRGRKKLLYIFKQPFMRPVQTTQEEDGCSCRFPEEEEGGCELRVKFSRSADAPAYQQGQNQLYNE

LNLGRREEYDVLDKRRGRDPEMGGKPRRKNPQEGLYNELQKDKMAEAYSEIGMKGERRRGKGHD

GLYQGLSTATKDTYDALHMQALPPR.

In one embodiment the present invention provides the following sequences:
QVQLQQSGPGLVKPSQTLSLTCAISGDSVSSN-SAAWNWIRQSPSRGLEWLGRTYYRS KWYN-DYAVSVKSRITINPDTSKNQFSLQLNSVTPED-TAVYYCAREVTGDLEDAFDIWGQGT MVTVSS GGGGSGGGGSGGGGSDIQMTQSPSSLSASVGDR VTITCRASQTIWSYLNWYQQRP GKAPNLLI-YAASSLQ SGVPSRFSGRGSGTDFTLTISSLQAED-FATYYCQQSYSIPQTFGQGTK LEIKTTTPAPRP PTPAPTIASQPLSLRPEACRPAAGGAVHTRGLD-FACDIYIWAPLAGTCGVL LLSLVITLYCKRGRK KLLYIFKQPFMRPVQTTQEEDGCSCRFPEEEE GGCELRVKFSRSADAP AYQQGQNQLYNELNL-GRREEYDVLDKRRGRDPEMGGKPRRKNPQEG-LYNELQKDKMAE AYSEIGMKGERRRGKGHDG-LYQGLSTATKDTYDALHMQALPPR (SEQ ID NO: 65). In this CD22CAR the signal peptide is absent.

In one embodiment, the UCART22 of the present invention comprises a sequence of SEQ ID NO: 20:

(SEQ ID NO: 20)
ATGGCTCTGCCCGTCACCGCTCTGCTGCTGCCACTGGCCCTGCTGCTGCAC

GCAGCAAGACCACAGGTGCAGCTGCAGCAGAGCGGCCCTGGCCTGGTGAAG

CCAAGCCAGACACTGTCCCTGACCTGCGCCATCAGCGGCGATTCCGTGAGC

TCCAACTCCGCCGCCTGGAATTGGATCAGGCAGTCCCCTTCTCGGGGCCTG

GAGTGGCTGGGAAGGACATACTATCGGTCTAAGTGGTACAACGATTATGCC

GTGTCTGTGAAGAGCAGAATCACAATCAACCCTGACACCTCCAAGAATCAG

TTCTCTCTGCAGCTGAATAGCGTGACACCAGAGGACACCGCCGTGTACTAT

TGCGCCAGGGAGGTGACCGGCGACCTGGAGGATGCCTTTGACATCTGGGGC

CAGGGCACAATGGTGACCGTGTCTAGCGGAGGAGGAGGATCCGGAGGAGGA

GGATCTGGCGGCGGCGGCAGCGATATCCAGATG.

In one embodiment, the UCART22 of the present invention comprises a sequence of SEQ ID NO: 22.

In a preferred embodiment, the UCART22 of the present invention comprises a sequence of SEQ ID NO: 22 inserted into a human TRAC gene (such as in human TRAC gene Chromosome 14-NC_000014.9) and expresses at the cell surface an anti-CD22 CAR specific for the proximal part of CD22.

In a more preferred embodiment, the UCART22 of the present invention comprises a sequence of SEQ ID NO: 20 inserted into a human TRAC gene (such as in human TRAC gene Chromosome 14-NC_000014.9) and expresses at the cell surface an anti-CD22 CAR specific for the distal part of CD22.

In one aspect, an anti-CD22 binding domain of the CD22 CAR of the invention is an anti-CD22 binding domain specific for the distal portion of CD22.

Ha22-Car

Accordingly the present invention provides a CD22 CAR with the following sequence:

(SEQ ID NO: 23)
MALPVTALLLPLALLLHAARPEVQLVESGGGLVKPGGSLKLSCAASGFAFS

IYDMSWVRQTPEKRLEWVAYISSGGGTYYPDTVKGRFTISRDNAKNTLYLQ

MSSLKSEDTAMYYCARHSGYGTHWGVLFAYWGQGTLVTVSAGGGGSGGGGS

GGGGSDIQMTQTTSSLSASLGDRVTISCRASQDISNYLNWYQQKPDGTVKL

LIYYTSILHSGVPSRFSGSGSGTDYSLTISNLEQEDFATYFCQQGNTLPWT

FGGGTKLEIKATTTPAPRPPTPAPTIASQPLSLRPEACRPAAGGAVHTRGL

DFACDIYIWAPLAGTCGVLLLSLVITLYCKRGRKKLLYIFKQPFMRPVQTT

QEEDGCSCRFPEEEEGGCELRVKFSRSADAPAYQQGQNQLYNELNLGRREE

YDVLDKRRGRDPEMGGKPRRKNPQEGLYNELQKDKMAEAYSEIGMKGERRR

GKGHDGLYQGLSTATKDTYDALHMQALPPR.

Preferably the UCART22 of the present invention comprises a sequence:

(SEQ ID NO: 24)
ATGGCTCTGCCCGTCACCGCTCTGCTGCTGCCACTGGCCCTGCTGCTGCAC

GCAGCAAGGCCTGAGGTGCAGCTGGTGGAATCCGGAGGAGGCCTGGTGAAG

CCTGGCGGCTCTCTGAAGCTGAGCTGTGCCGCCTCCGGCTTCGCCTTTTCC

ATCTACGACATGTCTTGGGTGAGGCAGACCCCAGAGAAGCGCCTGGAGTGG

GTGGCCTATATCAGCTCCGGCGGCGGCACCTACTATCCCGACACAGTGAAG

GGCCGGTTCACCATCTCTAGAGATAACGCCAAGAATACACTGTACCTGCAG

ATGTCTAGCCTGAAGAGCGAGGATACCGCCATGTACTATTGCGCAAGGCAC

TCCGGATACGGAACACACTGGGCGTGCTGTTTGCCTATTGGGGCCAGGGC

ACCCTGGTGACAGTGAGCGCCGGAGGAGGAGGAAGCGGCGGAGGAGGCTCC

GGCGGCGGCGGCTCTGACATCCAGATGACCCAGACCCATCCTCTCTGAGC

GCCTCCCTGGGCGACAGGGTGACAATCTCTTGTAGAGCCAGCCAGGATATC

TCCAACTACCTGAATTGGTATCAGCAGAAGCCTGATGGCACCGTGAAGCTG

CTGATCTACTATACATCTATCCTGCACAGCGGAGTGCCATCCCGGTTCTCT

GGAAGCGGATCCGGAACCGACTACTCTCTGACAATCAGCAACCTGGAGCAG

GAGGATTTCGCCACCTATTTTTGCCAGCAGGGCAATACCCTGCCTTGGACA

TTTGGCGGCGGCACAAAGCTGGAGATCAAGGCCACCACAACCCCTGCACCA

AGGCCACCAACACCAGCACCTACCATCGCATCTCAGCCTCTGAGCCTGAGA

CCAGAGGCATGTAGGCCAGCAGCAGGAGGAGCAGTGCACACAAGGGGACTG

GATTTTGCCTGTGATATCTACATCTGGGCACCTCTGGCAGGAACATGTGGC

GTGCTCCTGCTCAGCCTGGTCATCACCCTGTACTGCAAGAGAGGCAGGAAG

AAGCTGCTGTATATCTTCAAGCAGCCCTTCATGAGACCCGTGCAGACAACC

CAGGAGGAGGACGGCTGCTCCTGTAGGTTCCCAGAAGAGGAGGAGGGAGGA

TGTGAGCTGCGCGTGAAGTTTTCCCGGTCTGCCGATGCACCTGCATACCAG

CAGGGACAGAATCAGCTGTATAACGAGCTGAATCTGGGCCGGAGAGAGGAG

TACGACGTGCTGGATAAGAGGAGGGGAAGGGACCCAGAGATGGGAGGCAAG

CCTCGGAGAAAGAACCCACAGGAGGGCCTGTACAATGAGCTGCAGAAGGAC

AAGATGGCCGAGGCCTATTCTGAGATCGGCATGAAGGGAGAGAGGCGCCGG

-continued
GGCAAGGGACACGATGGCCTGTACCAGGGCCTGTCCACAGCCACCAAGGAC

ACCTATGATGCCCTGCATATGCAGGCACTGCCTCCAAGGTGA.

An anti-CD22 binding domain specific for the distal portion of CD22 may be expressed alone or with an anti-CD22 binding domain specific for the proximal portion of CD22 in the UCART22 of the invention.

In one aspect, the anti-CD22 binding domain of the CD22 CAR of the invention is an optimized anti-CD22 binding domain.

As used herein, "optimized" antibody (or scFv) refers to forms of antibodies (or scFv) that are chimeric immunoglobulins, immunoglobulin chains, or fragments thereof (such as Fv, Fab, Fab', F(ab')$_2$ or other antigen binding subsequences of antibodies) that contain minimal sequences derived from immunoglobulin. Preferably, antibodies are human immunoglobulins (recipient antibody) in which residues from a complementary determining region (CDR) are replaced by residues from a CDR to achieve the desired specificity, affinity, and capacity.

The donor CDR may undergo few amino acid changes that may significantly affect or alter the binding characteristics of the CD22 CAR of the invention. Indeed, one of the invention provided here is a CD22 CAR which binding to CD22-expressing cell (and cytolytic activity) is maintained but the affinity is modified to reduce the intensity of the response (cytokine release).

Amino acid modifications are usually conservative modifications including amino acid substitutions, additions and deletions in said antibody fragment in said CAR and/or any of the other parts of said CAR molecule. Modifications can be introduced into an antibody, into an antibody fragment or in any of the other parts of the CAR molecule of the invention by standard techniques known in the art, such as site-directed mutagenesis, PCR-mediated mutagenesis or by employing optimized germline sequences.

In general, the optimized CAR will comprise substantially all of at least one, and typically two, variable domains, in which all or substantially all of the CDR regions correspond to the original human immunoglobulin.

Conservative amino acid substitutions mean substitutions in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested using the functional assays described herein.

In a preferred embodiment, the present invention provides a CD22 CAR having conservative sequence modifications (or an amino acid sequence change) as compared to the amino acid sequence of the polypeptide of SEQ ID NO: 15.

In a preferred embodiment, the present invention provides a CD22 CAR having an amino acid sequence with 2 amino acid changes as compared to the amino acid sequence of the polypeptide of SEQ ID NO: 15.

In a preferred embodiment, the present invention provides a CD22 CAR having an amino acid sequence with 3 amino acid changes as compared to the amino acid sequence of the polypeptide of SEQ ID NO: 15.

In a preferred embodiment, the present invention provides a CD22 CAR having an amino acid sequence with 4 amino acid changes as compared to the amino acid sequence of the polypeptide of SEQ ID NO: 15.

In a preferred embodiment, the present invention provides a CD22 CAR having an amino acid sequence with 5 amino acid changes as compared to the amino acid sequence of the polypeptide of SEQ ID NO: 15, optionally comprising at least one sequence of SEQ ID NO 20.

In a more preferred embodiment, the present invention provides a CD22 CAR having an amino acid sequence with 5 amino acid changes as compared to the amino acid sequence of the polypeptide of SEQ ID N° 15 and at least one CDR in SEQ ID NO: 15 is conserved.

In a more preferred embodiment, the present invention provides a CD22 CAR having an amino acid sequence with from 1 to 15 amino acid changes as compared to the amino acid sequence of the polypeptide of SEQ ID NO: 15 and at least one CDR in SEQ ID NO: 15, is conserved.

In a preferred embodiment, the sequence of CD22 CAR of the invention is modified by changing 1, 2, 3, 4, 5, 6, 7, 8, 9 or 10 amino acids as compared to the wt CD22 CAR, to reduce the HAMA (human anti-mouse response), without affecting the binding capacity of said CAR to its target (CD22).

In a preferred embodiment, the present invention provides a CD22 CAR having an amino acid sequence with at least 1 amino acid change as compared to the amino acid sequence of wt (wt is m971) said at least 1 amino acid change having no impact or improving the binding and/or activity of said CD22 CAR in primary T cells.

Binding characteristics may be modified using adapted technique initially described in Mitchell Ho, Satoshi Nagata, and Ira Pastan. Isolation of anti-CD22 Fv with high affinity by Fv display on human cells *PNAS* 2006 103 (25) 9637-9642; published ahead of print Jun. 8, 2006, doi:10.1073/pnas.0603653103 which is incorporated herein by reference.

Those optimized scFv also bear at least one mutations equivalent to mutations Pro-91-Thr-92 (PT) Gly-91-Ala-92 and Val-91-Phe-92.

In one embodiment the present invention provides an anti CD22 CAR comprising:
an extracellular domain comprising:
a signal peptide,
a ligand binding-domain optionally optimized comprising a VH domain and a VL
domain from a monoclonal anti-CD22 antibody having one of the following Pro-91-Thr-92 (PT), Gly-91-Ala-92, Val-91-Phe-92, mutations or equivalent,
a hinge, comprising a CD8 alpha (a) hinge,
a CD8 alpha transmembrane domain, and
a cytoplasmic domain comprising a CD3 zeta signaling domain and a co-stimulatory domain from 4-1BB.

In a preferred embodiment the present invention provides an anti CD22 CAR as above wherein said monoclonal anti-CD22 antibody is from m971 antibody with hots spot in CDRs. Preferably, one of the following Pro-91-Thr-92 (PT), Gly-91-Ala-92, Val-91-Phe-92, mutations.

In a more preferred embodiment, the present invention provides an isolated engineered (TCR and dCK KO) immune T cell comprising an anti CD22 CAR comprising:
An extracellular domain comprising: a signal peptide, a ligand binding-domain comprising a VH domain and a VL domain from a monoclonal anti-CD22 antibody having at least one of the following Pro-91-Thr-92, Gly-91-Ala-92 mutation; Val-91-Phe-92 mutation,
a hinge, comprising a CD8 alpha (α) hinge,
a CD8 alpha transmembrane domain, and
a cytoplasmic domain comprising a CD3 zeta signaling domain and a co-stimulatory domain from 4-1BB.

In a more preferred embodiment, the present invention provides an isolated engineered (TCR and CD52 KO) immune T cell comprising an anti CD22 CAR comprising:
An extracellular domain comprising, a signal peptide, a ligand binding-domain comprising a VH domain and a VL domain from a monoclonal anti-CD22 antibody having at least one of the following Pro-91-Thr-92, Gly-91-Ala-92 mutation; Val-91-Phe-92 mutation,
a hinge, comprising a CD8 alpha (a) hinge,
a CD8 alpha transmembrane domain, and
a cytoplasmic domain comprising a CD3 zeta signaling domain and a co-stimulatory domain from 4-1BB.

In a more preferred embodiment, the present invention provides an isolated engineered (TCR, CD52 and dCK KO) immune T cell comprising an anti CD22 CAR comprising:
An extracellular domain comprising, a signal peptide, a ligand binding-domain comprising a VH domain and a VL domain from a monoclonal anti-CD22 antibody having at least one of the following Pro-91-Thr-92, Gly-91-Ala-92 mutation; Val-91-Phe-92 mutation,
a hinge, comprising a CD8 alpha (a) hinge,
a CD8 alpha transmembrane domain, and
a cytoplasmic domain comprising a CD3 zeta signaling domain and a co-stimulatory domain from 4-1BB.

In one aspect, the CAR 22 may be co-expressed at the cell surface with at least one, preferably two, more preferably three, monoclonal antibody (mAb)-specific epitopes, said mAb-specific epitope may be fused to a transmembrane domain of CD8. In one embodiment said mAb—specific epitope is an epitope recognized by rituximab, and/or from QBEND-10 and the peptide co-expressed with the cD22 CAR is RQR8.

In another embodiment, at least one, preferably two, more preferably three, monoclonal antibody (mAb)-specific epitopes, may be inserted into the linker L of the scFv (binding the VH to the VL) specific for CD22 and/or into the hinge of the CD22 CAR.

Molecular antibody (mAb)-specific epitope, may be one of the following a mAb-specific epitope specifically recognized by an monoclonal antibody selected from the group consisting of ibritumomab, tiuxetan, muromonab-CD3, tositumomab, abciximab, basiliximab, brentuximab vedotin, cetuximab, infliximab, rituximab, alemtuzumab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and ustekinumab, preferably from rituximab (R) and/or from QBEND-10 (Q).

The epitope-specific mAb may be used for in vitro cell sorting and/or in vivo cell depletion of immune cells expressing a CD22.

In particular embodiments, the extracellular binding domain of the CD22 CAR of the invention may comprises one of the following sequences:
$V_1$-$L_1$-$V_2$-$(L)_x$-Epitope1-$(L)_x$-;
$V_1$-$L_1$-$V_2$-$(L)_x$-Epitope1-$(L)_x$-Epitope2-$(L)_x$-;
$V_1$-$L_1$-$V_2$-$(L)_x$-Epitope1-$(L)_x$-Epitope2-$(L)_x$-Epitope3-$(L)_x$-;

$(L)_x$-Epitope1-$(L)_x$-$V_1$-$L_1$-$V_2$;
$(L)_x$-Epitope1-$(L)_x$-Epitope2-$(L)_x$-$V_1$-$L_1$-$V_2$;
Epitope1-$(L)_x$-Epitope2-$(L)_x$-Epitope3-$(L)_x$-$V_1$-$L_1$-$V_2$;
$(L)_x$-Epitope1-$(L)_x$-$V_1$-$L_1$-$V_2$-$(L)_x$-Epitope2-$(L)_x$;
$(L)_x$-Epitope1-$(L)_x$-$V_1$-$L_1$-$V_2$-$(L)_x$-Epitope2-$(L)_x$-Epitope3-$(L)_x$-;
$(L)_x$-Epitope1-$(L)_x$-$V_1$-$L_1$-$V_2$-$(L)_x$-Epitope2-$(L)_x$-Epitope3-$(L)_x$-Epitope4-$(L)_x$-;
$(L)_x$-Epitope1-$(L)_x$-Epitope2-$(L)_x$-$V_1$-$L_1$-$V_2$-$(L)_x$-Epitope3-$(L)_x$-;
$(L)_x$-Epitope1-$(L)_x$-Epitope2-$(L)_x$-$V_1$-$L_1$-$V_2$-$(L)_x$-Epitope3-$(L)_x$-Epitope4-$(L)_x$-;
$V_1$-$(L)_x$-Epitope1-$(L)_x$-$V_2$;
$V_1$-$(L)_x$-Epitope1-$(L)_x$-$V_2$-$(L)_x$-Epitope2-$(L)_x$;
$V_1$-$(L)_x$-Epitope1-$(L)_x$-$V_2$-$(L)_x$-Epitope2-$(L)_x$-Epitope3-$(L)_x$;
$V_1$-$(L)_x$-Epitope1-$(L)_x$-$V_2$-$(L)_x$-Epitope2-$(L)_x$-Epitope3-$(L)_x$-Epitope4-$(L)_x$;
$(L)_x$-Epitope1-$(L)_x$-$V_1$-$(L)_x$-Epitope2-$(L)_x$-$V_2$; or,
$(L)_x$-Epitope1-$(L)_x$-$V_1$-$(L)_x$-Epitope2-$(L)_x$-$V_2$-$(L)_x$-Epitope3-$(L)_x$;
wherein, V1 is VL, preferably of SEQ ID NO: 12 and V2 is VH, preferably of SEQ ID NO: 13 or V1 is VH and V2 is VL;

L1 is a linker suitable to link the VH chain to the VL chain; preferably of SEQ ID NO: 10;

L is a linker comprising glycine and serine residues, and each occurrence of L in the extracellular binding domain can be identical or different to other occurrence of L in the same extracellular binding domain, and, x is 0 or 1 and each occurrence of x is selected independently from the others; and Epitope 1, Epitope 2 and Epitope 3 are mAb-specific epitopes and can be identical or different.

In one embodiment, the extracellular binding domain comprises one of the following sequences $V_1$-$L_1$-$V_2$-L-Epitope1; $V_1$-$L_1$-$V_2$-L-Epitope1-L; $V_1$-$L_1$-$V_2$-L-Epitope1-L-Epitope2; $V_1$-$L_1$-$V_2$-L-Epitope1-L-Epitope2-L; $V_1$-$L_1$-$V_2$-L-Epitope1-L-Epitope2-L-Epitope3; $V_1$-$L_1$-$V_2$-L-Epitope1-L-Epitope2-L-Epitope3-L; $V_1$-$L_1$-$V_2$-Epitope1; $V_1$-$L_1$-$V_2$-Epitope1-L; $V_1$-$L_1$-$V_2$-Epitope1-L-Epitope2; $V_1$-$L_1$-$V_2$-Epitope1-L-Epitope2-L; $V_1$-$L_1$-$V_2$-Epitope1-L-Epitope2-L-Epitope3; $V_1$-$L_1$-$V_2$-Epitope1-L-Epitope2-L-Epitope3-L; Epitope1-$V_1$-$L_1$-$V_2$; Epitope1-L-$V_1$-$L_1$-$V_2$; L-Epitope1-$V_1$-$L_1$-$V_2$; L-Epitope1-L-$V_1$-$L_1$-$V_2$; Epitope1-L-Epitope2-$V_1$-$L_1$-$V_2$; Epitope1-L-Epitope2-L-$V_1$-$L_1$-$V_2$; L-Epitope1-L-Epitope2-$V_1$-$L_1$-$V_2$; L-Epitope1-L-Epitope2-L-$V_1$-$L_1$-$V_2$; Epitope1-L-Epitope2-L-Epitope3-$V_1$-$L_1$-$V_2$; Epitope1-L-Epitope2-L-Epitope3-L-$V_1$-$L_1$-$V_2$; L-Epitope1-L-Epitope2-L-Epitope3-$V_1$-$L_1$-$V_2$; L-Epitope1-L-Epitope2-L-Epitope3-L-$V_1$-$L_1$-$V_2$; $V_1$-L-Epitope1-L-$V_2$; L-Epitope1-L-$V_1$-L-Epitope2-L-$V_2$; $V_1$-L-Epitope1-L-$V_2$-L-Epitope2-L; $V_1$-L-Epitope1-L-$V_2$-L-Epitope2-L-Epitope3; $V_1$-L-Epitope1-L-$V_2$-L-Epitope2-Epitope3; $V_1$-L-Epitope1-L-$V_2$-L-Epitope2-L-Epitope3-Epitope4; L-Epitope1-L-$V_1$-L-Epitope2-L-$V_2$-L-Epitope3-L; L-Epitope1-L-$V_1$-L-Epitope2-L-$V_2$-L-Epitope3-L; L-Epitope1-L-$V_1$-L-Epitope2-L-$V_2$-L-Epitope3; L-Epitope1-L-$V_1$-$L_1$-$V_2$-L-Epitope2-L; L-Epitope1-L-$V_1$-$L_1$-$V_2$-L-Epitope2-L-Epitope3; L-Epitope1-L-$V_1$-$L_1$-$V_2$-L-Epitope2-Epitope3, or Epitope1-L-$V_1$-$L_1$-$V_2$-L-Epitope2-L-Epitope3-Epitope4 wherein:

$V_1$ is $V_L$ and $V_2$ is $V_H$ or $V_1$ is $V_H$ and $V_2$ is $V_L$; and VH, and VL are optimized VH and VL from m971.

$L_1$ is any linker suitable to link the $V_H$ chain to the $V_L$ chain;

L is a linker comprising glycine and serine residues, and each occurrence of L in the extracellular binding domain can be identical or different to other occurrences of L in the same extracellular binding domain, and, Epitope 1, Epitope 2 and Epitope 3 are mAb-specific epitopes and can be identical or different.

$L_1$ is a linker comprising Glycine and/or Serine, preferably, $L_1$ is a linker comprising the amino acid sequence (Gly-Gly-Gly-Ser)n (SEQ ID NO: 56) or (Gly-Gly-Gly-Gly-Ser)n, (SEQ ID NO: 57) where n is 1, 2, 3, 4 or 5 or a linker comprising the amino acid sequence $(Gly_4Ser)_4$ (SEQ ID NO: 58) or $(Gly_4Ser)_3$ (SEQ ID NO: 59). Similarly, L is a linker comprising Glycine and/or Serine, preferably L is a linker having an amino acid sequence selected from SGG, GGS, SGGS (SEQ ID NO: 43), SSGGS (SEQ ID NO: 44), GGGG (SEQ ID NO: 45), SGGGG (SEQ ID NO: 46), GGGGS (SEQ ID NO: 29), SGGGGS (SEQ ID NO: 47), GGGGGS (SEQ ID NO: 48), SGGGGGS (SEQ ID NO: 49), SGGGGG (SEQ ID NO: 50), GSGGGGS (SEQ ID NO: 51), GGGGGGGS (SEQ ID NO: 52), SGGGGGGG (SEQ ID NO: 53), SGGGGGGGS (SEQ ID NO: 54), and SGGGGSGGGGS (SEQ ID NO: 55), preferably L is a SGGGG (SEQ ID NO: 46), GGGGS (SEQ ID NO: 29) or SGGGGS (SEQ ID NO: 47).

In a preferred embodiment, Epitope 1, Epitope 2, Epitope 3 and Epitope 4 are independently selected from mAb-specific epitopes specifically recognized by ibritumomab, tiuxetan, muromonab-CD3, tositumomab, abciximab, basiliximab, brentuximab vedotin, cetuximab, infliximab, rituximab, alemtuzumab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and ustekinumab, preferably Epitope 1, Epitope 2, Epitope 3 and Epitope 4 are recognized by rituximab or QBEND-10.

Epitope 1, Epitope 2, Epitope 3 and Epitope 4 are mAb-specific epitopes specifically recognized by the antibodies indicated below in Table 6.

TABLE 6

| Antibody | Indication | Drug bank accession no (or other no if stated) | Target/ Antigen |
|---|---|---|---|
| Ibritumomab tiuxetan | Non-Hodgkin lymphoma (with yttrium-90 or indium-111) | DB00078 | CD20 |
| Muromonab-CD3 | Transplant rejection | DB00075 | T cell CD3 Receptor |
| Tositumomab | Non-Hodgkin lymphoma | DB00081 | CD20 |
| Abciximab | Cardiovascular disease | DB00054 | inhibition of glycoprotein IIb/IIIa |
| Basiliximab | Transplant rejection | DB00074 | IL-2Rα receptor (CD25) |
| Brentuximab vedotin | Anaplastic large cell lymphoma | DB08870 | CD30 |
| Cetuximab | Colorectal cancer, Head and neck cancer | DB00002 | epidermal growth factor receptor |
| Infliximab | Several autoimmune disorders | DB00065 | inhibition of TNF-α signaling |

TABLE 6-continued

| Antibody | Indication | Drug bank accession no (or other no if stated) | Target/Antigen |
|---|---|---|---|
| Rituximab | Non-Hodgkin lymphoma | DB00073 | CD20 |
| Alemtuzumab | Chronic lymphocytic leukemia | DB00087 | CD52 |
| Bevacizumab | Colorectal cancer, Age related macular degeneration (off-label) | DB00112 | Vascular endothelial growth factor (VEGF) |
| Certolizumab pegol | Crohn's disease | DB08904 | inhibition of TNF-α signaling |
| Daclizumab | Transplant rejection | DB00111 | IL-2Rα receptor (CD25) |
| Eculizumab | Paroxysmal nocturnal hemoglobinuria | DB01257 | Complement system protein |
| Efalizumab | Psoriasis | DB00095 | CD11a |
| Gemtuzumab | Acute myelogenous leukemia (with calicheamicin) | DB00056 | CD33 |
| Natalizumab | Multiple sclerosis and Crohn's disease | DB00108 | alpha-4 (α4) integrin |
| Omalizumab | mainly allergy-related asthma | DB00043 | immunoglobulin E (IgE) |
| Palivizumab | Respiratory Syncytial Virus | DB00110 | an epitope of the RSV F protein |
| Ranibizumab | Macular degeneration | DB01270 | Vascular endothelial growth factor A (VEGF-A) |
| Tocilizumab (or Atlizumab) | Rheumatoid arthritis | DB06273 | Anti-IL-6R |
| Trastuzumab | Breast cancer | DB00072 | ErbB2 |
| Vedolizumab | Crohn's disease, ulcerative colitis | CAS no 943609-66-3 | integrin α4β7 |
| Adalimumab | Several auto-immune disorders | DB00051 | inhibition of TNF-α signaling |
| Belimumab | Systemic lupus erythematosus | DB08879 | inihibition of B-cell activating factor |
| Canakinumab | Cryopyrin-associated periodic syndrome (CAPS) | DB06168 | IL-1β |
| Denosumab | Postmenopausal osteoporosis, Solid tumor's bony metastases | DB06643 | RANK Ligand inhibitor |
| Golimumab | Rheumatoid arthritis, Psoriatic arthritis, and Ankylosing spondylitis | DB06674 | TNF-alpha inihibitor |
| Ipilimumab (MDX-101) | Melanoma | DB06186 | blocks CTLA-4 |
| Ofatumumab | Chronic lymphocytic leukemia | CAS no 679818-59-8 | CD20 |
| Panitumumab | Colorectal cancer | DB01269 | epidermal growth factor receptor |
| Ustekinumab | Psoriatic Arthritis, Plaque Psoriasis | DB05679 | IL-12, IL-23 |
| Nivolumab | renal cell carcinoma, lung cancer, melanoma, and advanced or metastatic solid tumors | CAS no 946414-94-4 | PD-1 |

The mAb-specific epitope may therefore comprise one polypeptide selected from:

```
                                       (SEQ ID NO: 19)
CPYSNPSLC, (SEQ ID NO: 30)
NSELLSLINDMPITNDQKKLMSNN, (SEQ ID NO: 31)
CQFDLSTRRLKC, (SEQ ID NO: 32)
CQYNLSSRALKC, (SEQ ID NO: 33)
CVWQRWQKSYVC, (SEQ ID NO: 34)
CVWQRWQKSYVC, (SEQ ID NO: 35)
SFVLNWYRMSPSNQTDKLAAFPEDR, (SEQ ID NO: 36)
SGTYLCGAISLAPKAQIKE, (SEQ ID NO: 37)
ELPTQGTFSNVSTNVSPAKPTTTA, (SEQ ID NO: 38)
GQNDTSQTSSPS.
```

Table 7 below includes epitope/mimotope sequences recognized by the corresponding antibodies indicated:

TABLE 7

| Antibody | mAb-specific epitope |
|---|---|
| Rituxinmab | |
| Minnotope | CPYSNPSLC (SEQ ID NO: 19) |
| Palivizumab | |
| Epitope | NSELLSLINDMPITNDQKKLMSNN (SEQ ID NO: 30) |
| Cetuximab | |
| Mimotope 1 | CQFDLSTRRLKC (SEQ ID NO: 31) |
| Mimotope 2 | CQYNLSSRALKC (SEQ ID NO: 32) |
| Mimotope 3 | CVWQRWQKSYVC (SEQ ID NO: 33) |
| Mimotope 4 | CMWDRFSRWYKC (SEQ ID NO: 39) |
| Nivolumab | |
| Epitope 1 | SFVLNWYRMSPSNQTDKLAAFPEDR (SEQ ID NO: 35) |

TABLE 7-continued

| Antibody | mAb-specific epitope |
|---|---|
| Epitope 2 | SGTYLCGAISLAPKAQIKE (SEQ ID NO: 36) |
| QBEND-10 | |
| Epitope | ELPTQGTFSNVSTNVSPAKPTTTA (SEQ ID NO: 37) |
| Alemtuzmab | |
| Epitope | GQNDTSQTSSPS (SEQ ID NO: 38) |

In a preferred embodiment, the mAb-specific epitope is a mAb-specific epitope having an amino acid sequence of ELPTQGTFSNVSTNVSPAKPTTTA (SEQ ID NO: 37) and/or CPYSNPSLC (SEQ ID NO: 19).

In a more preferred embodiment, the CD22 CAR of the invention comprises 3 mAb-specific epitopes having an amino acid sequence of CPYSNPSLC (R) (SEQ ID NO: 19) and one having an amino acid sequence of ELPTQGTFSNVSTNVSPAKPTTTA (Q) (SEQ ID NO: 37).

In an even more preferred embodiment, the CD22 CAR of the invention comprises 2 mAb-specific epitopes having an amino acid sequence of CPYSNPSLC (R) (SEQ ID NO: 19) located at the NT part of the hinge, just after the VL.

In one aspect, at least one sequence to which rituximab binds to (R) and/or a sequence to which QBEND-10 binds to (Q) may be inserted into the linker GGGGSGGGGSGGGGS (SEQ ID NO: 40) and/or into the Hinge as previously described in (WO2016120216).

In a particular embodiment, the CD22 CAR of the present invention is a single chain CAR (scCAR).

In particular embodiments, the single chain anti-CD22 CAR of the invention comprises a scFv from m971 and at least one other binding domain, preferably specific for the distal part of CD22, alternatively for another B cell antigen, especially if expressed by B cells malignancies such as CD34, CD10, CD79a, CD20, IgD, CD5, CD23, CD19, STAT5, CD3, CD30, BCMA. In a particular embodiment, the CD22 CAR of the present invention is a multichain CAR (mcCAR). Multichain CD22 CARs are part of the present invention and may be produced as described in details in WO2014039523, which is incorporated herein by reference. In a particular embodiment, the $V_{H\ domain}$ and the $V_{L\ domain}$ of an immunoglobulin or a part of an immunoglobulin specific for CD22, may be carried by two different and isolated (non-covalently bound) chains of a multichain CAR.

In a multichain version, the CD22 CAR of the invention comprises at least two, preferably 3 transmembrane domains (non-covalently bound to each other) with at least one of the transmembrane domain comprising a scFv specific for CD22 of the invention.

In a particular embodiment, the $V_{H\ domain}$ and the $V_{L\ domain}$ of an immunoglobulin specific for CD22, preferably from m971 may be carried by one chain of a multichain CAR.

Figure 2:
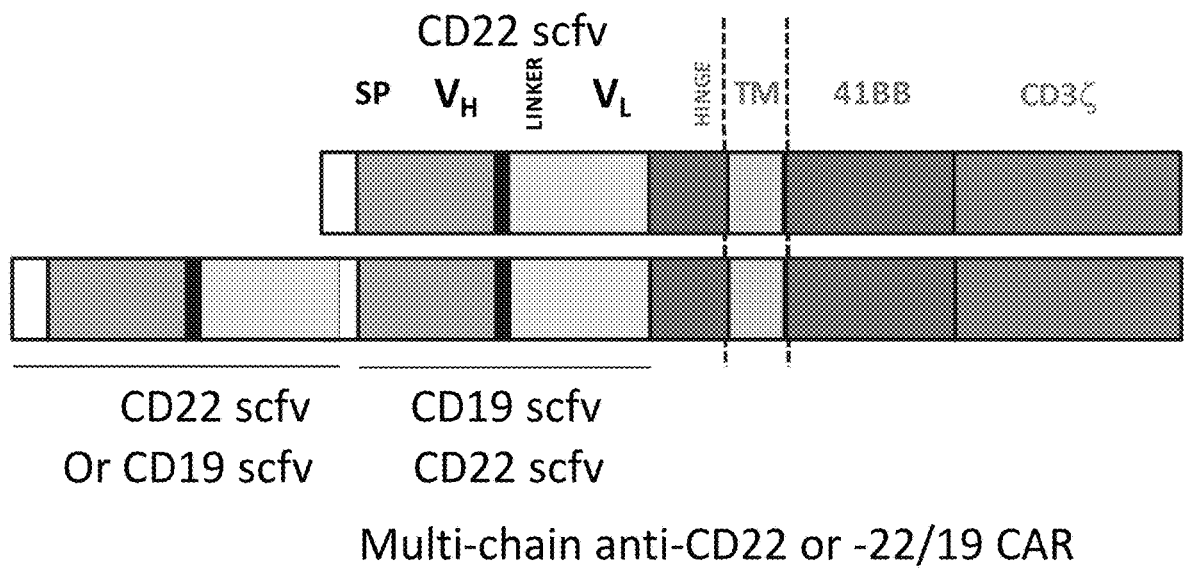
FIG. 2: Representation of a single chain and of a multi-chain CD22 CAR.
Figure 2:
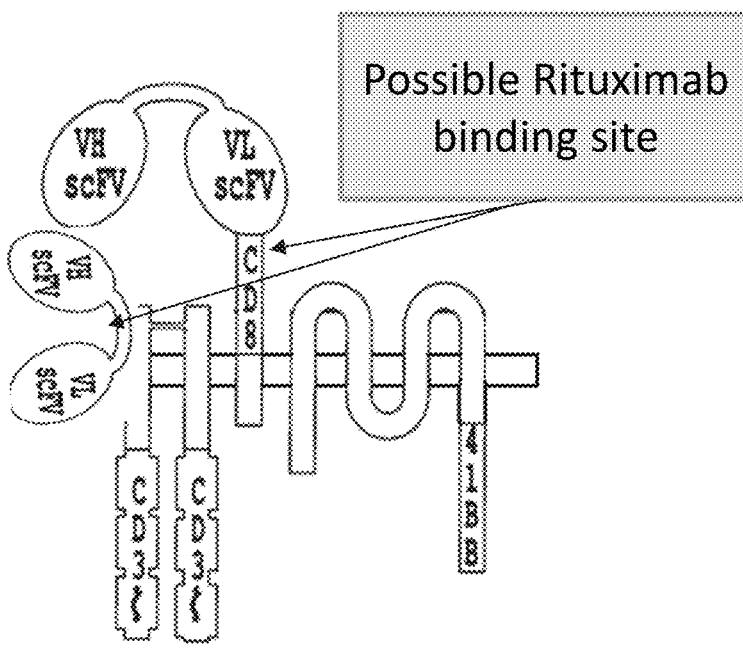

An example of scCD22 CAR and of mc CD22 CAR of the invention is provided FIG. 2.

In a particular embodiment, the $V_{H\ domain}$ and the $V_{L\ domain}$ of an immunoglobulin specific for CD22, preferably from m971 may be carried by one chain of a multichain CAR and the $V_{H\ domain}$ and the $V_{L\ domain}$ of another immunoglobulin specific for CD22, may be carried by another chain of the mc CAR.

Downregulation or mutation of target antigens is commonly observed in cancer cells, creating antigen-loss escape variants. Thus, to offset tumor escape and render immune cell more specific to target, the CD22 specific CAR according to the invention can comprise another extracellular ligand-binding domain, to simultaneously bind other elements in target thereby augmenting immune cell activation and function. In one embodiment, the extracellular ligand-binding domains can be placed in tandem on the same transmembrane polypeptide, and optionally can be separated by a linker.

In another embodiment, said different extracellular ligand-binding domains can be placed on different transmembrane polypeptides composing the multichain CAR. In another embodiment, the present invention relates to a population of CARs comprising different extracellular ligand binding domains, one of each is specific for CD22.

In one embodiment the extracellular binding domain specific for CD22 and the second extracellular binding domain are on the same scCAR, In another embodiment, the extracellular binding domain specific for CD22 and the second extracellular binding domain are on the same mc CAR and belong to the same or to two different and non-covalently bound transmembrane domains of said mc CAR.

As other second extracellular binding domain may be any extracellular binding domain binding specific to an antigen associated (co-expressed—even temporarily) to CD22 on pathological cells, such as CD34, CD10, CD79a, CD20, IgD, CD5, CD23, CD19, STAT5, CD3, CD30, BCMA, PAX5, CD19, CD20, CD30, glycosphingolipids, a major histocompatibility complex (MHC) molecule, an Ig, CD3, CD34, CD79, preferably CD79a, CD138, B7-1 (CD80), B7-2 (CD86), a major histocompatibility complex (MHC) molecule, BCMA (CD269, TNFRSF 17) or FLT-3, Pax5.

The invention also provides related CD22 CAR nucleic acids, CD22 CAR recombinant expression vectors, engineered TCR KO cells, preferably T cells comprising at least another edited gene endowed with the CD22 CAR, populations of said TCR KO cells endowed with a CD22 CAR, and pharmaceutical compositions relating to the CD22 CARs, protein, expression vector, engineered TCR KO CD52 KO cells expressing said CD22CAR of the invention.

The invention provides the following objects: a CD22 CAR of the invention-related nucleic acids, -recombinant expression vectors, engineered TCR KO cells comprising at least another edited gene selected from a gene conferring resistance to hypoxia, a gene conferring resistance to alemtuzumab, to protease inhibitor, such as bortezomib, a gene conferring resistance to PNA (dCK) and endowed with a CD22 CAR, and related nucleic acid, populations of engineered TCR KO cells comprising at least another edited gene as below, endowed with said CD22 CAR and pharmaceutical compositions comprising said same objects as a medicament.

Polynucleotides, Vectors:

The present invention relates to polynucleotides, vectors encoding the above described CD22 CAR according to the invention.

A polynucleotide may consist in an expression cassette or expression vector (e.g., a plasmid for introduction into a bacterial host cell, or a viral vector such as a baculovirus vector for transfection of an insect host cell, or a plasmid or viral vector such as a lentivirus or an adeno associated virus for introduction into a mammalian, preferably human host cell.

In a particular embodiment, the different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)).

Figure 4:
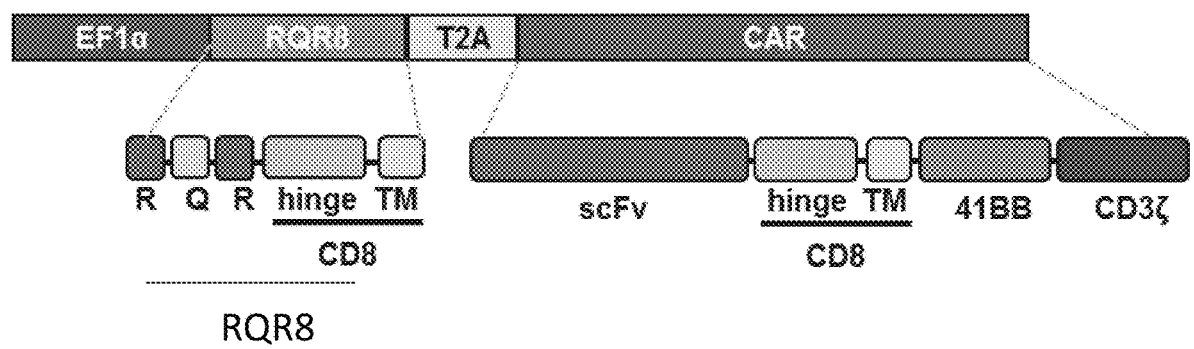
FIG. 4: Example of a polypeptide coded by a polynucleotide.

Accordingly, the present invention provides a vector as in FIG. 4 coding for a RQR8 and an anti-CD22CAR linked by a peptide 2A.

By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

A vector allowing a CD22 CAR of the invention to be expressed in a cell is another object of the present invention. In a preferred embodiment, said vector allows a transient expression of the CD22 CAR of the invention. In a more preferred embodiment said vector allows a constitutive and stable expression of a CD22 CAR of the invention by insertion of the sequence coding said CD22 CAR into the genome of a cell.

The expression of a CD22 CAR of the invention and/or the survival of the cell expressing the CD22 CAR of the invention may be controlled using a gene under the control of an inducible promoter as described in (R. Kuhn, F. Schwenk, M. Aguet, K. Rajewsky. Inducible gene targeting in mice. Science 8 Sep. 1995: Vol. 269 no. 5229 pp. 1427-1429 DOI:10.1126/science.7660125, and cited references.

In one embodiment, a CD22 CAR is provided wherein the extracellular domain comprises at least two CD20 mimotopes of SEQ ID NO 19 (CPYSNPSLC) located between m971 scFv domains and the hinge from human CD8alpha. Document Patent WO2016120216A1 discloses a method for preparing such constructions and is incorporated herein by reference.

In one embodiment, the present invention provides a vector comprising a sequence of SEQ ID NO: 22 coding a CD22 CAR.

To direct transmembrane polypeptide into the secretory pathway of a host cell, a secretory signal sequence (also known as a leader sequence, prepro sequence or pre sequence) is provided in polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In a preferred embodiment the signal peptide comprises the amino acid sequence SEQ ID NO: 1 and 2.

In a more preferred embodiment, the signal peptide of the CAR of the invention comprises the amino acid sequence of SEQ ID NO: 1 from human CD8 alpha.

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

Methods of engineering immune cells endowed with CD22 CARs:

The present invention encompasses a method of preparing immune cells for immunotherapy comprising introducing ex-vivo into said immune cells a polynucleotide or a vector encoding one of the CD22 CAR of the invention, preferably of SEQ ID NO: 15 as previously described.

In a preferred embodiment, said polynucleotides are included into a vector in view of being stably expressed in the immune cells.

According to further embodiments, said method further comprises the step of genetically modifying said cell to make it more suitable for adoptive transfer, and/or for use with a drug affecting said immune cell survival, in particular for transplant (also called allograft, or homograft) alone or in combination with the drug for which the immune cell is made resistant to.

In this later case, engineered cells may be initially isolated from a donor and used for a reinjection into the same donor in combination with a drug to which it is made resistant to.

For editing a gene, which means here, modifying a gene, or inactivating a gene, for example mutating a gene, deleting a gene, inserting a sequence in a gene, modifying the methylation of said gene (this includes the promotor of a gene), etc., methods described in PA201670503 are incorporated here by reference and illustrated in the examples below.

Methods described in MacLeod et al., Integration of a CD19 CAR into the TCR Alpha Chain Locus Streamlines Production of Allogeneic Gene-Edited CAR T Cells, Molecular Therapy (2017), dx.doi.org/10.1016/j.ymthe.2017.02.005, incorporated herein by reference are also a possible alternatives to the method used in the present invention for preparing a TCR KO CD22 CAR or a cell endowed with a CD22 CAR resistant to hypoxia by over expressing HIF-1a.

The method of the present invention is based on cellular homology-directed repair (HDR) mechanisms to "knock in" a CD22 CAR in the TRAC gene (encoding the TCR alpha subunit of the TCR) resulting in a more efficient product.

HDR with an exogenous DNA sequence has been described previously in T cells using short oligonucleotides paired with CRISPR/Cas9. Others have shown that adeno-associated virus (AAV) vectors can be used as a template in conjunction with a site-specific nuclease Crispr/Cas9 or MegaTAL to achieve gene insertion via HDR. In the present invention is provided a new method combining adeno-associated virus (AAV) vectors and TALEN® to insert a CAR into the TCR gene.

In UCART22, AAV6 vector may be used after genetic editing using specific TALEN® of a gene such as the TRAC gene (gene encoding the alpha subunit or the TCR) or any gene disclosed in PCT/EP2017/076798.

Because TALEN® are specific for a DNA sequence and allow integrating a sequence into a gene, preferably a TRAC gene, the present invention also provides an engineered immune cells comprising a sequence coding a CAR, preferably a CD22 CAR as described above located in a precise region of the TRAC gene determined by the TALEN® used. The sequence in the TRAC gene of said engineered immune cell, is unique due to the TALEN® specificity.

Accordingly, the present invention provides an engineered immune cell comprising the following sequence: $(YYY)_n$-ZZZ-$(XXX)_m$, with n is =1 to at least 10, m is =1 to 100 preferably m is >100 and represents the number of base pair of the sequence to be integrated, wherein ZZZ codes a self-cleaving peptide, such as a 2A peptide, in frame with the TRAC encoding sequence, Y is A or T or G or C and flanking or comprising a sequence of the TRAC gene targeted by a TALEN® comprising at least ttgtcccacagA-TATC (SEQ ID NO: 27), preferably ttgtcccacagATATCCAG (SEQ ID NO: 28) and (XXX)n is A or T or G or C and part of an exogenous sequence to be inserted into the TRAC gene, preferably a sequence encoding a CAR, more preferably a sequence encoding a CD22 CAR.

In one embodiment the TRAC gene is deleted and the inserted gene is expressed under the control of the TRAC promotor.

Additional or alternative sequences, such as IRES internal ribosome entry site; maybe interposed between the TALEN® target and XXX.

In the present invention, the TALEN® target is SEQ ID NO: 21 and the CAR CD22 is SEQ ID NO: 22.

In one embodiment the sequence cleaved by said TALEN® is AGAACCCTGACCCTG (SEQ ID NO: 70). The sequence AGAACCCTGACCCTG (SEQ ID NO: 70) may be conserved at least in part (see, FIG. 9) in an engineered cell of the invention depending on the insert sequence.

The present invention provides an engineered immune cell comprising a TRAC gene comprising a SEQ ID NO: 22.

The present invention provides an engineered immune cell comprising a sequence encoding a CAR specific for CD19 or a sequence encoding a CAR specific for CD22 inserted into the TRAC gene, preferably anywhere at the locus: AGAACCCTGACCCTG (SEQ ID NO: 70).

Thus, in particular embodiments, the engineered immune cell of the invention comprises two different sequences encoding a CAR and express said two different CARs. At the cell surface, undetectable level of TCR.

Thus, in particular embodiments, the engineered immune cell of the invention comprises two different sequences encoding a CAR and express said two different CARs. At the cell surface, undetectable level of TCR and of MHC Class I.

the engineered immune cell of the invention comprises into its genomic TRAC gene a sequence coding CD22, preferably of SEQ ID NO: 22, and another genomic sequence in which another exogenous gene coding for a CAR specific for CD19 is inserted.

the engineered immune cell of the invention comprises into its genomic TRAC gene a sequence coding CD22, preferably of SEQ ID NO: 22, and another genomic sequence in which another exogenous gene coding for a CAR specific for CD34 is inserted.

the engineered immune cell of the invention comprises into its genomic TRAC gene a sequence coding CD22, preferably of SEQ ID NO: 22, and another genomic sequence in which another exogenous gene coding for a CAR specific for CD79a is inserted.

the engineered immune cell of the invention comprises into its genomic TRAC gene a sequence coding CD22, preferably of SEQ ID NO: 22, and another genomic sequence in which another exogenous gene coding for a CAR specific for CD79b is inserted.

The engineered immune cell of the invention comprises into its genomic TRAC gene a sequence coding CD22, preferably of SEQ ID NO: 22, and another genomic sequence in which another exogenous gene coding for a CAR specific for CD10 is inserted.

The engineered immune cell of the invention comprises into its genomic TRAC gene a sequence coding CD22, preferably of SEQ ID NO: 22, and another genomic sequence in which another exogenous gene coding for a CAR specific for IgD is inserted.

The engineered immune cell of the invention comprises into its genomic TRAC gene a sequence coding CD22, preferably of SEQ ID NO: 22, and another genomic sequence in which another exogenous gene coding for a CAR specific for CD5 is inserted.

The engineered immune cell of the invention comprises into its genomic TRAC gene a sequence coding CD22, preferably of SEQ ID NO: 22, and another genomic sequence in which another exogenous gene coding for a CAR specific for CD23 is inserted.

The engineered immune cell of the invention comprises into its genomic TRAC gene a sequence coding CD22, preferably of SEQ ID NO: 22, and another genomic sequence in which another exogenous gene coding for a CAR specific for CD30 is inserted.

The engineered immune cell of the invention comprises into its genomic TRAC gene a sequence coding CD22, preferably of SEQ ID NO: 22, and another genomic sequence in which another exogenous gene coding for a CAR specific for BCMA is inserted.

The engineered immune cell of the invention comprises into its genomic TRAC gene a sequence coding CD22, preferably of SEQ ID NO: 22, and another genomic sequence in which another exogenous gene coding for a CAR specific for FLT3 is inserted.

The engineered immune cell of the invention comprises into its genomic TRAC gene a sequence coding CD22, preferably of SEQ ID NO: 22, and another genomic sequence in which another exogenous gene coding for a CAR specific for CD138 is inserted.

The engineered immune cell of the invention comprises into its genomic TRAC gene a sequence coding CD22, preferably of SEQ ID NO: 22, and another genomic sequence in which another exogenous gene coding for a CAR specific for CD80 is inserted.

The engineered immune cell of the invention comprises into its genomic TRAC gene a sequence coding CD22, preferably of SEQ ID NO: 22, and another genomic sequence in which another exogenous gene coding for a CAR specific for CD86 is inserted.

Another genomic sequence in which another exogenous gene coding for a second CAR is inserted may be any one of the genes disclosed in PCT/EP2017/076798 or in WO2017069958A2.

The other exogenous gene encoding a CAR may be inserted into the TRAC gene in frame with a self-cleaving peptide and with the CD22 CAR sequence, preferably SEQ ID NO or into another gene encoding a protein as those disclosed in PCT/EP2017/076798, or chosen among PD1 (Uniprot Q15116), CTLA4 (Uniprot P16410), PPP2CA (Uniprot P67775), PPP2CB (Uniprot P62714), PTPN6 (Uniprot P29350), PTPN22 (Uniprot Q9Y2R2), LAG3 (Uniprot P18627), HAVCR2 (Uniprot Q8TDQO), BTLA (Uniprot Q7Z6A9), CD160 (Uniprot O95971), TIGIT (Uniprot Q495A1), CD96 (Uniprot P40200), CRTAM (Uniprot O95727), LAIR1 (Uniprot Q6GTX8), SIGLEC7 (Uniprot Q9Y286), SIGLEC9 (Uniprot Q9Y336), CD244 (Uniprot Q9BZW8), TNFRSF10B (Uniprot O14763), TNFRSF10A (Uniprot O00220), CASP8 (Uniprot Q14790), CASP10 (Uniprot Q92851), CASP3 (Uniprot P42574), CASP6 (Uniprot P55212), CASP7 (Uniprot P55210), FADD (Uniprot Q13158), FAS (Uniprot P25445), TGFBRII (Uniprot P37173), TGFRBRI (Uniprot Q15582), SMAD2 (Uniprot Q15796), SMAD3 (Uniprot P84022), SMAD4 (Uniprot Q13485), SMAD10 (Uniprot B7ZSB5), SKI (Uniprot P12755), SKIL (Uniprot P12757), TGIF1 (Uniprot Q15583), IL10RA (Uniprot Q13651), IL10RB (Uniprot Q08334), HMOX2 (Uniprot P30519), IL6R (Uniprot P08887), IL6ST (Uniprot P40189), EIF2AK4 (Uniprot Q9P2K8), CSK (Uniprot P41240), PAG1 (Uniprot Q9NWQ8), SIT1 (Uniprot Q9Y3P8), FOXP3 (Uniprot Q9BZS1), PRDM1 (Uniprot Q60636), BATF (Uniprot Q16520), GUCY1A2 (Uniprot P33402), GUCY1A3 (Uniprot Q02108), GUCY1B2 (Uniprot Q8BXH3) and GUCY1B3 (Uniprot Q02153).

Preferred edited (KO) genes in UCART22 are TNFRSF10B (Uniprot O14763), TNFRSF10A (Uniprot O00220), IL10RA (Uniprot Q13651), IL10RB (Uniprot Q08334, TGFBRII (Uniprot P37173), TGFRBRI (Uniprot Q15582), PD1 (Uniprot Q15116), CTLA4 (Uniprot P16410), LAG3 (Uniprot P18627), HAVCR2 (Uniprot Q8TDQO), TIGIT (Uniprot Q495A1).

Preferably the gene in which the second CAR is inserted is a genomic gene active during T cell activation selected from any one of those described in Table 8 below.

TABLE 8

| Symbol | Gene description |
|---|---|
| CD3G | CD3 gamma |
| Rn28s1 | 28S ribosomal RNA |
| Rn18s | 18S ribosomal RNA |
| Rn7sk | RNA, 7SK, nuclear |
| Actg1 | actin, gamma, cytoplasmic 1 |
| B2m | beta-2 microglobulin |
| Rpl18a | ribosomal protein L18A |
| Pabpc1 | poly(A) binding protein, cytoplasmic 1 |
| Gapdh | glyceraldehyde-3-phosphate dehydrogenase |
| Rpl19 | ribosomal protein L19 |
| Rpl17 | ribosomal protein L17 |
| Rplp0 | ribosomal protein, large, P0 |
| Cfl1 | cofilin 1, non-muscle |
| Pfn1 | profilin 1 |

Or, the gene in which the second CAR is inserted is in safe harbor loci as disclosed in PCT/EP2017/076798 or in Table 9 below.

TABLE 9

| Zfp640 | zinc finger protein 640 |
|---|---|
| LOC100038422 | uncharacterized LOC100038422 |
| Zfp600 | zinc finger protein 600 |
| Serpinb3a | serine (or cysteine) peptidase inhibitor, clade B (ovalbumin), member 3A |

TABLE 9-continued

| Tas2r106 | taste receptor, type 2, member 106 |
|---|---|
| Magea3 | melanoma antigen, family A, 3 |
| Omt2a | oocyte maturation, alpha |
| Cpxcr1 | CPX chromosome region, candidate 1 |
| Hsf3 | heat shock transcription factor 3 |
| Pbsn | Probasin |
| Sbp | spermine binding protein |
| Wfdc6b | WAP four-disulfide core domain 6B |
| Meiob | meiosis specific with OB domains |
| Dnm3os | dynamin 3, opposite strand |
| Skint11 | selection and upkeep of intraepithelial T cells 11 |

The other gene in which the second CAR may be inserted may be a gene encoding any one of the proteins in Table 10 below.

TABLE 10 interleukin 21
interleukin 3
isopentenyl-diphosphate delta isomerase 2
granzyme C
chemokine (C-C motif) receptor 8
interleukin 2
interleukin 1 receptor, type I
tumor necrosis factor (ligand) superfamily, member 4
neuronal calcium sensor 1
CDK5 and Abl enzyme substrate 1
transmembrane and tetratricopeptide repeat containing 2
LON peptidase N-terminal domain and ring finger 1
glycoprotein 49 A
polo-like kinase 2
lipase, endothelial
cyclin-dependent kinase inhibitor 1A (P21)
grainyhead-like 1 (Drosophila)
cellular retinoic acid binding protein II
adenylate kinase 4
microtubule-associated protein 1B
acyl-CoA synthetase long-chain family member 6
zinc finger E-box binding homeobox 2
CD200 antigen
carboxypeptidase D
thioredoxin reductase 3
myosin IE
RNA binding protein with multiple splicing 2
mitogen-activated protein kinase kinase 3, opposite strand
PERP, TP53 apoptosis effector
myosin X
immediate early response 3
folliculin interacting protein 2
leukocyte immunoglobulin-like receptor, subfamily B, member 4
circadian associated repressor of transcription
RAR-related orphan receptor gamma
proline/serine-rich coiled-coil 1
cysteine rich protein 2
cAMP responsive element modulator
chemokine (C-C motif) ligand 4
nuclear receptor subfamily 4, group A, member 2
transglutaminase 2, C polypeptide
synapse defective 1, Rho GTPase, homolog 2 (C. elegans)
sprouty homolog 1 (Drosophila)
activating transcription factor 3
pogo transposable element with KRAB domain
tumor necrosis factor receptor superfamily, member 21
cytokine inducible SH2-containing protein
lymphotoxin A
FBJ osteosarcoma oncogene
signaling lymphocytic activation molecule family member 1
syndecan 3
mitochondrial ribosomal protein L47
Ladinin
E2F transcription factor 5
ISG15 ubiquitin-like modifier
aryl-hydrocarbon receptor
diacylglycerol O-acyltransferase 2
FBJ osteosarcoma oncogene B
pleckstrin homology-like domain, family A, member 3
potassium voltage-gated channel, subfamily Q, member 5

TABLE 10-continued tumor necrosis factor receptor superfamily, member 10b
Mir17 host gene 1 (non-protein coding)
glucose-fructose oxidoreductase domain containing 1
plexin A1
heat shock factor 2
carbohydrate sulfotransferase 11
growth arrest and DNA-damage-inducible 45 gamma
solute carrier family 5 (sodium-dependent vitamin transporter), member 6
interferon induced transmembrane protein 3
DENN/MADD domain containing 5A
plasminogen activator, urokinase receptor
solute carrier family 19 (thiamine transporter), member 2
ubiquitin domain containing 2
nuclear receptor subfamily 4, group A, member 3
zinc finger protein 52
SH3 domain containing ring finger 1
dihydrouridine synthase 2
cyclin-dependent kinase 5, regulatory subunit 1 (p35)
processing of precursor 7, ribonuclease P family, (*S. cerevisiae*)
growth factor independent 1
interleukin 15 receptor, alpha chain
BCL2-like 1
protein tyrosine phosphatase, receptor type, S
plasmacytoma variant translocation 1
fos-like antigen 2
BCL2-associated X protein
solute carrier family 4, sodium bicarbonate cotransporter, member 7
tumor necrosis factor receptor superfamily, member 4
chemokine (C-X-C motif) ligand 10
polo-like kinase 3
CD3E antigen, epsilon polypeptide associated protein
tumor necrosis factor (ligand) superfamily, member 11
polymerase (RNA) III (DNA directed) polypeptide D
early growth response 2
DnaJ (Hsp40) homolog, subfamily C, member 2
DNA topoisomerase 1, mitochondrial
tripartite motif-containing 30D
DnaJ (Hsp40) homolog, subfamily C, member 21
SAM domain, SH3 domain and nuclear localization signals, 1
solute carrier family 5 (inositol transporters), member 3
mitochondrial ribosomal protein L15
dual specificity phosphatase 5
apoptosis enhancing nuclease
ets variant 6
DIM1 dimethyladenosine transferase 1-like (*S. cerevisiae*)
2'-5' oligoadenylate synthetase-like 1
UTP18, small subunit (SSU) processome component, homolog (yeast)
BRCA2 and CDKN1A interacting protein
synaptotagmin-like 3
5-methyltetrahydrofolate-homocysteine methyltransferase reductase
URB2 ribosome biogenesis 2 homolog (*S. cerevisiae*)
ubiquitin-conjugating enzyme E2C binding protein
lysine (K)-specific demethylase 2B
queuine tRNA-ribosyltransferase domain containing 1
ubiquitin specific peptidase 31
eukaryotic translation initiation factor 2-alpha kinase 2
ATPase family, AAA domain containing 3A
adhesion molecule, interacts with CXADR antigen 1
SUMO/sentrin specific peptidase 3
ESF1, nucleolar pre-rRNA processing protein, homolog (*S. cerevisiae*)
deoxynucleotidyltransferase, terminal, interacting protein 2
TGFB-induced factor homeobox 1
eukaryotic translation initiation factor 1A
interferon-stimulated protein
pleiomorphic adenoma gene-like 2
PWP2 periodic tryptophan protein homolog (yeast)
furin (paired basic amino acid cleaving enzyme)
tumor necrosis factor
apoptosis antagonizing transcription factor
interferon, alpha-inducible protein 27 like 2A
ST6 (alpha-N-acetyl-neuraminyl-2,3-beta-galactosyl-1,3)-N-acetylgalactosaminide alpha-2,6-sialyltransferase 4
methyltransferase like 1
notchless homolog 1 (*Drosophila*)
mitochondrial ribosomal protein L3
UBX domain protein 2A
guanine nucleotide binding protein-like 2 (nucleolar)
programmed cell death 11

TABLE 10-continued cyclin-dependent kinase 8
eukaryotic translation initiation factor 5B
RNA terminal phosphate cyclase-like 1
NSFL1 (p97) cofactor (p47)
nuclear factor of kappa light polypeptide gene enhancer in B cells inhibitor, delta
M-phase phosphoprotein 10 (U3 small nucleolar ribonucleoprotein)
GRAM domain containing 1B
ERO1-like (*S. cerevisiae*)
nuclear receptor subfamily 4, group A, member 1
surfeit gene 2
N(alpha)-acetyltransferase 25, NatB auxiliary subunit
yrdC domain containing (*E. coli*)
La ribonucleoprotein domain family, member 4
SDA1 domain containing 1
importin 4
inducible T cell co-stimulator
solute carrier family 7 (cationic amino acid transporter, y+ system), member 1
arsA arsenite transporter, ATP-binding, homolog 1 (bacterial)
polymerase (RNA) I polypeptide C
spermatogenesis associated 5
ubiquitin specific peptidase 18
placenta-specific 8
general transcription factor IIF, polypeptide 1
nuclear factor of kappa light polypeptide gene enhancer in B cells inhibitor, beta
PHD finger protein 6
RRN3 RNA polymerase I transcription factor homolog (yeast)
cytotoxic and regulatory T cell molecule
COP9 (constitutive photomorphogenic) homolog, subunit 6 (*Arabidopsis thaliana*)
asparagine-linked glycosylation 3 (alpha-1,3-mannosyltransferase)
tryptophanyl-tRNA synthetase
hypoxia up-regulated 1
family with sequence similarity 60, member A
bone marrow stromal cell antigen 2
nuclear factor of kappa light polypeptide gene enhancer in B cells 2, p49/p100
UTP20, small subunit (SSU) processome component, homolog (yeast)
CD274 antigen
proviral integration site 1
signal transducer and activator of transcription 5A
CD69 antigen
pitrilysin metallepetidase 1
cyclin-dependent kinase 6
DEAD (Asp-Glu-Ala-Asp) box (SEQ ID NO: 71) polypeptide 27
polymerase (RNA) I polypeptide B
tumor necrosis factor, alpha-induced protein 3
nodal modulator 1
NOP14 nucleolar protein
ribosomal protein L7-like 1
methionyl aminopeptidase 1
hypoxia inducible factor 1, alpha subunit
Janus kinase 2
nuclear factor of kappa light polypeptide gene enhancer in B cells 1, p105
reticuloendotheliosis oncogene
septin 2
nucleolar protein interacting with the FHA domain of MKI67
elongation factor Tu GTP binding domain containing 2
myelocytomatosis oncogene
dyskeratosis congenita 1, dyskerin
carnitine deficiency-associated gene expressed in ventricle 3
GTP binding protein 4
HEAT repeat containing 1
proteaseome (prosome, macropain) activator subunit 3 (PA28 gamma, Ki)
La ribonucleoprotein domain family, member 1
DNA segment, Chr 19, Brigham & Women's Genetics 1357 expressed
eukaryotic translation initiation factor 3, subunit D
TSR1 20S rRNA accumulation
MYB binding protein (P160) 1a
T cell activation Rho GTPase activating protein
RAB8B, member RAS oncogene family
DEAD (Asp-Glu-Ala-Asp) box (SEQ ID NO: 71) polypeptide 21
chaperonin containing Tcp1, subunit 4 (delta)
coiled-coil-helix-coiled-coil-helix domain containing 2
WD repeat domain 43

UCART22 may be prepared using an AAV vector, preferably AAV6 vector and even more preferably AAV6/2 vector for inserting the CD22 CAR or another gene as disclosed herein. AAV vector(s) may be used after genetic editing of a gene such as the TRAC gene (gene encoding the alpha subunit or the TCR) or any gene disclosed in PCT/EP2017/076798, using a specific endonuclease.

Adoptive cell transfer is the transfer of cells into a patient. The cells may have originated from the patient him- or herself and then been altered before being transferred back (syngeneic transfer) or, they may have come from another individual. The cells are most commonly derived from the immune system, with the goal of transferring improved immune functionality and characteristics along with the cells back to the patient. Transferring autologous cells, or cells from the patient, minimizes graft-versus-host disease (GVHD) or tissue or organ rejection. Similarly transferring TCR-deficient T cells CD22 CART cells minimizes GVHD. Transferring TCR-deficient MHCI deficient CD22CART minimizes GVHD and HVGD.

In one embodiment, the step of genetically modifying (engineering) said immune cell takes place before the step of introducing the polynucleotides or vectors encoding one of the CD22 CAR of the invention into said cells. According to a first aspect, the immune cell can be made less allogeneic, for instance, by inactivating at least one gene expressing one or more component of T-cell receptor (TCR) as described in WO 2013/176915, which can be combined with the inactivation of a gene encoding or regulating HLA expression such as β2m gene as described in WO2008102199 or in WO2015136001 or in WO2016201047 which are all incorporated herein by reference. Accordingly, the risk of graft versus host syndrome and the risk of graft rejection are significantly reduced.

According to another aspect, the immune cells of the invention can be further genetically engineered to improve the resistance of engineered immune cells to an immunosuppressive drug or a chemotherapy treatment, which are used as standard care for treating CD22 positive malignant cells as disclosed in WO201575195 which is incorporated herein by reference.

Resistance to CAMPATH® (Alemtuzumab)

In one preferred embodiment, the genes which can be inactivated to confer drug resistance to the T-cell is a glucocorticoid receptor (GR) and CD52. Genes are inactivated to make the cells resistant to these treatments and give them a competitive advantage over patient's own T-cells not endowed with specific CD22 CARs.

The inactivation of the CD52 and TRAC gene in the engineered immune cell according to the invention is performed using a TALE nuclease or a CRISPR CAS9 system.

In one more preferred embodiment, the gene which can be inactivated to confer drug resistance to the T-cell is the CD52 in TCR KO immune T cells endowed with a CD22 CAR.

In one preferred embodiment, the gene which can be inactivated to confer drug resistance to the T-cell is a glucocorticoid receptor (GR).

Expression of CD3 gene can also be suppressed or reduced to confer resistance to Teplizumab, which is another immune suppressive drug. Expression of HPRT can also be suppressed or reduced according to the invention to confer resistance to 6-thioguanine, a cytostatic agent commonly used in chemotherapy especially for the treatment of acute lymphoblasic leukemia.

Resistance to purine nucleotide analogs by deletion of human deoxycytidine kinase (dCK) gene.

In one preferred embodiment, the gene which can be inactivated to confer drug resistance to the T-cell is the human deoxycytidine kinase (dCK) gene. This enzyme is required for the phosphorylation of the deoxyribonucleosides deoxycytidine (dC), deoxyguanosine (dG) and deoxyadenosine (dA). Purine nucleotide analogs (PNAs) are metabolized by dCK into mono-, di- and tri-phosphate PNA. Their triphosphate forms and particularly clofarabine triphosphate compete with ATP for DNA synthesis, acts as proapoptotic agent and are potent inhibitors of ribonucleotide reductase (RNR) which is involved in trinucleotide production.

The inactivation of the dCK gene in the engineered immune cell according to the invention is mediated by a TALE nuclease or a CRISPR CAS9 system. To achieve this goal, several pairs of dCK TALE-nuclease have been designed, assembled at the polynucleotide level and validated by sequencing. Examples of TALE-nuclease pairs which can be used according to the present invention are depicted in PCT/EP2014/075317.

This dCK inactivation in engineered immune cells of the invention confers resistance to purine nucleoside analogs (PNAs) such as clofarabine and fludarabine.

In another preferred embodiment, the dCK inactivation in engineered immune cells of the invention is combined with an inactivation of TRAC genes rendering these double knock out (KO) (TCR or TRAC KO and dCK KO) cells both resistant to drug such as clofarabine and less allogeneic.

In another preferred embodiment, the CD52 inactivation in engineered immune cells of the invention is combined with an inactivation of TRAC gene rendering these double knock out (KO) (TCR or TRAC KO and CD52 KO) cells both resistant to drug such as CAMPATH® (alemtuzumab) and less allogeneic.

This double feature is particularly useful for a therapeutic goal, allowing "off-the-shelf" allogeneic cells (UCART22) for immunotherapy in conjunction with chemotherapy to treat patients with cancer in need thereof. This double KO inactivation dCK/TRAC or CD52/TRAC can be performed simultaneously or sequentially. One example of TALE-nuclease dCK/TRAC pairs which gave success in the invention is described in PCT/EP2014/075317, in particular, the target sequences in the 2 loci (dCK and TRAC). Document PCT/EP2014/075317 is incorporated herein in its entirety.

The present invention provides a primary T cells expressing a CD22 CAR of SEQ ID NO: 15, wherein, wherein the CD52 and TRAC genes are inactivated by deletion for their use in the treatment of CLL, ALL, preferably their aggressive, relapsing refractory forms, optionally in lymphodepleted patients, more preferably relapsing refractory forms of B-ALL.

According to a further aspect of the invention, the immune cells can be further manipulated to make them more active or limit exhaustion, by inactivating genes encoding proteins that act as "immune checkpoints" that act as regulators of T-cells activation, such as PDCD1 or CTLA-4. Examples of genes, which expression could be reduced or suppressed are indicated in Table 1.

The present invention also provides a primary T cells expressing a CD22 CAR of SEQ ID NO: 15, wherein the CD52, TRAC and dCK genes were deleted.

In another embodiment the present invention also provides a primary T cells expressing a CD22 CAR that were made resistant to hypoxia.

The present invention also provides a primary T cells expressing a CD22 CAR of SEQ ID NO: 15, wherein the CD52, TRAC and dCK genes were deleted and sequences of HIF-1a were inserted to make cells resistant to hypoxia.

Engineered cells resistant to hypoxia

In particular embodiments, the expression and cytolytic activity of CD22 CAR T cell of the invention is maintained, or the expression of CD22 CAR T cell induced and the activity maintained under low oxygen condition (hypoxia), (as compared to normal oxygen condition 20% $O_2$ vs 1 to 5% $O_2$) and said cell still target and destroy tumor cells when embedded into tissues.

Examples of hypoxia-inducible CAR in T cell are described (in WO2013123061 or in Juillerat, A. et al. An oxygen sensitive self-decision making engineered CAR T-cell, Sci. Rep. 7, 39833; doi: 10.1038/srep39833 (2017), both incorporated by reference): A synthetic promoter specific for the OxiTF driving the expression of the CD22 CAR was constructed. The OxiTF is design to activate a synthetic genetic element encoding a CD22 CAR. Upon tumor encounter, (creating hypoxia), engineered T cells can "detect" a decrease in oxygen level (as compared to the mean level of $O_2$ in the blood) and trigger the expression of the CD22 CAR. Cell surface exposure of CD22 CAR enables the recognition of tumor antigen under hypoxia that eventually triggers T cells activation and proliferation via the activation and co-stimulatory domains present within said CD22 CAR. Ultimately, tumor antigen expressing cells are lysed by the UCART22 of the invention.

In the present invention, immune cells may be also engineered to remain efficient under low $O_2$ condition (low oxygen concentration means 1-5%) by overexpressing at least one, preferably all of the following factors: Oct3, Oct4, Sox2, Klf4 and c-Myc, or by editing a HIF-1α factor.

In the present invention, an oxygen sensitive CD22 single chain CAR-expressing engineered cell and a hypoxia resistant CD22 CAR-expressing engineered cell were constructed and tested successfully.

Because CD22 is mainly expressed on CD22-expressing B cell malignancies, which are "liquid" tumors" and therefore are not supposed to create hypoxia in contrast to solid tumor, it was not expected that a CD22 CAR engineered immune cells resistant to hypoxia would be more efficient than CD22 CAR engineered immune cells which are not resistant to hypoxia against B-ALL from patient. In fact, the UCART22 of the invention reaching the nested cancer cells clustered or homing in tissues may be able to lyse these cells.

Other genes may be edited in the UCART22 of the present invention such as those in Table 11 below.

TABLE 11

List of genes encoding immune checkpoint proteins that may be inactivated according to the present invention in the CD22 CAR engineered T cells of the invention:

| Pathway | | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1 (PD-1 CD279) | PDCD1 |
| | CD223 (lag3) | LAG3 |
| | HAVCR2 (tim3) | HAVCR2 |
| | BTLA(cd272) | BTLA |
| | CD160(by55) | CD160 |
| | IgSF family | TIGIT |
| | | CD96 |
| | | CRTAM |

TABLE 11-continued

List of genes encoding immune checkpoint proteins that may be inactivated according to the present invention in the CD22 CAR engineered T cells of the invention:

| Pathway | | Genes that can be inactivated In the pathway |
|---|---|---|
| | LAIR1(cd305) | LAIR1 |
| | SIGLECs | SIGLEC7 |
| | | SIGLEC9 |
| | CD244(2b4) | CD244 |
| Death receptors | TRAIL | INFRSF10B, INFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL6ST |
| Prevention of TCR signalling | | CSK, PAG1 SIT1 |
| Induced Treg Transcription factors controlling exhaustion | induced Treg transcription factors controlling exhaustion | FOXP3 PRDM1 (=blimp1, heterozygotes mice control chronic viral infection better than wt or conditional KO) BATF |
| Hypoxia mediated tolerance | iNOS induced guanylated cyclase | GUCY1A2, GUCY1A3, GUCY1B2, GUCY1B3 |

The present invention provides an isolated engineered immune T cells expressing a CD22 CAR of SEQ ID NO: 15, wherein, the dCK and/or CD52 and TRAC genes are edited, that is, inactivated by deletion, for their use in the treatment of CLL, ALL, preferably their aggressive, relapsing refractory forms, in lymphodepleted patients.

The present invention provides an isolated engineered immune T cells expressing a CD22 CAR of SEQ ID NO: 15, wherein, the b2m and TRAC genes are edited, that is, inactivated by deletion, for their use in the treatment of CLL, ALL, preferably their aggressive, relapsing refractory forms, in lymphodepleted patients.

The present invention provides an isolated engineered immune T cells expressing a CD22 CAR of SEQ ID NO: 15, wherein TRAC and IL-10R genes are edited, that is, inactivated by deletion, for their use in the treatment of CLL, ALL, preferably their aggressive, relapsing refractory forms, in lymphodepleted patients. The present invention provides an engineered immune T cells expressing a CD22 CAR (UCART22) comprising a deficient TCR alpha gene (so that the cell surface expression of the TCR is compromised), a B2M deficient gene (so that the expression of MHC class I molecules at the cell surface is compromised), and in addition a TGFbeta receptor KO gene.

The present invention provides an engineered immune T cells expressing a CD22 CAR (UCART22) comprising a deficient TCR alpha gene (so that the cell surface expression of the TCR is compromised), a B2M deficient gene (so that the expression of MHC class I molecules at the cell surface is compromised), and in addition an IL-10 receptor KO gene.

The present invention provides an engineered immune T cells expressing a CD22 CAR (UCART22) comprising a deficient TCR alpha gene (so that the cell surface expression of the TCR is compromised), a B2M deficient gene (so that the expression of MHC class I molecules at the cell surface is compromised), and in addition an AHR KO gene.

The present invention provides an engineered immune T cells expressing a CD22 CAR (UCART22) comprising a deficient TCR alpha gene (so that the cell surface expression of the TCR is compromised), a B2M deficient gene (so that the expression of MHC class I molecules at the cell surface is compromised), and in addition a PD1 KO gene.

The present invention provides an engineered immune T cells expressing a CD22 CAR (UCART22) comprising a deficient TCR alpha gene (so that the cell surface expression of the TCR is compromised), a B2M deficient gene (so that the expression of MHC class I molecules at the cell surface is compromised), and in addition a LAG-3 KO gene.

The present invention provides an engineered immune T cells expressing a CD22 CAR (UCART22) comprising a deficient TCR alpha gene (so that the cell surface expression of the TCR is compromised), a B2M deficient gene (so that the expression of MHC class I molecules at the cell surface is compromised), and in addition a TIM-3 KO gene.

The present invention provides an isolated engineered immune T cells expressing a CD22 CAR of SEQ ID NO: 15 wherein, wherein the CD52, and TRAC genes are inactivated by deletion for their use in the treatment of relapsing refractory forms of BALL, in lymphodepleted patients.

In a preferred embodiment a method of engineering the immune cells involves introducing into said T cells polynucleotides, in particular mRNAs, encoding specific rare-cutting endonuclease to selectively inactivate the genes, as those mentioned above, by DNA cleavage.

In a more preferred embodiment said rare-cutting endonucleases are TALE-nucleases or Cas9 endonuclease. TAL-nucleases have so far proven higher specificity and cleavage efficiency over the other types of rare-cutting endonucleases, making them the endonucleases of choice and preferred for producing of the engineered immune cells on a large scale with a constant turn-over.

Delivery Methods

The different methods described above involve introducing a CD22 CAR of the invention into a cell. As non-limiting examples, said CD22 CAR can be introduced as a transgene encoded by one plasmid vector of the invention. Said plasmid vector encoding a CD22 CAR of the invention can also contain a selection marker which provides for identification and/or selection of cells which received said vector.

A method allowing a CD22 CAR according to the invention to be introduced and then expressed into an isolated immune cell was described elsewhere, for example in WO2013126720 or in WO2015121454 which are incorporated herein by reference in entirety.

Polypeptides corresponding to the CD22 CAR of the invention may be synthesized in situ in the cell as a result of the introduction of polynucleotides encoding said polypeptides into the cell. Alternatively, said polypeptides could be produced outside the cell and then introduced thereto. Methods for introducing a polynucleotide construct into cells are known in the art and including as non-limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, such as lentiviruses, adenoviruses, adeno associated virus), liposome and the like. For example, transient transformation methods include for example microinjection, electroporation or particle bombardment. Said polynucleotides may be included in vectors, more particularly plasmids or virus, in view of being expressed in cells.

In a preferred embodiment said polynucleotide encoding a CD22 CAR is inserted into an AAV6 vector and introduced into a given gene. Methods for preparing a vector allowing the CD22 CAR of the invention to be introduced and then expressed into an isolated T cell were described elsewhere, for example in WO2013126720 which is incorporated herein by reference.

Engineered Immune Cells (UCART)

An engineered immune cell endowed with a CD22 CAR (UCART22) is another object of the present invention.

Preferably said immune cell is an isolated immune cell, more preferably an isolated immune T cell, more preferably an isolated primary immune T cell.

The UCART22 is provided as a medicament, thus a therapeutically efficient amount of UCART22 is provided as a medicament.

"A primary immune cell" according to the invention means a "cell originating from a tissue such as a blood sample or from peripheral blood mononuclear cells (PBMCs) and that may be in culture for a few passages, eventually frozen before use, said primary immune cell has a limited capacity of division (Raulf-Heimsoth M. T cell—primary culture from peripheral blood. *Methods Mol Med.* 2008; 138:17-30. doi: 10.1007/978-1-59745-366-0) as compared to a transformed or cancerous cell.

An immune cell according to the invention is preferably an immune T or NK cell. Accordingly, an engineered immune cell according the invention is isolated from a blood sample, is a primary cell and derived from an immune T cell selected from inflammatory T-lymphocytes, cytotoxic T-lymphocytes, regulatory T-lymphocytes or helper T-lymphocytes, Natural Killer T-cell, preferably from cytotoxic T-lymphocytes and further engineered.

Engineered means that primary immune cells are modified so that they will be endowed with a CD22 CAR and at least one gene is edited, preferably said cells are modified so that they will be endowed with a CD22 CAR and will neither express a TCR nor die in the presence of purine nucleotide analogs.

In other word, engineered immune cells means a TCR KO isolated immune T cells comprising at least one other edited gene, expressing CD22 CAR.

In a particular embodiment, engineered means that primary immune cells are modified so that they will be endowed with a CD22 CAR, preferably said cells are modified so that they will be endowed with a CD22 CAR and will not die in the presence of purine nucleotide analogs '1 to 5 micromol/L) or in the presence of alemtuzumab (50 microgram/mL). Valton et al., *Molecular Therapy*, vol. 23 no. 9, 1507-1518 September 2015)

Preferably, said T cell is endowed with a CD22 CAR of SEQ ID NO: 15.

More preferably, said T cell is endowed with a CD22 CAR of SEQ ID NO: 15 and comprises at least one sequence of SEQ ID NO: 22.

More preferably, said T cell is endowed with a CD22 CAR of SEQ ID NO: 15 and comprises at least one sequence of SEQ ID NO: 22 and at least part of the sequence.

More preferably, said T cell is endowed with a CD22 CAR of SEQ ID NO: 18 that includes at least one sequence of SEQ ID NO: 20.

The present invention provides a primary immune T cell expressing a CD22 CAR of the invention and exhibiting a CTL and/or degranulating activity towards a CD22-expressing cell.

The present invention also provides a primary T cell expressing a CD22 CAR of the invention for lysing a CD22-expressing cell, in particular a CD22-expressing cancerous cell.

Preferably cells targeted by a T cell endowed with a CD22 CAR of SEQ ID NO: 16 of the invention are efficient in the treatment of relapse/refractory/aggressive ALL or CLL, preferably the present invention also relates to isolated cells or cell lines susceptible to be obtained by said method to engineer cells. In particular said isolated cell comprises at least one CD22 CAR of the invention as described above. In another embodiment, said isolated cell comprises a population of CARs each one comprising different extracellular ligand binding domains. In particular, said isolated cell comprises exogenous polynucleotide sequence encoding CAR. Genetically modified immune cells of the present invention are activated and can proliferate independently of antigen binding mechanisms.

In the scope of the present invention is also encompassed an isolated immune cell, preferably an isolated immune T cell (T-cell), more preferably an engineered isolated immune T cell obtained according to any one of the methods previously described. Said immune cell refers to a cell of hematopoietic origin functionally involved in the initiation and/or execution of innate and/or adaptative immune response. Said immune cell according to the present invention can be derived from a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, a killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes.

Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from an engineered T-cell according to the method described. Modified cells resistant to an immunosuppressive treatment and susceptible to be obtained by the previous method are encompassed in the scope of the present invention.

As a preferred embodiment, the present invention provides T-cells or a population of T-cells endowed with a CD22 CAR of the invention as described above, that do not express functional TCR and that a reactive towards CD22 positive cells, for their adoptive transfer into patients.

As a more preferred embodiment the present invention provides T-cells or a population of T-cells endowed with a CD22 CAR as described above, that do not express functional TCR and that were made resistant to chemotherapy, in particular to purine nucleotide analogues (PNAs).

According to a preferred embodiment of the invention, the immune cells endowed with an CD22 CAR are engineered to be resistant to chemotherapy drugs, in particular to purine nucleotide analogues (PNAs), making them suitable for cancer treatments combining adoptive immunotherapy and chemotherapy.

Purine nucleotide analogues enter chemotherapy compositions for many cancer treatments. It is used as a standard of care against leukemia or lymphoma. The most widely used PNAs are clofarabine, fludarabine and cytarabine alone or in combination. PNAs are metabolized by enzymes having deoxycytidine kinase (dCK) activity [EC 2.7.1.74] into mono, -di and tri-phosphate PNA. Their tri-phosphate forms and particularly clorofarabine triphosphate compete with ATP for DNA synthesis, acts as pro-apoptotic agent and are potent inhibitors of ribonucleotide reductase (RNR), which is involved in trinucleotide production.

The present invention thus includes a method of producing ex-vivo immune cells, preferably primary T-cells expressing no TCR, which are resistant to a purine analogue drug and that can target CD22 positive malignant cells.

A Method for preparing a UCART22 according to the invention can be also that disclosed in WO 2013176915 or in WO 2014191128 which are incorporated herein by reference in entirety.

A method for preparing a UCART22 comprises the following steps:
(a) Providing an immune cell from a donor, preferably an isolated T cell or an isolated population of T cells;
(b) introducing into said immune cell (preferably by transfection or transduction) a nucleic acid sequence encoding a rare-cutting endonuclease specifically targeting:—a gene expressing an enzyme having deoxycytidine kinase activity (dcK—EC 2.7.1.74), in particular the human deoxycytidine kinase gene (NCBI Gene ID: 1633) and/or a gene coding one of the TCR subunit alpha and/or beta, preferably alpha, and/or a gene coding human CD52;
(c) expressing said endonuclease into said immune cells to obtain targeted inactivation of said gene(s);
(d) Expanding the engineered immune cells obtained in step c), optionally in the presence of a purine analogue drug; and
(e) Introducing into said immune cell a CD22 CAR of the invention, preferably of SEQ ID SEQ ID NO:15.

A method for preparing a UCART22 comprises the following steps:
(a) Providing an immune cell from a donor, preferably an isolated T cell or an isolated population of T cells,
(b) introducing into said immune cell (preferably by transfection or transduction) a nucleic acid sequence encoding a rare-cutting endonuclease specifically targeting a gene expressing an enzyme having deoxycytidine kinase activity (dcK—EC 2.7.1.74), in particular the human deoxycytidine kinase gene (NCBI Gene ID: 1633) and/or a gene coding one of the TCR subunit alpha and/or beta, preferably alpha, and/or a gene coding human $\beta_2$ Microglobulin (B2M)l
(c) expressing said endonuclease into said immune cells to obtain targeted inactivation of said gene(s);
(d) Expanding the engineered immune cells obtained in step c), optionally in the presence of a purine analogue drug; and
(e) Introducing into said immune cell a CAR of the invention, preferably a CD22 CAR, alone or in combination with a CD19 CAR, even more preferably a CD22 CAR of SEQ ID NO:15, alone or in combination with a CD19 CAR.

In a preferred embodiment, the present invention includes a method of producing ex-vivo immune cells, preferably primary T-cells expressing no TCR, which are resistant to a purine analogue drug and that can target CD22 positive malignant cells. Said method comprises the following steps:
(a) Providing an immune cell from a donor, preferably an isolated T cell (or an isolated population of T cells);
(b) Introducing into said immune cell a CD22 CAR of the invention, preferably of SEQ ID selected from SEQ ID NO: 15;
(c) Expanding the engineered immune cells obtained in step b);
(d) introducing into said immune cell (by transfection or transduction) a nucleic acid sequence encoding a rare-cutting endonuclease specifically targeting a gene expressing an enzyme having deoxycytidine kinase activity (dcK—EC 2.7.1.74), in particular the human deoxycytidine kinase gene (NCBI Gene ID: 1633) and/or a gene expressing one of the TCR subunit alpha or beta,
(e) expressing said endonuclease into said immune cells to obtain targeted inactivation of said gene(s); and
(f) Expanding the engineered immune cells obtained in step e), optionally in the presence of a purine analogue drug.

The method of producing ex-vivo immune cells, preferably primary T-cells expressing no TCR, which are resistant to a purine analogue drug and that can target CD22 positive malignant cells optionally comprises another step of introducing into said immune cell (by transfection or transduction) a nucleic acid sequence encoding a rare-cutting endonuclease specifically targeting one of the gene cited in Table 1, preferably PD-1, CD279 and more preferably PDCD1 (PD-1, CD279) or CTLA4 (CD152).

The present inventors have successfully created CD22 CAR expressing primary T cells resistant to purine nucleotide analogues (dCK-KO), more particularly to clorofarabine and/or fludarabine, by mediating the inactivation (deletion) of dcK gene expression into said cells particularly by using nucleases, in particular TAL-nucleases.

Transfection of the T-cells using mRNA encoding specific TAL-nuclease directed against dCK genes, preferably by using electroporation as described in WO2013176915, induced a significant resistance to the drugs, while maintaining T-cells cytotoxic activity towards CD22 bearing cells.

The present application also provides a TCR-KO, CD22 CAR (preferably of SEQ ID NO: 15) primary T-cells, which expression of deoxycytidine kinase has been repressed or inactivated (dCK-KO) for the treatment of leukemia or lymphoma, preferably of their aggressive, resistant, relapsing form more preferably B-ALL.

According to a preferred embodiment of the invention, the immune cells endowed with an CD22 CAR are engineered to be resistant to chemotherapy drugs, in particular to alemtuzumab (CAMPATH®), making them suitable for cancer treatments combining adoptive immunotherapy and chemotherapy.

Alemtuzumab is used for many cancer treatments. It is used as a standard of care against leukemia or lymphoma, in particular in the treatment of chronic lymphocytic leukemia (CLL), cutaneous T-cell lymphoma (CTCL) and T-cell lymphoma. It is known under the trade names CAMPATH®, MABCAMPATH® and CAMPATH®-1H. It is also used in some conditioning regimens for bone marrow transplantation, kidney transplantation and islet cell transplantation.

It is a monoclonal antibody that binds to CD52, a protein present on the surface of mature lymphocytes, but not on the stem cells from which these lymphocytes are derived. After treatment with alemtuzumab, these CD52-bearing lymphocytes are targeted for destruction.

Alemtuzumab is also used as second-line therapy for CLL. It was approved by the US Food and Drug Administration for CLL patients who have been treated with alkylating agents and who have failed fludarabine therapy.

The present invention thus includes a method of producing ex-vivo UCART22, thus expressing no TCR, that are resistant to alemtuzumab.

A method for preparing a UCART22 CD52 KO comprises the following steps:
(a) Providing an immune cell from a donor, preferably an isolated T cell or an isolated population of T cells,
(b) introducing into said immune cell (preferably by transfection or transduction) a nucleic acid sequence encoding a rare-cutting endonuclease specifically targeting a gene coding one of the TCR subunit alpha and/or beta, preferably alpha, and/or a gene coding the CD52,
(c) expressing said endonuclease into said immune cells to obtain targeted inactivation of said gene(s);
(d) Expanding the engineered immune cells obtained in step c), optionally in the presence of alemtuzumab,
(e) Introducing into said immune cell a CD22 CAR of the invention, preferably of SEQ ID NO:15.

In a preferred embodiment, the present invention includes a method of producing ex-vivo immune cells, preferably primary T-cells expressing no TCR, which are resistant to alemtuzumab and that can target CD22 positive malignant cells. Said method comprises the following steps:
(a) Providing an immune cell from a donor, preferably an isolated T cell (or an isolated population of T cells);
(b) Introducing into said immune cell a CD22 CAR of the invention, preferably of SEQ ID NO: 15;
(c) Expanding the engineered immune cells obtained in step b);
(d) introducing into said immune cell (by transfection or transduction) a nucleic acid sequence encoding a rare-cutting endonuclease specifically targeting a gene expressing CD52 and a gene expressing one of the TCR subunit alpha or beta;
(e) expressing said endonuclease into said immune cells to obtain targeted inactivation of said gene(s); and
(f) Expanding the engineered immune cells obtained in step e), optionally in the presence of a purine analogue drug.

In one embodiment, a method for preparing a UCART22 comprises the following steps:
(a) Providing an immune cell from a donor, preferably an isolated T cell or an isolated population of T cells;
(b) introducing into said immune cell (preferably by transfection or transduction) a nucleic acid sequence encoding a rare-cutting endonuclease specifically targeting a gene coding one of the TCR subunit alpha and/or beta, preferably alpha, and a nucleic acid encoding a sequence to be inserted, preferably coding HIF-1alpha;
(c) Expressing said endonuclease into said immune cells to obtain targeted insertion of said sequence to be inserted;

(d) Expanding the engineered immune cells obtained in step c), optionally in the presence of low $O_2$ concentration (5% $O_2$, preferably 1% $O_2$); and
(e) Introducing into said immune cell a CD22 CAR of the invention, preferably of SEQ ID SEQ ID NO:15.

In a preferred embodiment, the present invention includes a method of producing ex-vivo immune cells, preferably primary T-cells expressing no TCR, which are resistant to a hypoxia and that can target CD22 positive malignant cells. Said method comprises the following steps:
(a) Providing an immune cell from a donor, preferably an isolated T cell (or an isolated population of T cells);
(b) Introducing into said immune cell a CD22 CAR of the invention, preferably of SEQ ID NO: 15;
(c) Expanding the engineered immune cells obtained in step b);
(d) introducing into said immune cell (preferably by transfection or transduction)—a nucleic acid sequence encoding a rare-cutting endonuclease specifically targeting a gene coding one of the TCR subunit alpha and/or beta, preferably alpha, and a nucleic acid encoding a sequence to be inserted coding HIF-1alpha,
(e) expressing said endonuclease into said immune cells to obtain targeted insertion of said gene(s); and
(f) Expanding the engineered immune cells obtained in step e), optionally in the presence of low $O_2$ concentration (5% $O_2$, preferably 1% $O_2$).

The method of producing ex-vivo immune cells, preferably primary T-cells expressing no TCR, which are resistant to either a purine analogue drug, alemtuzumab or hypoxia and that can target CD22 positive malignant cells optionally comprises another step of introducing into said immune cell (by transfection or transduction) a nucleic acid sequence encoding a rare-cutting endonuclease specifically targeting one of the gene cited in Table 1, preferably (PD-1, CD279) and more preferably PDCD1 (PD-1, CD279) and CTLA4 (CD152).

The present inventors have successfully created CD22 CAR expressing primary T cells resistant to purine nucleotide analogues (dCK-KO), more particularly to clorofarabine and/or fludarabine, by mediating the inactivation (deletion) of dcK gene expression into said cells particularly by using nucleases, in particular TAL-nucleases.

Transfection of the T-cells using mRNA encoding specific TAL-nuclease directed against dCK genes, preferably by using electroporation as described in WO2013176915, induced a significant resistance to the drugs, while maintaining T-cells cytotoxic activity towards CD22 bearing cells.

The same method applies to deletion of human CD52 using specific TALEN® as described by the present inventors.

The present application also provides a TCR-KO, CD22 CAR (preferably of SEQ ID NO: 15) primary T-cells, which expression of deoxycytidine kinase has been repressed or inactivated (dCK-KO) for the treatment of leukemia or lymphoma, preferably of their aggressive, resistant, relapsing form; more preferably relapsing B-ALL.

Such cells are "universal" T cells (or UCART).

In one embodiment, the present application provides a CD22 CAR (preferably of SEQ ID NO: 15) primary T-cells, which expression of deoxycytidine kinase has been repressed or inactivated (dCK-KO) for the treatment of leukemia or lymphoma, preferably of their aggressive, resistant, relapsing form; more preferably relapsing B-ALL after autologous transfer.

In one embodiment, the present application provides a CD22 CAR (preferably of SEQ ID NO: 15) primary T-cells, which expression of CD52 has been repressed or inactivated (CD52-KO) for the treatment of leukemia or lymphoma, preferably of their aggressive, resistant, relapsing form; more preferably relapsing B-ALL after autologous transfer.

In one embodiment, the present application provides a CD22 CAR (preferably of SEQ ID NO: 15) primary T-cells, which expression of HIF-1Alpha has been increased by insertion of the coding sequence into the TRAC sequence without knocking out the TCR for the treatment of leukemia or lymphoma, preferably of their aggressive, resistant, relapsing form; more preferably relapsing B-ALL after autologous transfer.

In one embodiment, the present application provides a CD22 CAR (preferably of SEQ ID NO: 15) primary T-cells, which expression of deoxycytidine kinase and CD52 have been repressed or inactivated (dCK- and CD52KO) for the treatment of leukemia or lymphoma, preferably of their aggressive, resistant, relapsing form; more preferably relapsing B-ALL after autologous transfer.

In one embodiment, the present application provides a CD22 CAR (preferably of SEQ ID NO: 15) primary T-cells, which expression of deoxycytidine kinase and CD52 have been repressed or inactivated (dCK- and CD52KO) and the expression of HIF-1alpha increased by insertion of the HIF1alpha coding sequence into the TRAC sequence without knocking out the TCR, for the treatment of leukemia or lymphoma, preferably of their aggressive, resistant, relapsing form; more preferably relapsing B-ALL after autologous transfer.

The method of producing ex-vivo immune cells, preferably primary T-cells expressing no TCR, which are resistant to a purine analogue drug and/or to alemtuzumab and/or to hypoxia, that can target CD22 positive malignant cells optionally comprises another step of introducing into said immune cell (by transfection or transduction) a nucleic acid sequence encoding a rare-cutting endonuclease specifically targeting one of the gene cited in Table 1, preferably PD-1, CD279 and more preferably PDCD1 (PD-1, CD279) or CTLA4 (CD152).

The present inventors have successfully created CD22 CAR expressing primary T cells resistant to purine nucleotide analogues (dCK-KO), more particularly to clorofarabine and/or fludarabine, by mediating the inactivation (deletion) of dcK gene expression into said cells particularly by using nucleases, in particular TAL-nucleases. The present inventors have successfully created CD22 CAR expressing primary T cells resistant to hypoxia, by a targeted insertion of the HIF-1alpha gene into said cells particularly by using nucleases, in particular TAL-nucleases.

Transfection of the T-cells using mRNA encoding specific TAL-nuclease directed against dCK genes, preferably by using electroporation as described in WO2013176915, induced a significant resistance to the drugs, while maintaining T-cells cytotoxic activity towards CD22 bearing cells.

The present application also provides a TCR-KO, CD22 CAR (preferably of SEQ ID NO: 15) primary T-cells, resistant to hypoxia for the treatment of leukemia or lymphoma, preferably of their aggressive, resistant, relapsing form; more preferably B-ALL.

Activation and Expansion of T Cells

Whether prior to or after genetic modification of the T cells, even if the genetically modified immune cells of the present invention are activated and proliferate independently of antigen binding mechanisms, the immune cells, particularly T-cells of the present invention can be further activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-VIVO™ 5, (Lonza)) that may contain factors necessary for proliferation and viability, including serum (e.g., fetal bovine or human serum), interleukin-2 (IL-2), insulin, IFN-g, IL-4, 1L-7, GM-CSF, IL-10, IL-2, IL-15, TGFβ, and TNF- or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, A1M-V, DMEM, MEM, a-MEM, F-12, X-VIVO™ 1, and X-VIVO™ 20, OPTMIZER®, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Pharmaceutical Compositions

A pharmaceutical composition comprising an engineered (TCR and dCK KO) or (TRAC and CD52 KO) immune T cell expressing a CD22 CAR of the invention (preferably of SEQ ID NO: 15) and a pharmaceutically acceptable vehicle is another object of the present invention.

In another embodiment the present invention provides a composition comprising the UCART22 of the present invention (as any one of the above embodiments) with a compound of the family of the bryostatin compounds, preferably bryostatin-1. Bryostatins are a group of macrolide lactones from bryozoan, *Bugula neritina*. The structure of bryostatin 1 was determined in 1980's. To date 20 different bryostatins have been isolated; further, certain analogs of bryostatin have been referred to as "bryologs". Bryostatins are potent modulators of protein kinase C. (Wender, Paul A., Jeremy L. Baryza, Chad E. Bennett, F. Christopher Bi, Stacey E. Brenner, Michael O. Clarke, Joshua C. Horan, Cindy Kan, Emmanuel Lacôte, Blaise Lippa, Peter G. Nell, and, and Tim M. Turner. The Practical Synthesis of a Novel and Highly Potent Analogue of Bryostatin. *Journal of the American Chemical Society* 2002 124 (46), 13648-13649 DOI: 10.1021/ja027509+)

Examples of bryostatin compounds suitable to be combined with the UCART22 of the invention and methods for preparing these compounds are described in WO2001040214A1 or in EP2737904A2, WO1997034598 incorporated here by reference.

An example of a dose of bryostatin-1 that may be used in combination with the UCART22 of the present invention is as previously described in Varterasian ML1, Mohammad R M, Shurafa M S, Hulburd K, Pemberton P A, Rodriguez D H, Spadoni V, Eilender D S, Murgo A, Wall N, Dan M, Al-Katib A M. Phase II trial of bryostatin 1 in patients with relapsed low-grade non-Hodgkin's lymphoma and chronic lymphocytic leukemia. *Clin Cancer Res.* 2000 March; 6(3): 825-8.

An engineered (TRAC and dCK KO or TRAC and CD52 KO) immune T cell expressing a CD22 CAR of the invention (preferably of SEQ ID NO: 15) [an UCART22] or a pharmaceutical composition comprising said UCART22 is provided as a medicament.

An engineered (TRAC and dCK KO or TRAC and CD52 KO) immune T cell expressing a CD22 CAR of the invention (preferably of SEQ ID NO: 15) [an UCART22] for use in the treatment of cancer or to attenuate inflammation is another object of the present invention.

An engineered (TRAC and dCK KO or TRAC and CD52 KO) immune T cell expressing a CD22 CAR of the invention (preferably of SEQ ID NO: 15) [an UCART22] for use in the treatment of ALL, CLL, relapse refractory aggressive forms of CLL or ALL is another object of the present invention.

An engineered (TRAC and dCK KO or TRAC and CD52 KO) immune T cell expressing a CD22 CAR of the invention (preferably of SEQ ID NO: 15) [an UCART22] for use in the treatment of a CD19 relapse cancer, preferably a CD19 relapse B-ALL is provided.

In another embodiment, hypoxia resistant, engineered (TRAC and dCK KO or TRAC and CD52 KO) immune T cell expressing a CD22 CAR of the invention (preferably of SEQ ID NO: 15) [an UCART22] or a pharmaceutical composition comprising said UCART22 is provided as a medicament.

In another embodiment, hypoxia resistant, engineered (TRAC and dCK KO or TRAC and CD52 KO) immune T cell expressing a CD22 CAR of the invention (preferably of SEQ ID NO: 15) [an UCART22] for use in the treatment of cancer or to attenuate inflammation is another object of the present invention.

In another embodiment hypoxia resistant, engineered (TRAC and dCK KO or TRAC and CD52 KO) immune T cell expressing a CD22 CAR of the invention (preferably of SEQ ID NO: 15) [an UCART22] for use in the treatment of ALL, CLL, relapse refractory aggressive forms of CLL or ALL is another object of the present invention.

In another embodiment hypoxia resistant, engineered (TRAC and dCK KO or TRAC and CD52 KO) immune T cell expressing a CD22 CAR of the invention (preferably of SEQ ID NO: 15) [an UCART22] for use in the treatment of a CD19 relapse cancer, preferably a CD19 relapse B-ALL is provided.

In another embodiment, isolated cell obtained by the different methods of the present invention or cell line derived from said isolated cell can be used as a medicament.

In another embodiment, said medicament can be used for treating cancer, particularly for the treatment of B-cell lymphomas and leukemia in a patient in need thereof. In another embodiment, said isolated cell according to the invention or cell line derived from said isolated cell can be used in the manufacture of a medicament for treatment of a cancer in a patient in need thereof.

The present invention encompasses autologous transfer of engineered cells. In that case cells are isolated from one donor, a human donor, engineered and then transferred to the initial donor in need thereof.

In this particular embodiment, cells may be engineered for example to be resistant to a drug such as alemtuzumab (CAMPATH®) and/or pna and optionally to be resistant to hypoxia.

Therapeutic Applications

The term "cancer" refers to a disease characterized by the uncontrolled growth of one or several types of cells.

Examples of cancers are described herein and, include but are not limited to liquid tumors or hematological cancer.

A hematological cancer according to the present invention may be selected from lymphoma, Hodgkin lymphoma, non-Hodgkin lymphoma, leukemia, multiple myeloma, B-chronic lymphocytic leukemia, hairy cell leukemia, acute lymphocytic leukemia (ALL), and Burkitt's lymphoma, acute lymphocytic cancer, acute myeloid leukemia, preferably a CD22-expressing hematological cancer, more preferably a relapse or refractory CD22-expressing hematological cancer, even more preferably an aggressive form of said CD22-related hematological cancer.

In a preferred embodiment, a relapsed or refractory CD22-expressing hematological cancer is relapsed and/or refractory CD22 expressing or positive B-ALL.

Accordingly, a therapeutically effective amount of UCART22 according to any one of the embodiments described above or a therapeutically effective amount of the pharmaceutical composition as described above is provided for use as a medication for treating a patient suffering a relapsed and/or refractory CD22 expressing or positive B-ALL.

In another embodiment a therapeutically effective amount of UCART22 according to any one of the embodiments described above or a therapeutically effective amount of the pharmaceutical composition as described above is provided for use as a medication for treating a patient suffering a CD22 positive hematological cancer selected from leukemia and lymphoma, hairy cell leukemia, any of acute lymphocytic cancer, acute lymphocytic leukemia (ALL), acute myeloid leukemia, chronic lymphocytic leukemia, B-chronic lymphocytic leukemia, chronic myeloid cancer, Hodgkin lymphoma, non-Hodgkin lymphoma, and Burkitt's lymphoma, multiple myeloma.

In another embodiment a therapeutically effective amount of UCART22 according to any one of the embodiments described above or a therapeutically effective amount of the pharmaceutical composition as described above is provided for use as a medication for treating a patient suffering a CD22 positive cancer selected from alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, cancer of the gallbladder, cancer of the pleura, cancer of the nose, cancer of the nasal cavity, cancer of the middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), hypopharynx cancer, kidney cancer, larynx cancer, liver cancer, lung cancer (e.g., non-small cell lung carcinoma), malignant mesothelioma, mastocytoma, melanoma, nasopharynx cancer, ovarian cancer, pancreatic cancer, peritoneum cancer, omentum cancer, mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer.

Other Examples of CD22-mediated cancers are described herein and, include but are not limited to liver cancer, lung cancer (e.g., non-small cell lung carcinoma), ovarian cancer, pancreatic cancer, thyroid cancer, and urothelial cancer.

In a particular embodiment, the object of the present invention is provided for the treatment of aggressive forms of these cancers, defined as growing at least 2 times faster than the general mean of growth of such cancers in the population.

In one embodiment the objects of the present invention are used in the treatment of leukemia during the accelerated phase of the treatment.

In a particular embodiment, the object of the present invention is provided for the treatment of Refractory/Relapsed Diffuse Large B-Cell Non-Hodgkin's Lymphoma—Breast metastasis in lung-Triple cancer consisting of chronic lymphocytic leukemia with bladder and prostate carcinoma.

Preferably, the cancer is a hematological malignancy (e.g., leukemia or lymphoma, including but not limited to Hodgkin lymphoma, non-Hodgkin lymphoma, chronic lymphocytic leukemia, acute lymphocytic cancer, acute myeloid leukemia, B-chronic lymphocytic leukemia, hairy cell leukemia, acute lymphocytic leukemia (ALL), and Burkitt's lymphoma).

More preferably, the cancer is characterized by the expression of CD22, more preferably, the cancer is characterized by the expression of CD22 by cancerous cells, even more preferably by overexpression of CD22 by cancer cells.

In one embodiment said cancer cells are a relapsed refractory CD19 negative cancer cells.

In one embodiment said cancer cells are a relapsed refractory CD22 expressing cancer cells.

In a preferred embodiment said cancer cells are a relapsed refractory CD19 negative CD22 positive expressing B-ALL. B-cell ALL comprises: early precursor B (early pre-B) ALL (also called pro-B ALL), common ALL, or pre-B ALL. Mature B-cell ALL also called Burkitt leukemia or Non-Hodgkin Lymphoma in Children.

The term "disease associated with expression of CD22" as used herein includes, but is not limited to, a disease associated with expression of CD22 or condition linked to the activity of cells which express CD22 including, tumor cells of various cancers such as, e.g., a CD22 expressing B-ALL.

Cellular destruction by lyse is one of the mechanisms whereby the CD22 CAR T cells of the invention acts against CD22-expressing cells, reducing or eliminating tumors, facilitating infiltration of immune cells of the hosts to the tumor site, and enhancing/extending anti-tumor responses.

In another aspect, the present invention relies on methods for treating patients in need thereof, said method comprising at least one of the following steps: providing an UCART22 of the invention and administrating said transformed immune cells to said patient, In one embodiment, said UCART22 cells of the invention can undergo robust in vivo T cell expansion and can persist for an extended amount of time in the host.

In another aspect, the present invention provides methods for treating patients in need thereof, said method comprising at least one of the following steps: conditioning a patient suffering a cancer, providing an UCART22 of the invention, and administrating said transformed immune cells to said patient. Conditioning includes lymphodepletion, or any appropriate conditioning a skilled person, preferably also a medical doctor, will recognize as determinant for curing said patient.

In a preferred embodiment said method further comprises a step of bone marrow transplantation.

In one embodiment, said UCART22 cells of the invention can undergo robust in vivo T cell expansion and can persist for an extended amount of time in the host.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

In one embodiment, survival of said T cells of the invention in the host is controlled using an anti CD20 (rituximab) and/or QBEND-10 treatment.

Subject

Compositions and methods of the present invention may be used to treat a subject who has been characterized as having pathological cells or tissues expressing CD22, or is suspected of having pathological cells or tissues expressing CD22. For example, subjects benefiting from treatment according to the invention include subjects with B-ALL or CLL, refractory BALL, relapse B-ALL.

In a preferred embodiment the patients are children suffering BALL, relapsed BALL, refractory BALL (pediatric indication).

The treatment with the engineered immune cells according to the invention may be in combination with one or more therapies against cancer selected from the group of antibodies therapy, chemotherapy, cytokines therapy, dendritic cell therapy, gene therapy, hormone therapy, laser light therapy and radiation therapy.

Accordingly, the present invention provides a pharmaceutical composition comprising a therapeutically active amount of UCART22 for the treatment of children suffering BALL, relapsed BALL, refractory BALL.

The present invention also provides a pharmaceutical composition comprising a UCART22 and a pharmaceutically acceptable excipient for the treatment of children suffering BALL, relapsed BALL, refractory BALL.

In a preferred embodiment, a pharmaceutical composition comprises the UCART22 of the invention and a compound of the bryostatin family, preferably bryostatin-1 and a pharmaceutically acceptable excipient for the treatment of children suffering BALL, relapsed BALL, refractory BALL.

According to a preferred embodiment of the invention, said treatment can be administrated into patients undergoing an immunosuppressive treatment, (conditioning treatment), more preferably a lymphodepletion. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment or lymphodepletion should help the selection and expansion of the T-cells according to the invention within the patient and destruction of CD22 cancerous cells.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administered in one or more doses, preferably several successive doses (redosing) to avoid escaping (relapsed cells). In another embodiment, said effective amount of cells are administrated as a single dose or in to doses. In another embodiment, said effective amount of cells are administrated as more than one dose over a period time.

Timing of administration is within the judgment of managing physician and depends on the clinical condition of the patient.

The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

The present UCART22 are design to be efficient but for being not to active and limit cytokine storm. In case of overresponding patients, the present invention may be combined with adequate medication for preventing of blocking cytokine storm such as anti-IL-6 drugs.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH®, alemtuzumab, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993).

In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH®. In another embodiment, the cell compositions of the present invention are administered following B-cell ablative therapy such as agents that react with CD20, e.g., RITUXAN® (rituximab) or QBEND-10. For example, in one embodiment, subjects may undergo standard treatment with high dose chemotherapy followed by peripheral blood cell transplantation. In certain embodiments, following the transplant, subjects receive an infusion of the expanded immune cells of the present invention. In an additional embodiment, expanded cells are administered before or following surgery.

In another embodiment, following the transplant, subjects receive an agent that reacts with CD20, e.g., RITUXAN®, or Rituximab, preferably with an agent that reacts with CD22 and CD20.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFvFc) fused to the intracellular signaling domain of the T cell antigen receptor complex zeta chain (scFvFc:ζ) and have the ability, when expressed in T cells, to redirect antigen recognition based on the monoclonal antibody's specificity. One example of CAR used in the present invention is a CAR directing against CD22 antigen and can comprise as non-limiting example the amino acid sequences: any one of SEQ ID NO: 15 to 18, preferably SEQ ID NO: 16 or 18, more preferably SEQ ID NO: 16.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp. Rare-cutting endonucleases significantly increase HR by inducing DNA double-strand breaks (DSBs) at a defined locus (Perrin, Buckle et al. 1993; Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005), a Cas9 endonuclease from CRISPR system (Gasiunas, Barrangou et al. 2012; Jinek, Chylinski et al. 2012; Cong, Ran et al. 2013; Mali, Yang et al. 2013) or a chemical endonuclease (Eisenschmidt, Lanio et al. 2005; Arimondo, Thomas et al. 2006). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

By a "TALE-nuclease" (TALEN®) is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance I-TevI, ColE7, NucA and Fok-I. In a particular embodiment, the TALE domain can be fused to a meganuclease like for instance I-CreI and I-OnuI or functional variant thereof. In a more preferred embodiment, said nuclease is a monomeric TALE-Nuclease. A monomeric TALE-Nuclease is a TALE- Nuclease that does not require dimerization for specific recognition and cleavage, such as the fusions of engineered TAL repeats with the catalytic domain of I-TevI described in WO2012138927. Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALE-nuclease have been already described and used to stimulate gene targeting and gene modifications (Boch, Scholze et al. 2009; Moscou and Bogdanove 2009; Christian, Cermak et al. 2010; Li, Huang et al. 2011). Custom-made TAL-nucleases are commercially available under the trade name TALEN™ (Cellectis, 8 rue de la Croix Jarry, 75013 Paris, France).

The rare-cutting endonuclease according to the present invention can also be a Cas9 endonuclease, Zinc finger endonuclease, MegaTAL endonuclease. The genome engineering tool has been developed based on the RNA-guided Cas9 nuclease (Gasiunas, Barrangou et al. 2012; Jinek, Chylinski et al. 2012; Cong, Ran et al. 2013; Mali, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the proto-spacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracr RNA:crRNA structure acts as guide RNA that directs the endonuclease Cas9 to the cognate target sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif—PAM). Following pairing between the dual-RNA and the target sequence, Cas9 subsequently introduces a blunt double strand break 3 bases upstream of the PAM motif (Garneau, Dupuis et al. 2010).

Rare-cutting endonuclease can be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease.

Preferred homing endonuclease according to the present invention can be an I-CreIvariant.

By "delivery vector" or "delivery vectors" is intended any delivery vector which can be used in the present invention to put into cell contact (i.e., "contacting") or deliver inside cells or subcellular compartments (i.e., "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adeno-associated viruses, in particular aav6), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as nonlimiting example, that are able to integrate the genome of a target cell. At the opposite by "non-integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; HUVEC cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty-five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

"Identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. CD28 is excluded from this list. A co-stimulatory ligand also encompasses, inter alia, an antibody that specifically binds with a co-stimulatory molecule present on a T cell, such as but not limited to, CD27, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus, examples of cell surface markers that may act as ligands include those associated with viral, bacterial and parasitic infections, autoimmune disease and cancer cells.

The term "subject" or "patient" as used herein includes all members of the animal kingdom including non-human primates and humans, preferably human. In one embodiment patients are patients with aggressive, or refractory or relapsing ALL, or, aggressive, refractory, relapsing CLL.

A mammal is any warm-blooded vertebrate of the class Mammalia, preferably a human.

"Suicide domain or switches," or safety on-and-off switches" means a domain usually a cell surface domain recognized by a molecule, protein, chemical, antibody for immunoselecting expressing cells and eventually controlling their functioning and survival.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

General Method
Screening and Selection of CAR
Primary T-Cell Cultures

T cells were purified from Buffy coat samples provided by EFS (Etablissement Frangais du Sang, Paris, France) using FICOLL® gradient density medium. The PBMC layer was recovered. T cells were activated in X-VIVO™-15 medium (Lonza) supplemented with 20 ng/mL Human IL-2, 5% Human, and DYNABEADS® Human T activator CD3/CD28 at a bead:cell ratio 1:1 (Life Technologies).

CAR mRNA Transfection

Transfections of CAR mRNAs encoding each CAR constructs were done at Day 4 or Day 11 after T-cell purification and activation. Cells were immediately diluted in X-VIVO™-15 media and incubated at 37° C. with 5% $CO_2$. IL-2 was added 2 h after electroporation at 20 ng/mL.

T-Cell Transduction

Vectors coding a CD22 CAR are introduced into T cells as previously described.

CAR detection at the surface of T-cells is performed using a recombinant protein consisting on the extracellular domain of the human CD22 protein (whole protein, distal portion of CD22 or proximal portion of CD22) fused together with a murine IgG1 Fc fragment. Binding of this protein to the CAR molecule is detected with a PE-conjugated secondary antibody (Jackson Immunoresearch) targeting the mouse Fc portion of the protein and analyzed by flow cytometry.

Inactivation of Specific Gene(s) in Primary T Cells

Inactivation of specific gene(s) in primary T cells may be performed before preferably after CD22 CAR introduction into cells using endonucleases such as TAL endonuclease, optionally Crispr Cas 9 endonucleases, designed accordingly. At least one gene is inactivated, one, two or three genes may be inactivated in one step or in several successive step. In a preferred embodiment two genes are inactivated, preferably TCRalpha gene and a gene which deletion confers resistance to a drug selected from purine nucleotide analogues, alemtuzumab, platines (cisplatine or carboplatine), anti-topoisomerase I (Irinotecan), anti-topoisomerase II (Etoposide), Methotrexate (folic acid analogs), preferably purine nucleotide analogues, alemtuzumab.

In general, heterodimeric nuclease, in particular TALE-Nuclease targeting two long sequences (called half targets) separated by a spacer within a target gene is designed and produced.

Each TALE-nuclease construct may be cloned in an appropriate mammalian expression vector. mRNA encoding TALE-nuclease cleaving a targeted genomic sequence may be synthesized from plasmid carrying the coding sequence downstream a promoter. Purified T cells preactivated with anti-CD3/CD28 coated beads are used and transfected with each of the 2 mRNAs encoding both half TALE-nucleases. Cells may be reactivated with soluble anti-CD28 to measure cell proliferation for various times and the activation marker CD25 detected to assess the activation state of the cells.

Degranulation Assay (CD107a Mobilization)

Cells were incubated in 96-well plates, together with an equal amount of cells expressing various levels of the targeted protein (CD22). Co-cultures were maintained for 6 hours at 37° C. with 5% $CO_2$. CD107a staining was done during cell stimulation, by the addition of a fluorescent anti-CD107a antibody at the beginning of the co-culture, together with an anti-CD49d, anti-CD28, and 1x Monensin solution, as a control. After the 6 h incubation period, cells were stained with a fixable viability dye and fluorochrome-conjugated anti-CD8 and analyzed by flow cytometry. The degranulation activity was determined as the % of CD8+/CD107a+ cells, and by determining the mean fluorescence intensity signal (MFI) for CD107a staining among CD8+ cells. Degranulation assays were carried out 24 h after mRNA transfection.

IFN Gamma Release Assay 24 h after mRNA transfection, CD22 CAR expressing T-cells were incubated together with cell lines expressing various levels of the targeted protein for 24 hours at 37° C. The supernatants were recovered and IFN gamma detection in the cell culture supernatants was done by ELISA assay.

Cytotoxicity Assay

Cells were incubated together with target cells (expressing different levels of CD22) or (negative control) cells. Target and control cells were labelled with fluorescent intracellular dyes (CFSE or CELLTRACE™ Violet) before co-culturing them with CAR+ T-cells. The co-cultures were incubated for 4 hours at 37° C. After this incubation period, cells were labelled with a fixable viability dye and analyzed by flow cytometry. Viability of each cellular population (target cells or negative control cells) was determined and the % of specific cell lysis was calculated. Cytotoxicity assays were carried out 48 h after mRNA transfection.

Anti-Tumor Mouse Model

Immunodeficient mice are implanted with tumor cells (CD22 BALL from patients) or with targeted protein expressing -Luciferase cells into the flank. Subsequently, cells were implanted into mouse brains. Serial transplantation into further generations of mice continues the maintenance of in vivo xenograft cell lines. Optionally, mice received an anti-cancer treatment before/or together with injection with CAR+ T-cells (alemtuzumab and/or flu). Mice are then iv injected (either 2 or 7 days after injection of the tumor cell line) with different doses of CAR+ T-cells to be tested, or with T-cells that were not expressing CD22CAR. Bioluminescent signals are determined at the day of T-cell injection (DO), at D7, 14, 21, 28 and 40 after T-cell injection in order to follow tumoral progression in the different animals.

Phase I dose-escalation study to evaluate the safety, expansion and persistence of allogeneic CD22 CART (UCART22) in patients with relapsed or refractory or MRD+ CD22+ B-cell acute lymphoblastic leukemia (B-ALL)

Background and Rationale

With the current multi-drug chemotherapy regimens, long term survival is seen in >80% of childhood acute lymphoblastic leukemia (ALL) and in approximately 40% of adult ALL.(1) Further intensification of chemotherapy has not proved to be effective.(2) There has been significant advancement in our understanding of the biology of ALL in the last few years which provides an opportunity for 'targeted therapy'.(3, 4).

Relapse/refractory ALL remains a challenging disease. Post-relapse therapies will lead to a second CR (CR2) in 30-40% of patients with a 5-year OS of only around 10%. In the largest report of relapsed adult ALL patients to date, Fielding and colleagues analyzed the outcomes of relapsed adult ALL patients who were treated on the MRC UKALLXII/ECOG E2993 trial. Of the 1508 evaluable patients, 1372 (91%) achieved CR1 of whom 609 (44% of the CR1 patients) relapsed at a median of 11 months. The κ-year OS was only 7% for the relapsed patients. The median OS for the relapsed patients was 5.5 months. Tavernier and colleagues reported outcomes of 421 ALL patients who experienced first relapse treated on the French LALA-94 trial. A CR2 was achieved in 44% patients with a median DFS of 5.2 months and median OS of 6.3 months. Oriol and colleagues reported the outcomes of 263 ALL patients in first relapse treated on 4 consecutive PETHEMA trials. CR2 was achieved in 45% of patients, a rate similar to the French LALA trials. The median OS was after relapse was 4.5 months with a 5-year OS of 10%.

CD22 expression occurs in >90% of patients with ALL, and is a valid therapeutic target. Cellular therapies such as chimeric antigen receptor (CAR) T cell therapies are increasingly being used to treat patients with hematologic malignancies.(8-16) In patients with relapsed acute lymphoblastic leukemia (ALL), a very high complete response rate (80-90%) have been reported with autologous CD19-CART cells.(12) Similarly, response rate of 40-50% is seen in patients with relapsed chronic lymphocytic leukemia (CLL) undergoing autologous CD19 CART therapies.(9)

The present study evaluates allogeneic CART cells directed to CD22 in patients with relapsed and/or refractory CD22 B-ALL.

Objectives

Primary Objectives

To evaluate the safety and tolerability of allogeneic CD22 CART and to determine the maximum tolerated dose (MTD)

Secondary Objectives

To determine the efficacy of allogeneic CD22 CART

To determine the incidence of GVHD

Exploratory Objectives

To determine the expansion, phenotype, trafficking and persistence of infused CART cells Inclusion Criteria Relapsed or refractory CD22-positive ALL (For expansion phase: patients with MRD+ disease are allowed)

Patients aged≥2 years

ECOG performance status≤2

Normal organ function including bilirubin≤2 mg/dl, ALT/AST<3×ULN, and creatinine≤2 mg/dl Left Ventricle Ejection Fraction (LVEF)≥40%

Exclusion Criteria

Patient is pregnant or breastfeeding

Patients with uncontrolled active infections

Isolated extramedullary relapse (i.e. testicular, CNS)

Known active CNS leukemia. Note: Patients with history of CNS disease that has been effectively treated will be eligible provided that they have been in CNS remission>4 weeks before enrollment Active hepatitis B or active hepatitis C HIV infection Active GVHD requiring systemic steroid therapy. Steroid therapy for physiologic replacement is acceptable.

Received a DLI within 4 weeks of CD22 CART infusion

Allo-SCT within 60 days of CD22 CART infusion

Description of Study

This is Phase I study. There are 2 phases to this trial. Dose escalation, and Dose expansion.

Patients receive CD22 allogeneic CART after receiving lymphodepletion chemotherapy.

Dose-escalation: Four dose levels are studied in a standard 3×3 design (Table 12). A total of 9-18 patients are be enrolled.

TABLE 12

| | |
|---|---|
| −1 | $1 \times 10^4$ |
| 1 (Starting dose) | $1 \times 10^5$ |
| 2 | $1 \times 10^6$ |
| 3 | $5 \times 10^6$ |

Once the R2PD level is identified, dose-expansion starts.

A total of 20 patients are then enrolled (10 R/R ALL; 10 MRD+ post-SCT).

Total sample size: 29-38 patients

TABLE 13

| Number of Patients with DLT at a Dose Level | Decision |
|---|---|
| 0 of 3 | Escalate and evaluate in 3 subsequent patients. |
| 1 of 3 | Enroll 3 additional subjects at this dose level. |
| >/=2 of 3 | The MTD has been exceeded. Dose escalation will stop and this level will be declared the maximum administered dose. Evaluate 3 additional patients at the prior dose level if only three were treated at that dose previously. |
| 1 of 6 | Escalate dose and evaluate in 3 subsequent patients. |
| </=1 out of 6 at the Highest Dose Below the Maximum Administered Dose | This is the MTD. |
| >/=2 of 6 | The MTD has been exceeded. Dose escalation will stop and this level will be declared the maximum administered dose. Evaluate 3 additional patients at the prior dose level if only three were treated at that dose previously. |

The second study compares allogeneic CART cells directed to CD22 to allogeneic CART cells directed to CD22 and CD19 (2 forms) in patients with CD19+CD22+B-ALL.

Objectives

Primary Objectives

To evaluate the safety and tolerability of allogeneic CD19+CD22 CART and to determine the maximum tolerated dose (MTD)

Secondary Objectives

To determine the efficacy of allogeneic CD22 CART

To determine the incidence of GVHD

Exploratory Objectives

To determine the expansion, phenotype, trafficking and persistence of infused CART cells Inclusion Criteria Relapsed or refractory CD22-positive ALL (For expansion phase: patients with MRD+ disease are allowed)

Patients aged≥2 years

ECOG performance status≤2

Normal organ function including bilirubin≤2 mg/dl, ALT/AST<3×ULN, and creatinine≤2 mg/dl Left Ventricle Ejection Fraction (LVEF)≥40%

Exclusion Criteria

Patient is pregnant or breastfeeding

Patients with uncontrolled active infections

Isolated extramedullary relapse (i.e. testicular, CNS)

Known active CNS leukemia. Note: Patients with history of CNS disease that has been effectively treated will be eligible provided that they have been in CNS remission>4 weeks before enrollment Active hepatitis B or active hepatitis C HIV infection Active GVHD requiring systemic steroid therapy. Steroid therapy for physiologic replacement is acceptable.

Received a DLI within 4 weeks of CD22 CART infusion

Allo-SCT within 60 days of CD22 CART infusion

Description of Study

This is Phase I study. There are 2 phases to this trial. Dose escalation, and Dose expansion.

Patients receive CD22 allogeneic CART after receiving lymphodepletion chemotherapy.

Dose-escalation: Four dose levels are studied in a standard 3×3 design (Table 14). A total of 9-18 patients are be enrolled.

TABLE 14

| Dose Level | |
|---|---|
| −1 | $1 \times 10^4$ |
| 1 (Starting dose) | $1 \times 10^5$ |
| 2 | $1 \times 10^6$ |
| 3 | $5 \times 10^6$ |

Once the R2PD level is identified, dose-expansion starts.

A total of 20 patients are then enrolled (10 R/R ALL; 10 MRD+ post-SCT).

Total sample size: 29-38 patients

TABLE 15

| Number of Patients with DLT at a Dose Level | Decision |
|---|---|
| 0 of 3 | Escalate and evaluate in 3 subsequent patients. |
| 1 of 3 | Enroll 3 additional subjects at this dose level. |
| >/=2 of 3 | The MTD has been exceeded. Dose escalation will stop and this level will be declared the maximum administered dose. Evaluate 3 additional patients at the prior dose level if only three were treated at that dose previously. |
| 1 of 6 | Escalate dose and evaluate in 3 subsequent patients. |
| </=1 out of 6 at the Highest Dose Below the Maximum Administered Dose | This is the MTD. |
| >/=2 of 6 | The MTD has been exceeded. Dose escalation will stop and this level will be declared the maximum administered dose. Evaluate 3 additional patients at the prior dose level if only three were treated at that dose previously. |

REFERENCES

1. Inaba H, Greaves M, Mullighan C G. Acute lymphoblastic leukaemia. Lancet. 2013; 381(9881):1943-55.
2. Faderl S, Thomas D A, O'Brien S, Ravandi F, Garcia-Manero G, Borthakur G, et al. Augmented hyper-CVAD based on dose-intensified vincristine, dexamethasone, and asparaginase in adult acute lymphoblastic leukemia salvage therapy. Clin Lymphoma Myeloma Leuk. 2011; 11(1):54-9.
3. Mullighan C G. Genome sequencing of lymphoid malignancies. Blood. 2013; 122(24):3899-907.
4. Mullighan C G. Genomic characterization of childhood acute lymphoblastic leukemia. Semin Hematol. 2013; 50(4):314-24.
5. Fielding A K, Richards S M, Chopra R, Lazarus H M, Litzow M R, Buck G, et al. Outcome of 609 adults after relapse of acute lymphoblastic leukemia (ALL); an MRC UKALL12/ECOG 2993 study. Blood. 2007; 109(3):944-50.
6. Tavernier E, Boiron J M, Huguet F, Bradstock K, Vey N, Kovacsovics T, et al. Outcome of treatment after first relapse in adults with acute lymphoblastic leukemia initially treated by the LALA-94 trial. Leukemia: official journal of the Leukemia Society of America, Leukemia Research Fund, U. K. 2007; 21(9):1907-14.
7. Oriol A, Vives S, Hernandez-Rivas J M, Tormo M, Heras I, Rivas C, et al. Outcome after relapse of acute lymphoblastic leukemia in adult patients included in four consecutive risk-adapted trials by the PETHEMA Study Group. Haematologica. 2010; 95(4):589-96.
8. Kochenderfer J N, Wilson W H, Janik J E, Dudley M E, Stetler-Stevenson M, Feldman S A, et al. Eradication of B-lineage cells and regression of lymphoma in a patient treated with autologous T cells genetically engineered to recognize CD19. Blood. 2010; 116(20):4099-102.
9. Porter D L, Levine B L, Kalos M, Bagg A, June C H. Chimeric antigen receptor-modified T cells in chronic lymphoid leukemia. N Engl J Med. 2011; 365(8):725-33.
10. Brentjens R J, Davila M L, Riviere I, Park J, Wang X, Cowell L G, et al. CD19-targeted T cells rapidly induce molecular remissions in adults with chemotherapy-refractory acute lymphoblastic leukemia. Sci Transl Med. 2013; 5(177):177ra38.

11. Grupp S A, Kalos M, Barrett D, Aplenc R, Porter D L, Rheingold S R, et al. Chimeric antigen receptor-modified T cells for acute lymphoid leukemia. N Engl J Med. 2013; 368(16):1509-18.
12. Maude S L, Teachey D T, Porter D L, Grupp S A. CD19-targeted chimeric antigen receptor T-cell therapy for acute lymphoblastic leukemia. Blood. 2015; 125(26): 4017-23.
13. Park J H, Geyer M B, Brentjens R J. CD19-targeted CAR T-cell therapeutics for hematologic malignancies: interpreting clinical outcomes to date. Blood. 2016; 127 (26):3312-20.
14. Lee D W, Kochenderfer J N, Stetler-Stevenson M, Cui Y K, Delbrook C, Feldman S A, et al. T cells expressing CD19 chimeric antigen receptors for acute lymphoblastic leukaemia in children and young adults: a phase 1 dose-escalation trial. Lancet. 2015; 385(9967):517-28.
15. Kochenderfer J N, Dudley M E, Kassim S H, Somerville R P, Carpenter R O, Stetler-Stevenson M, et al. Chemotherapy-refractory diffuse large B-cell lymphoma and indolent B-cell malignancies can be effectively treated with autologous T cells expressing an anti-CD19 chimeric antigen receptor. J Clin Oncol. 2015; 33(6):540-9.
16. Kebriaei P, Singh H, Huls M H, Figliola M J, Bassett R, Olivares S, et al. Phase I trials using Sleeping Beauty to generate CD19-specific CAR T cells. J Clin Invest. 2016; 126(9):3363-76.

EXAMPLES

Example 1

Proliferation of TCR Alpha Inactivated Cells Expressing a CD22-CAR.

Heterodimeric TALE-nuclease targeting two 17-bp long sequences (called half targets) separated by an 15-bp spacer within T-cell receptor alpha constant chain region (TRAC) gene were designed and produced. Each half target is recognized by repeats of the half TALE-nucleases listed in Table 16.

TABLE 16

TAL-nucleases targeting TCRalpha gene

| Target | Target sequence | Repeat sequence | Half TALE-nuclease |
|---|---|---|---|
| TRAC_T01 | TTGTCCCACAGATATCC Agaaccctgaccctg | Repeat TRAC_T01-L | TRAC_T01-L TALEN ® (SEQ ID NO: 16) |
| | CCGTGTACCAGCTGAGA (SEQ ID NO: 18) | Repeat TRAC_T01-R | TRAC_T01-R TALEN ® (SEQ ID NO: 17) |

Each TALE-nuclease construct was subcloned using restriction enzyme digestion in a mammalian expression vector under the control of the T7 promoter. mRNA encoding TALE-nuclease cleaving TRAC genomic sequence were synthesized from plasmid carrying the coding sequence downstream from the T7 promoter.

Purified T cells preactivated during 72 hours with anti-CD3/CD28 coated beads were transfected with each of the 2 mRNAs encoding both half TRAC_T01 TALE-nucleases. 48 hours post-transfection, different groups of T cells from the same donor were respectively transduced with a vector encoding one of the CD22 CAR of the invention. 2 days post-transduction, $CD3_{NEG}$ cells were purified using anti-CD3 magnetic beads and 5 days post-transduction cells were reactivated with soluble anti-CD28 (5 µg/ml).

Cell proliferation was followed for up to 30 days after reactivation by counting cell 2 times per week. The proliferation in TCR alpha inactivated cells expressing the CD22 CARs, was comparable to that of non inactivated cells and increased especially when reactivated with anti-CD28.

Multiple transfection of TALEN® mRNA mRNAs encoding the TRAC TALEN®s (Left and right) and mRNAs encoding TALEN® pairs specific for the B2M gene were transfected in activated T cells, and subsequently transduced with exogenous polynucleotides encoding a CAR specific for CD22 or a CAR specific for CD19 or both.

Double KO TRAC and B2M or CD56 gene expressed undetectable level of TCR and MHCI or TCR and CD56. After purification, cells were transduced again.

Example 2

CD22 CAR-T

Development of engineered CAR T-cells targeting CD22, for the treatment of refractory, relapsing or aggressive ALL or CLL.

CD22 CARs: (FIG. 2)

Construct as m971 and m971 variants with decreased affinity for CD22 and high selectivity CD22 CARs were designed and prepared using different scFv. The m971 scFv is derived from 971 antibody (Haso W[1], Lee D W, Shah N N, Stetler-Stevenson M, Yuan C M, Pastan I H, Dimitrov D S, Morgan R A, FitzGerald DJ, Barrett D M, Wayne A S, Mackall C L, Orentas R J. Anti-CD22-chimeric antigen receptors targeting B-cell precursor acute lymphoblastic leukemia. Blood. 2013 Feb. 14; 121(7):1165-74. doi: 10.1182/blood-2012-06-438002. Epub 2012 Dec. 14)

A CARs architecture (FIG. 2) was constructed with the 41BB costimulatory domain, the CD3 activation domain, the CD8α transmembrane domain and a hinge, CD8α hinge (SEQ-ID N° 15). The construction comprising a FcγRIIIα-hinge correspond to (SEQ-ID NO: 14).

Constructs were inserted into a vector for stable expression and screening of designed CARs.

CD22 CARs were m971-V3 CAR (SEQ ID NO.22); and SEQ ID NO: 24.

Sequences may be also optimized for CD22 binding and the treatment of ALL and CLL, preferably their refractory relapsing and aggressive forms.

CAR Expression

CD22 CARs were introduced into primary KO TCR T cells 5 days after activation by anti-CD3CD28 coated beads and IL-2. CAR expression was assessed by flow cytometry. All CAR were expressed at the cell surface. Activity towards CD22+ transformed cell lines and refractory or relapsed CD22+ B ALL from patients.

To test the functionality of the anti-CD22 CARs, B Cell expressing CD22 (ALL lines REH, SEM, NALM6-GL, KOPN8, Daudi, Raji, and on K562 were used (see Haso et al., 2013, 2013; Blood: 121 (7): 1165-1174 for experimental details). refractory or relapsed CD22+ B ALL were obtained from patients.

As expected, all cells expressing CD22 were positively stained and targeted by the CD22 CAR from m971 of the invention, as with the CD22 CAR (scfv2 from HA22).

Degranulation Assay

Figure 5:
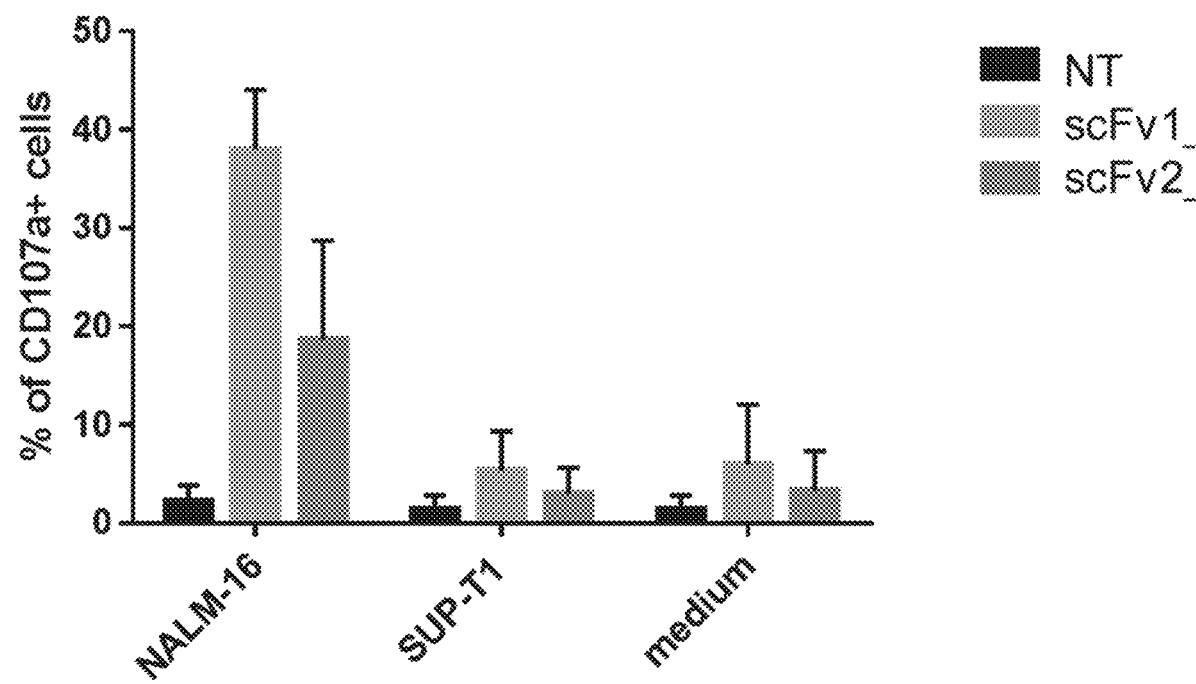
FIG. 5: Degranulating activity of UCART22. Degranulating activity of UCART22 (scfv-V1 against the proximal domain of CD22) as compared to the degranulating activity of non-transduced (NT) or that of T cells transduced with a CAR targeting the distal part of CD22 (scfv-V2), in the presence of CD22-positive NALM-16 cells as compared to CD22 negative SUP-T1 cells.

To validate the CD22 CAR constructs a degranulation assay was performed on target cells with T cells expressing the CD22 CAR of the invention. The CART degranulation was evaluated by flow cytometry. The read-out is the CD107a expression at the T cell plasma membrane after 5 hours incubation with target cells. The results showed that degranulation was more important from the CARm971-(scfv-1) than for CD22 CAR T cells against the distal part of the CD22 (SEQ ID 20) scfv-2 (FIG. 5).

Cytotoxicity Assay

Figure 6:
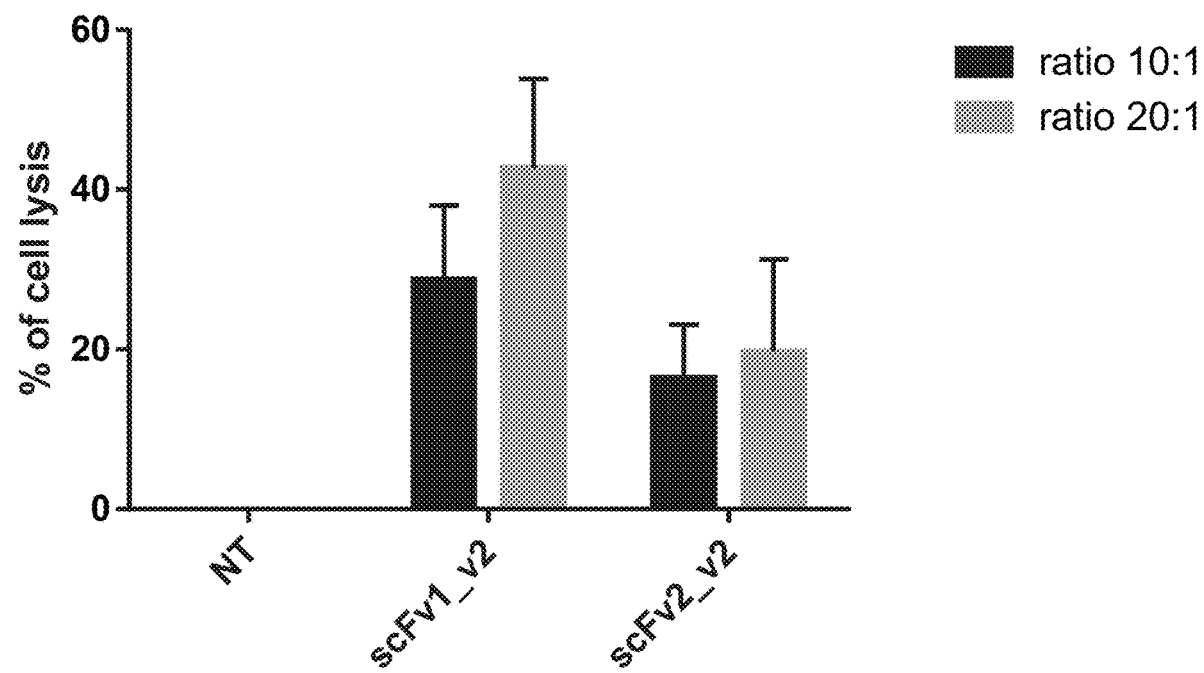
FIG. 6: Cytotoxic activity of UCART22. Cytotoxic activity of UCART22 (scfv-V1 against the proximal domain of CD22) as compared to the cytotoxic activity of non-transduced (NT) or that of T cells transduced with a CAR targeting the distal part of CD22 (scfv-V2) cells in the presence of CD22-positive NALM-16 cells as compared to CD22 negative SUP-T1 cells.

A cytotoxicity assay was performed on these same target cells with T cells expressing CD22 CARs of the invention. CD22 CARs, showed a strong specific lysis of CD22 cells of UCART22 of the invention as compared to cells expressing a scFv against the distal part of CD22 (scfv2) (FIG. 6).

Interferon Gamma Assay

Figure 7:
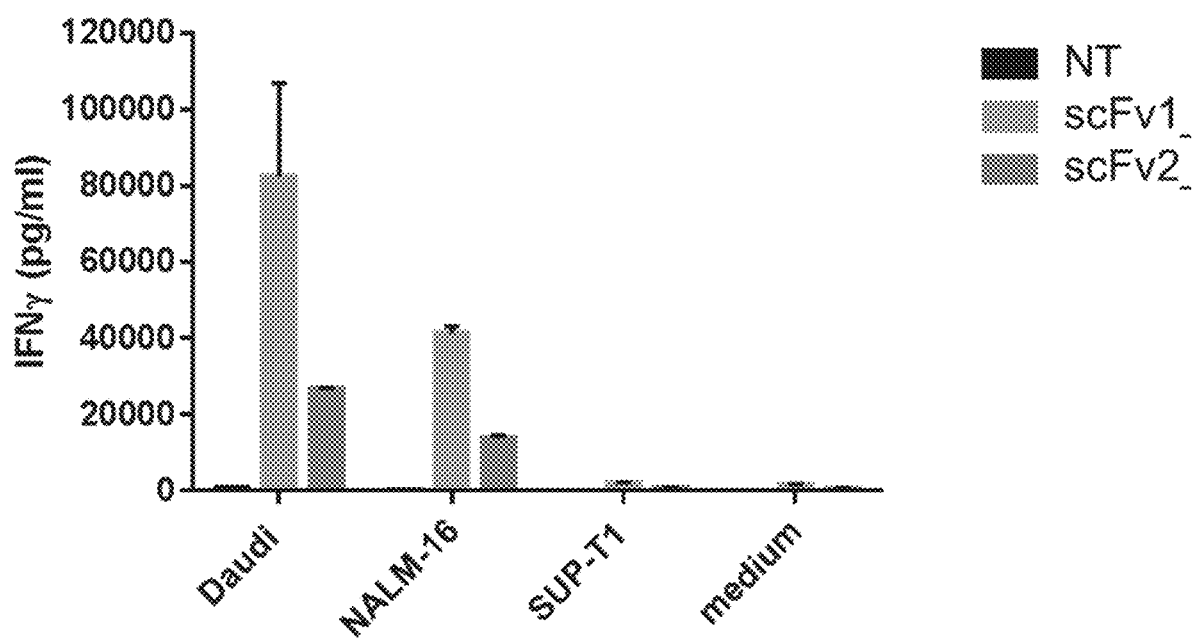
FIG. 7: Interferon gamma production of UCART22.

Interferon gamma production of UCART22 (scfv-V1 against the proximal domain of CD22) as compared to that of non-transduced (NT) or of T cells transduced with a CAR targeting the distal part of CD22(scfv-V2) cells in the presence of CD22-positive NALM-16 cells as compared to CD22 negative SUP-T1 cells (FIG. 7).

Mice Survival

Figure 8:
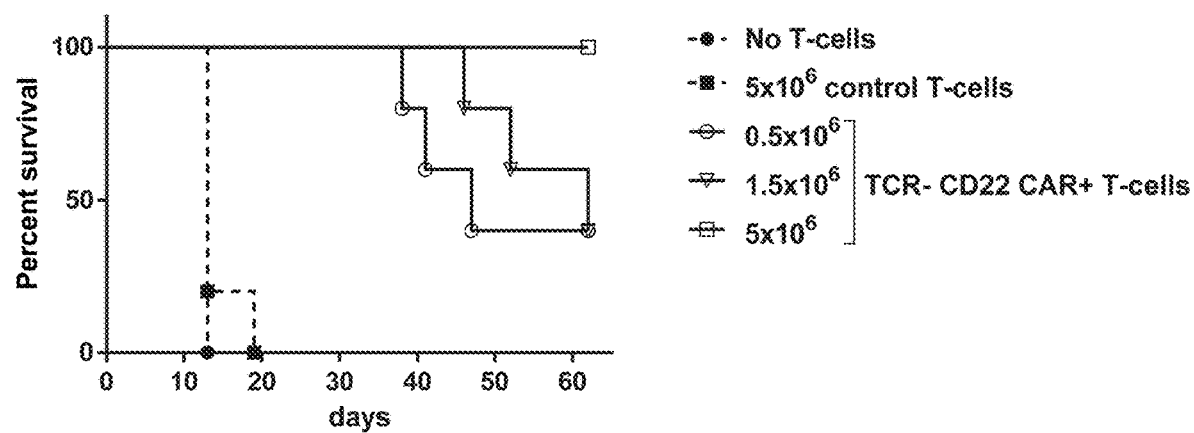
FIG. 8: Mice survival in the presence of control cells, UCART22 (scfv-V1 against the proximal domain of CD22) or CART22 (no TRAC deletion).

Mice survival was improved in the presence UCART22 (scfv-V1 against the proximal domain of CD22) or CART22 (no TRAC inactivation) as compared to control cells (FIG. 8).

Resistance to Hypoxia and/or Drugs

Engineered cells UCART22 of the invention were not significantly affected (survival and CTL activity) in the presence of alemtuzumab (50 micrograms/mL), or PNA (flu) as compared to non-engineered cells sensitive cells which died 48 hours following addition of the drug in the cell culture, or following culture condition under hypoxia (less than 5%, preferably less than 1% $O_2$).

Tests performed under low $O_2$ condition (<5% or <1%) generated similar results and confirmed that UCART22 with increase HIF-1a expression can survive, express CD22 CAR and be active under hypoxia.

Similar results (survival, CTL activity) were obtained in mice treated with CAMPATH® (50 micrograms/mL) confirming the resistance of UCART22 to drugs. The possibility for the UCART22 cells of the invention to reach cancer cells nested in tissues or to reach cancer cells making clusters in vivo is suggested, as the amount of cancer cells "recovering" or "escaping" the treatment with UCART22 was much less (about 15% decrease) than in mice treated with UCART22 non-resistant to $O_2$. It seems therefore that a local hypoxia created by liquid tumors may prevent immune cells to fight them.

Figure 3:
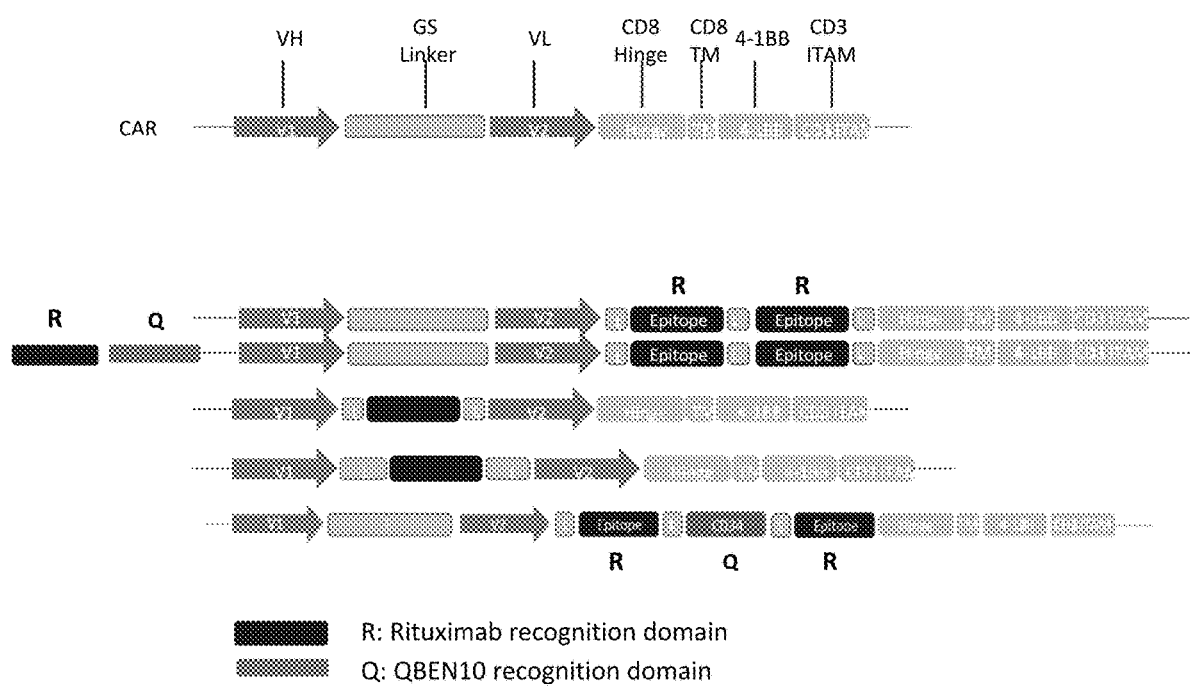
FIG. 3: Examples of CD22 CAR constructs of the invention comprising a safety switch. At least a rituximab (R) mAb-specific epitopes (black box), preferably 3 rituximab mAb-specific epitopes and more preferably 3 rituximab mAb-specific epitopes and a QBEND-10 (Q) mAb-specific epitopes (grey box) are inserted into the CD22 CAR. R may be inserted into the scFv, between a VH and a VL domain (or a VL and a VH domain) and/or into the hinge.

Experiments carried out to determine whether UCART22 cells could be eliminated if and when desired (FIGS. 3 and 4). In mice, Rituximab induced a significant decrease in UCART as suggested by an increased fluorescence intensity of tumor cells in mice treated with rituximab and UCART as compared to cells alone.

The clinical first data obtained show that UCAR T cells significantly reduce relapse and refractory ALL in vivo and in vitro, with no or very mild (grade 1) GVHD and mild to no uncontrolled cytokine storm.

Such treatment is to be less "toxic" than autologous CD22 CAR T and can be controlled in patients using rituximab and/or QBEND-10.

Cells persists in human long enough to be active (over a month) and can be depleted using QBEND-10.

Examples of CD22 CAR Polypeptide Sequences Prepared

Framed sequences correspond to preferred VH and VL sequences. VH and VL may be swapped (modification in hot spot) to improve CAR efficiency as described above.

```
v1-m972 (FcγRIIIα-CD8αTM-41BB.1C-CD3ζ.IC) (Control not part of the invention).
                                                              (SEQ ID NO: 66)
MALPVTALLPLALLLHAARPEVQLVQSGGGVVRPGGSLRLPCAASGFTFDDYGMSWVRQAPGKGLEWVSGINWNGGS

TGYADSVKGRFTISRDNAKNSLYLQMNSLRAEDTALYHCARGGDDAFDIWGQGTMVTVSSGGGGSGGGGSGGGGSRI

VMTQSPGTLSVSPGETATLSCRASQSFSNMLAWYQQKSGQPPRLLIYGVSTRAAGVPARFSGSGSGTEFTLTISNLQ

SEDFAVYYCQQYGDWPRYTFGQGTKVERKGLAVSTISSFFPPGYQIYIWAPLAGTCGVLLLSLVITLYCKRGRKKLL

YIFKQPFMRPVQTTQEEDGCSCRFPEEEEGGCELRVKFSRSADAPAYQQGQNQLYNELNLGRREEYDVLDKRRGRDP

EMGGKPRRKNPQEGLYNELQKDKMAEAYSEIGMKGERRRGKGHDGLYQGLSTATKDTYDALHMQALPPR.

V3-m972 (CD8α-CD8αTM-41BB.IC-CD3ζ.IC) (control not part of the invention).
                                                              (SEQ ID NO: 67)
MALPVTALLPLALLLHAARPEVQLVQSGGGVVRPGGSLRLPCAASGFTFDDYGMSWVRQAPGKGLEWVSGINWNGGS

TGYADSVKGRFTISRDNAKNSLYLQMNSLRAEDTALYHCARGGDDAFDIWGQGTMVTVSSGGGGSGGGGSGGGGSRI

VMTQSPGTLSVSPGETATLSCRASQSFSNMLAWYQQKSGQPPRLLIYGVSTRAAGVPARFSGSGSGTEFTLTISNLQ

SEDFAVYYCQQYGDWPRYTFGQGTKVERKTTTPAPRPPTPAPTIASQPLSLRPEACRPAAGGAVHTRGLDFACDIYI

WAPLAGTCGVLLLSLVITLYCKRGRKKLLYIFKQPFMRPVQTTQEEDGCSCRFPEEEEGGCELRVKFSRSADAPAYQ

QGQNQLYNELNLGRREEYDVLDKRRGRDPEMGGKPRRKNPQEGLYNELQKDKMAEAYSEIGMKGERRRGKGHDGLYQ

GLSTATKDTYDALHMQALPPR.

v1-m971 (FcγRIIIα-CD8αTM-41BB.1C-CD3ζ.IC).
                                                              (SEQ ID NO: 68)
MALPVTALLLPLALLLHAARPQVQLQQSGPGLVKPSQTLSLTCAISGDSVSSNSAAWNWIRQSPSRGLEWLGRTYYR

SKWYNDYAVSVKSRITINPDTSKNQFSLQLNSVTPEDTAVYYCAREVTGDLEDAFDIWGQGTMVTVSSGGGGSGGGG

SGGGGSDIQMTQSPSSLSASVGDRVTITCRASQTIWSYLNWYQQRPGKAPNLLIYAASSLQSGVPSRFSGRGSGTDF
```

```
                                                   -continued
TLTISSLQAEDFATYYCQQSYSIPQTFGQGTKLEIKGLAVSTISSFFPPGYQIYIWAPLAGTCGVLLLSLVITLYCK

RGRKKLLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQALPPR.

v3-m971 (CD8α-CD8αTM-41BB.IC-CD3ζ.IC).
                                                                 (SEQ ID NO: 69)
MALPVTALLLPLALLLHAARPQVQLQQSGPGLVKPSQTLSLTCAISGDSVSSNSAAWNWIRQSPSRGLEWLGRTYYR

SKWYNDYAVSVKSRITINPDTSKNQFSLQLNSVTPEDTAVYYCAREVTGDLEDAFDIWGQGTMVTVSSGGGGSGGGG

SGGGGSDIQMTQSPSSLSASVGDRVTITCRASQTIWSYLNWYQQRPGKAPNLLIYAASSLQSGVPSRFSGRGSGTDF

TLTISSLQAEDFATYYCQQSYSIPQTFGQGTKLEIKTTTPAPRPPTPAPTIASQPLSLRPEACRPAAGGAVHTRGLD

FACDIYIWAPLAGTCGVLLLSLVITLYCKRGRKKLLYIFKQPFMRPVQTTQEEDGCSCRFPEEEEGGCELRVKFSRS

ADAPAYQQGQNQLYNELNLGRREEYDVLDKRRGRDPEMGGKPRRKNPQEGLYNELQKDKMAEAYSEIGMKGERRRGK

GHDGLYQGLSTATKDTYDALHMQALPP.
```

Results

The CAR construct selected for preparing in UCART22 comprises the m971 anti-human CD22 scFv (described in Haso et al., 2013), a CD8α hinge (optional) and transmembrane domain, and a cytoplasmic tail composed of 4-1BB co-stimulatory domain and CD3ζ signaling domain (FIG. 3).

Another CAR construct comprises successively, a sequence the m971 anti-human CD22 scFv, two binding domains for rituximab (CD20), a CD8α hinge and transmembrane domain, and a cytoplasmic tail composed of 4-1BB co-stimulatory domain and CD3(signaling domain (FIG. 3).

An alternative CAR construct comprised successively a binding domain for rituximab (CD20), a binding domain for Q-BEN10 (CD34), the m971 anti-human CD22 scFv, two binding domains for rituximab (CD20), a CD8α hinge and transmembrane domain, and a cytoplasmic tail composed of 4-1BB co-stimulatory domain and CD3(signaling domain (FIG. 3).

In UCART22, a recombinant third generation self-inactivating (SIN) lentiviral vector (rLV) is used to generate T-cells expressing the anti-CD22 CAR and the RQR8 depletion mechanism under the control of the human EF1α promoter (FIG. 4). Recombinant lentiviral vectors derived from HIV are genetically stable and have not yet shown evidence of pathological consequences ascribed to the vector (Chang and Sadelain, 2007; Wang et al., 2009). In addition, the conditions for transduction of T-cells with rLV are known and are compatible with the preservation of the functional properties of T-cells.

Figure 9:
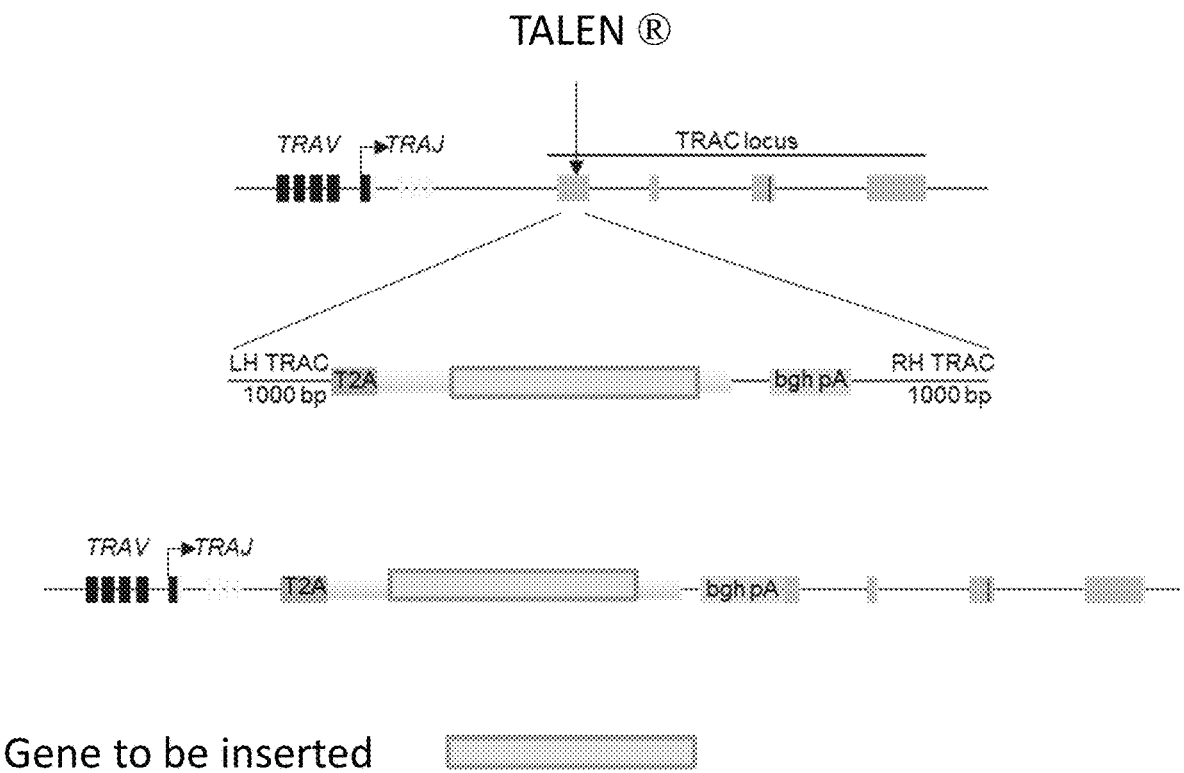
FIG. 9: General Strategy to insert a gene into the TRAC gene using TALEN®.

In UCART22, AAV6 vector may be used after genetic editing of a gene such as the TRAC gene (gene encoding the alpha subunit or the TCR) or any gene disclosed in PCT/EP2017/076798 (FIG. 9).

Variants of anti-CD22 CAR construct of the invention comprising an additional CD19 scFv (before or after the CD22 scfv) were also prepared as well as a multichain CD22 CAR, a multichain CD22, CD19 CAR (FIG. 2) were also constructed and inserted into lentiviral vector.Adeno-associated virus 6 (AAV6) vector allowing the CD22 CAR constructs or CD19 CAR constructs described below to be inserted into the TRAC gene or into the CD25 gene, or into the β$_2$ Microglobulin gene were made (the CAR sequence was flanked in 5' and in 3' of sequences allowing homologous recombination into the TRAC gene, into the CD25 gene or into the β$_2$ Microglobulin gene after specific cut of said gene using a specific TAL-protein-Fok-1 (TALEN®).

A UCART22 was made comprising in addition a TGFbeta receptor KO gene, an IL-10 receptor KO gene, an AHR KO gene, a PD1 KO gene, a LAG-3 KO gene, a TIM-3 KO gene, or combination thereof.

An example of each UCART22 comprising in addition either a TGFbeta receptor KO gene, or an IL-10 receptor KO gene, or an aryl hydrocarbon receptor (AHR) KO gene, or a PD1 KO gene, or a LAG-3 KO gene, or a TIM-3 KO gene, was made.

To test the effect of depleting CD19+ CD22+ cancer cells, the anti-CD19 construct previously described in "Molecular remission of infant B-ALL after infusion of universal TALEN® gene-edited CAR T cells. Waseem Qasim, et al., 2017. *Science Translational Medicine*, 25 Jan. 2017), and further comprising a suicide gene distinct from those carried by CD22 CAR (as described in WO2016120216A1), was also prepared. In the present study, the cytolytic activity of:

1) a combination of UCART19+UCART22 (two single chain CARs), as compared to individual cells alone (all at 5×10$^6$ cells), 2) TCR-negative cells expressing a bispecific anti-CD22-ant-CD19 CAR, (a bispecific single chain CAR), as compared to individual cells alone (all at 5×10$^6$ cells), 3), or a multichain CAR comprising both CD22 and CD19 scfvs- or CD19 CD22scfvs, Was measured as compared to individual cells alone (all at 5×10$^6$ cells).

Expression of RQR8, R2CD22CAR or QR3CD22CAR to Confer Sensibility to Rituximab /Rituximab and QBEND-10

The lentiviral vector cassette that drives the expression of CD22CAR has been designed to co-express RQR8 (through a 2A peptide linker). RQR8 is a depletion ligand that can be potentially activated in case of unmanageable adverse events related to the administration of UCART22. RQR8 is a 136 amino acid artificial cell surface protein combining antibody-binding epitopes from human CD34, recognized by the QBEND-10 antibody, and human CD20 (Philip et al., *Blood*, 2014). The CD20 epitopes present within the construct are recognized by rituximab, thus enabling deletion of RQR8-expressing cells through complement-mediated cell killing (CDC) and antibody-dependent cell-mediated cytotoxicity (ADCC) in the presence of Rituximab/and or QBEND-10. The sequence of RQR8 as disclosed in Philip et al., *Blood,* 2014 (see, e.g., Supplementary Materials) is:

(SEQ ID NO: 60)
MGTSLLCWMALCLLGADHADACPYSNPSLCSGGGGSELPTQGTFSNVSTN

VSPAKPTTTACPYSNPSLCSGGGGSPAPRPPTPAPTIASQPLSLRPEACR

PAAGGAVHTRGLDFACDIYIWAPLAGTCGVLLLSLVITLYCNHRNRRRVC

KCPRPVV.

In other experiments, constructs corresponding to an anti-CD22 CAR comprising 2 epitopes recognized by rituximab (R) (R2 CD22 CAR: two epitopes recognized by rituximab, inserted just after the scFv and just before the hinge, or instead of the hinge to shorten the extracellular domain as compared to the whole construction with hinge) or a "QR3" QR3 CD22 CAR (Q: epitope recognized by QBEND-10, Q-R—in N terminal before the VH-linker-VL RR hinge TM-41BB-CD3 zeta), were prepared and tested against cells expressing various level of CD22.

TRAC Gene Knock-Out to Limit Alloreactivity of UCART22

A potential limitation of allogeneic adoptive immunotherapy approaches is that recognition of MHC disparities between donor and recipient through the donor cell's TCRαβ complex may lead to donor T-cell activation/proliferation and the development of Graft-versus-Host Disease (GvHD). TCRαβ is composed of a and R subunits, with the TCRα encoded by a single gene and TCRβ by two homologous genes.

UCART22 cells are genetically modified to specifically disrupt the T-cell receptor alpha constant (TRAC) gene. The inactivation of the TRAC gene prevents the cell surface expression of the TCRαβ complex, eliminating TCR-mediated recognition of histocompatibility antigens that can lead to GvHD. At the end of UCART22 manufacturing process, the remaining TCRαβ+ cells are depleted ensuring a residual level of ≤3.0% of TCRαβ+ cells in the final product, as per release criteria.

CD52 gene knock-out to confer resistance to alemtuzumab

UCART22 has been engineered to be a mix of CD52⁻ and CD52⁺ cells allowing the potential use of alemtuzumab in the lymphodepletion regimen before UCART22 administration. Alemtuzumab is a monoclonal antibody that binds to human CD52. The CD52⁻fraction of UCART22 is thus resistant to alemtuzumab.

TALEN® technology is used to disrupt both the TRAC and CD52 genes. In the UCART22 production process, the TRAC and CD52 TALEN® are introduced into the cells as messenger Ribonucleic Acid (mRNA) using an electroporation system. This transient expression permits TALEN® to perform efficient targeted gene knock-out before being degraded by the cells. This approach prevents potential risks associated with long-term expression of nucleases in cells injected into patients.

B2M Gene Knock-Out to Limit Alloreactivity of UCART22

The TALEN® technology is used to disrupt both the TRAC and B2M genes. In the UCART22 production process, the TRAC and B2M TALEN® are introduced into the cells as messenger Ribonucleic Acid (mRNA) using an electroporation system. This transient expression permits TALEN® to perform efficient targeted gene knock-out before being degraded by the cells.

EXAMPLES

Sources of T-Cells Used in Non-Clinical Studies (Pharmacology and Toxicology)

A description of the cell products utilized in the non-clinical studies is summarized in Table 17 below.

TABLE 17

Engineered T-cells used in in vitro and in vivo preclinical studies.

| Cells | Description | Process | Comments |
| --- | --- | --- | --- |
| NTD T-cells | Non transduced T-cells | Non transduced Non electroporated | Unmodified T-cells |
| NTD DKO T-cells | Non transduced double KO T-cells | Non transduced TRAC and CD52 TALEN ® mRNA electroporation Purification of TCRαβ-cells | Non transduced TCRαβ-_CD52-T-cells |
| NTD DKO T-cells | Non transduced double KO T-cells | Non transduced TRAC and B2M TALEN ® mRNA electroporation Purification of TCRαβ-cells | Non transduced TCRαβ-_MHCI-T-cells |
| UCART22 cells | Transduced double KO T-cells | LV-RQR8-2A-CD22CAR transduction TRAC and CD52 TALEN ® mRNA electroporation Purification of TCRαβ-cells | TCRαβ-_CD52-transduced with the rLV encoding the CD22CAR and RQR8 and purified for TCRαβ-deficient cells |
| UCART22 cells | Transduced double KO T-cells | CD22CAR transduction TRAC and b2M TALEN ® mRNA electroporation Purification of TCRαβ-cells | TCRαβ-_MHCI-transduced with the AAV6 encoding the CD22CAR (R2) or AAV6 encoding CD22 CD19CAR and purified for TCRαβ-deficient cells |
| UCART22/19 cells | Transduced double KO T-cells | CD22CD19CAR transduction TRAC and b2M TALEN ® mRNA electroporation Purification of TCRαβ-cells | TCRαβ-_MHCI-transduced with the AAV6 encoding the CD22CD19CAR and RQR8 and purified for TCRαβ-deficient cells |

DKO: double KO, KO: knock-out, rLV: recombinant lentiviral vector, MHCI major histocompatibility class I, and B2m beta2 microblobulin.

Summary

UCART22 activation is driven by contact between the anti-CD22 Chimeric Antigen Receptor (CD22CAR) and the CD22 antigen leading to the destruction of CD22+ B-ALL cells through T-cell mediated cytotoxicity and potentially pro-inflammatory cytokine production.

Proof of concept studies performed during the development of other UCART products (UCART19 and UCART123) demonstrated that UCART cells (TCRαβ-deficient CAR T-cells) are as active as non gene-edited CAR T-cells (TCRαβ-positive CAR T-cells) in vitro and in vivo in tumor xenograft models in NSG mice (Poirot et al., 2015). This was verified for TCRαβ-deficient CD22 CAR T-cells and for TCRαβ-deficient, MHC I deficient CD22 CAR T-cells as compared to TCRαβ-positive CD22 CAR T-cells. In vitro pharmacology studies performed during UCART22 non-clinical development are summarized in Table 18 below. Studies have demonstrated:

The anti-tumor activity of UCART22 through CD22 antigen-dependent cytotoxicity and cytokine secretion assays. Activity assays were performed against B-ALL cell lines and primary B-ALL samples.

The efficient TALEN® mediated inactivation of the TRAC and CD52 genes.

The efficient TALEN® mediated inactivation of the TRAC and β2 Microglobulin genes.

That CD52– T-cells are resistant to alemtuzumab.

The efficient elimination of RQR8+ cells or R2 CD22CAR+ cells using rituximab.

In vivo pharmacology studies (summarized in Table 18) have demonstrated:

the anti-tumor activity of UCART22 in vivo against tumor xenografts in immunodeficient mice using a B-ALL cell line. The in vivo activity of UCART22 manufactured under GMP conditions confirmed against a B-ALL cell line.

the improved anti-tumor activity of UCART22/19 in vivo against tumor xenografts in immunodeficient mice using a B-ALL cell line. The in vivo activity of UCART22/19 and 19/22 manufactured under GMP conditions against a B-ALL cell line.

The ability of rituximab to eliminate RQR8+ cells in an immunocompetent mouse model.

TABLE 18

List of in vitro pharmacology studies.

| Study | Method | Cells | GLP | Results |
|---|---|---|---|---|
| Primary Pharmacology | | | | |
| Cytotoxicity assay | Flow cytometry | UCART22 | No | Cytotoxicity assays using CD22+ cells (B-ALL cell lines or B-ALL primary samples) showed CD22 specific cell killing by UCART22 cells. |
| | | GMP UCART22 | Yes | Cytotoxicity assay against a CD22+ tumor cell line will be performed on all GMP batches. |
| Cytokine secretion assay | ELISA/flow cytometry | UCART22 | No | UCART22 cells specifically secrete IFNγ in presence of CD22+ tumor cells (B-ALL cell lines or B-ALL primary samples). |
| | | GMP UCART22 | Yes | Cytokine secretion assay against a CD22+ tumor cell line will be performed on all GMP batches. |
| SECONDARY PHARMACOLOGY | | | | |
| Molecular inactivation of the TRAC and CD52 genes | High throughput sequencing of the TRAC and CD52 loci | T-cells transfected with mRNA encoding TRAC and CD52 TALEN® (GMP grade mRNA) | No | High throughput sequencing of the TRAC and CD52 loci in TALEN® treated T-cells showed high levels of site specific modifications at the TRAC and CD52 loci. |
| Functional inactivation of the TCRαβ | Flow cytometry analysis | UCART22 | No | No upregulation of CD25 and CD69 activation markers in UCART22 following PHA-mediated TCR stimulation. |
| Resistance to CD8+– cells | Cytolytic assays | B2M + TRAC TALEN® treated T-cells | No | T-cells that contain beta2M gene and TRAC inactivation are not eliminated in the presence of CD8+ T cells. |
| Resistance to alemtuzumab of CD52– cells | CDC assays | CD52 TALEN® treated T-cells | No | T-cells that contain a CD52 gene inactivation are not eliminated in the presence of both alemtuzumab and complement in CDC assays. |
| Sensitivity of UCART22 to rituximab | CDC assay | UCART22 (development batches) | No | UCART22 cells are eliminated in the presence of both rituximab and complement in CDC assay. |

CDC = complement-dependent cytotoxicity, PHA = Phytohaemagglutinin.

TABLE 19

List of in vivo studies.

| Study | Cells | Animal model | Tumor model | GLP study | Results |
|---|---|---|---|---|---|
| PRIMARY PHARMACOLOGY | | | | | |
| Anti-tumor activity of UCART22 | UCART22 | Tumor xenograft model in NSG mice | B-ALL cell line (Daudi) | No | In vivo studies performed to demonstrate the anti-tumor activity of UCART22 against a B-ALL cell line. Read-out: tumor burden (by in vivo bioluminescent imaging) survival of the mice |
| | GMP UCART22 | | | GLP-like | A confirmatory study is being performed with GMP UCART22 to demonstrate activity in vivo. |
| SECONDARY PHARMACOLOGY | | | | | |
| Sensitivity of RQR8+ cells to rituximab | mouse splenocytes transduced with a retrovirus encoding the RQR8-2A-CD19 CAR construct | C57BL/6 × Balb/c (F1) mice | | No | POC study demonstrating efficient rituximab-induced depletion of RQR8+ cells in blood, spleen, bone marrow and lymph nodes. Study published in Philip et al., 2014. |

To demonstrate the activity of UCART22 cells, CAR driven cytotoxicity and cytokine secretion assays were performed against tumor cell lines and primary B-ALL cells.

UCART22 Activity Evaluated by Cytotoxicity Assays

Cytotoxic Activity Against B-ALL Cell Lines

The potential cytotoxicity of UCART22 was evaluated against several tumor cell lines derived from child or adult B-ALL patients (Table 20). The results show that MHH-CALL-4, MUTZ-5, SEMVIK2, PALL-2, LAX2, BALL-1, NALM-6 and RS4;11 are all CD22+ cell lines expressing different levels of CD22. Two Acute Myeloid Leukemia (AML) cell lines (OCI-AML2 and MOLM13), that do not express CD22, were used as negative controls.

(CAR-) TRAC and CD52 double KG T-cells are used as a control to calculate the percentage of specific cell lysis of target CD22+ B-ALL cells by UCART22. The results show the cytotoxic activity of UCART22 cells against a panel of CD22+ B-ALL tumor cell lines. UCART22 shows specific cell lysis activity against all cell lines expressing CD22, even at the lowest levels.

Cytotoxic Activity Against Primary B-ALL Samples

The cytotoxic activity of UCART22 was confirmed against several primary B-ALL samples. The characteristics of the primary samples are presented in Table 21. Only

TABLE 20

Characteristics of the cell lines.

| Cell line | Provider | Reference | Type of disease | CD22 expression |
|---|---|---|---|---|
| BALL-1 | DSMZ | ACC 742 | B-ALL (complex karyotype) | + |
| LAX2 | M. Muschen | | B-ALL (Ph-positive) | + |
| MHH-CALL-4 | DSMZ | ACC 337 | B-ALL (Ph-like) | + |
| MUTZ-5 | DSMZ | ACC 490 | B-ALL (Ph-like) | + |
| NALM-6 | ATCC | CRL-3273 | B-ALL (t(5;12)) | + |
| PALL-2 | JCRB | JCRB1345 | B-ALL (Ph-positive) | + |
| RS4;11 | ATCC | CRL-1873 | B-ALL (t(4;11)) and hyperdiploid | + |
| SEMK2 | DSMZ | ACC 546 | B-ALL (t(4;11)) | + |
| MOLM13 | DSMZ | ACC 554 | AML | − |
| OCI-AML2 | DSMZ | ACC 99 | AML | − |

The specific cytotoxicity of UCART22 against CD22+ cells is evaluated by measuring the viability of CD22+ target cells after co-culture with UCART22 cells. Non-transduced patient samples with greater than 50% blasts were used for the co-incubation studies, which accounted for 14 of the 19 samples.

TABLE 21

ALL primary samples evaluated in preclinical studies.

| ID | Name | Age/Sex | Cytogenetic abnormalities | Mutations | Clinical Status | % Blasts | % CD22+ Blasts |
|---|---|---|---|---|---|---|---|
| Pt1 | PB6265310 | 24/M | CRLF2+ AND PH+ | JAK2R683G, EZH2 | Diagnosis | 84 | ND |
| Pt2 | PB6296870 | 69/F | Ph-like ALL (CRLF2+) | TP53 | Diagnosis | 17 | 92.3 |
| Pt3 | PB3882028 | 29/M | Ph-like ALL (CRLF2+) | No mutations | Relapse | 32 | 58.7 |
| Pt4 | PB6232236 | 21/M | Ph-like (IGH-CRLF2) | JAK2R6835 | Relapse | 65 | 94.7 |
| Pt5 | PB6304576 | 68/M | NOT CRLF2+, NOT Ph+ | TP53, IDH2 | Diagnosis | 69 | 25.7 |
| Pt6 | PB6352880 | 81/M | PH+ ALL | No mutations | Diagnosis | 48 | 86.5 |
| Pt7 | PB6351838 | 56/F | PH+ ALL | No mutations | Diagnosis | 68 | 90.2 |
| Pt9 | PB6268010 | 21/M | NOT CRLF2+, NOT Ph+, trisomy 4 | No mutations | Diagnosis | 60 | 92.0 |
| Pt10 | BM6301348 | 69/F | Ph-like ALL (CRLF2+) | NRAS, EZH2 | Relapse | 93 | 84.3 |
| Pt11a | PB6301394-1 | 55/F | Ph-like ALL (CRLF2+) | No mutations | Diagnosis | 75 | 89.7 |
| Pt11b | BM6301394-2 | 55/F | Ph-like ALL (CRLF2+) | No mutations | Diagnosis | 91 | 98.1 |
| Pt12 | PB6300308 | 22/M | Ph+ ALL | No mutations | Diagnosis | 79 | 47.2 |
| Pt13 | PB6124238 | 33/M | t(4; 11) | TP53 | Relapse | 59 | 80.2 |
| Pt14 | PB6309102 | 54/F | PH+ ALL | No mutations | Diagnosis | 23 | 83.8 |
| Pt15 | PB6269878 | 68/M | hypodiploid complex cyto | No mutations | Diagnosis | 67 | 67 |
| Pt16 | PB6229772 | 70/M | Complex | TP53 | Relapse | 51 | 51 |
| Pt17 | BM3748646 | 39/M | Ph-like | NOT DONE | Diagnosis | 90 | 90 |
| Pt18 | BM2820966 | 65/F | Ph-like (IGH-CRLF2) | IKZF1 deletion | Diagnosis | 92 | 92 |
| Pt19 | BM4198594 | 21/M | Ph-like (IGH-CRLF2 + BCR-ABL1) | CRLF2_F232C, ITPKB_P167R, ITPKB_S92SG PTPN11 | Relapse | 82.5 | 82.5 |

ND: non determined

The CD22 and CD19 expression level was also evaluated in all primary B-ALL samples except Pt1. 11 had CD22 surface expression above CD22− controls and 4 B-ALL patient samples showed CD22 surface expression in the range found in B-ALL cell lines (>1000 CD22 molecules/cell). Highly expressing CD22 (>60%) also expressed CD19 except for two relapse samples).

Using the same approach as for the cell lines, it the CTL activity against that 8 B-ALL patient samples (greater than 10% specific cell lysis) was confirmed.

Cytokine Secretion Assay Against B-ALL Cell Lines and Primary B-ALL Samples

The release of interferon-gamma (IFNγ) and other cytokines by UCART22 cells co-incubated with several cells line or B-ALL patient samples was assessed using the BieLegend BIOLEGEND® Legend PLEX 13-cytokine assay. IFNγ was found to have the highest concentration of all detected cytokines (IL-2, IL-4, IL-5, IL-6, IL-9, IL-10, IL-13, IL-17A, IL-17F, IL-21, IL-22 and tumor necrosis factor alpha (TNF-α)) secreted into the media after a 25 hour co-incubation between B-ALL cells and either UCART22 or control T-cells (NTD DKO).

High level of IFNγ secretion was observed when UCART22 is co-incubated with both B-ALL cell lines and primary B-ALL samples.

In Vitro Secondary Studies

TALEN®-induced inactivation of the TRAC, B2M and CD52 genes

The ability to use UCART22 in an allogeneic setting depends on the capacity to prevent the cell surface expression of the TCRαβ, MHC CI, eliminating TCR-mediated recognition of histocompatibility antigens that can lead to GvHD and attack by host CD8+ cells. To effectively eliminate TCRαβ and MHC CI from the cell surface, TALEN®-mediated gene-editing has been used to inactivate the TRAC and the 32 Microglobulin gene (B2M), gene. In addition, another TALEN® was used during the manufacturing process of UCART22 to inactivate the CD52 gene allowing the use of alemtuzumab in the lympho-depleting conditioning regimen. In particular settings, the TALEN® was used during the manufacturing process of UCART22 to inactivate the 32 Microglobulin gene (B2M), to alter major histocompatibility class I (MHC Class I) molecules expression and to prevent rejection by hosts T cells.

Molecular Analysis of TRAC, CD52, B2M Genes Disruption

To demonstrate targeted modifications of the TRAC and CD52 genes at a molecular level, genomic deoxyribonucleic acid (DNA) was isolated from T-cells electroporated with GMP grade TRAC and CD52 TALEN® mRNA or TRAC and B2M TALEN® mRNA and purified for TCRαβ-cells MHCCI-. The regions around the TRAC, B2M and CD52 TALEN® cleavage sites were amplified by polymerase chain reaction (PCR) and analyzed by Next Generation Sequencing (NGS, Illumina). In control samples, the same analysis was performed with cells removed before electroporation of TALEN® mRNA (at Day 6). This analysis indicates that while control cells at Day 6 did not display any modifications at the TRAC and CD52 loci, a high frequency of modifications were detected in the TALEN®-treated T-cells (Table 22).

Table 22: Percentage of Non-Homologous End Joining (NHEJ) upon TALEN® cleavage at the TRAC and CD52 and B2M loci.

Percentages are determined by NGS in TALEN®-treated T-cells from 3 different batches. Control cells were sampled before TALEN® mRNA electroporation for all batches.

TABLE 22

|  | TRAC | | CD52 | | B2M | |
| --- | --- | --- | --- | --- | --- | --- |
|  | mean | SD | mean | SD | Mean | SD |
| Control | 0.09 | 0.08 | 0.09 | 0.07 | 0.09 | 0.06 |
| TALEN ® | 84.63 | 5.65 | 83.26 | 4.91 | 89.0 | 3.88 |

Further analysis of the sequences indicates that TALEN® induced modifications are located in a small region surrounding the target site with 93-97% of these modifications being deletions. These deletions are generally small, with on average 97% smaller than 150 bp and 81% smaller than 50 bp.

Functional Assay Demonstrating TRAC Gene Disruption in UCART22

To demonstrate the functional inactivation of TCRαβ, UCART22 cells were assayed for their ability to express activation markers such as CD25 and CD69 following Phytohaemagglutinin (PHA)-mediated TCR stimulation. UCART22, performed with all the GMP raw materials, T-cells were recovered either before (TRAC) or after (UCART22) depletion of TCRαβ+ cells. Cells were reactivated with 0.5 μg/mL PHA during 24 h. Expression of activation markers (CD25 and CD69) was measured by flow cytometry. While control TRAC cells (65.2% TCRαβ−) upregulate CD25 and CD69, no upregulation was observed on UCART22 cells (98.9% TCRαβ−) confirming the absence of the TCRαβ receptor in UCART22.

Resistance to Alemtuzumab of CD52-UCART22 Cells

The ability to use alemtuzumab, an anti-CD52 monoclonal antibody, in the lymphodepletion regimen depends on the effective elimination of the CD52 glycoprotein from the cell surface of UCART22 cells to prevent their elimination by alemtuzumab. UCART22 are thus engineered, using CD52 TALEN®, to be a mix of CD52+ and CD52− cells. Flow cytometry analysis performed with development batches of UCART22 at the end of manufacturing process indicate that on average 72% of the T-cells (CD45+/CD4+ or CD8+ cells) are CD52− (range 62.3-76.5%, N=6).

To demonstrate that CD52− cells are resistant to alemtuzumab, a complement-dependent cytotoxicity (CDC) assay was performed. Human T-cells containing a TALEN®-mediated CD52 gene inactivation were treated with 50 μg/mL of a rat anti-CD52 antibody from which the therapeutic antibody alemtuzumab is derived or rat immunoglobulin G (IgG) as control with or without rabbit complement for 2 hours at 37° C., then analysed by flow cytometry for viability and CD52 expression.

The results show that cells that do not contain a CD52 gene inactivation are specifically eliminated through complement-dependent cytotoxicity in the presence of alemtuzumab.

Resistance to Host CD8+ T Cells

MHC Class I deficient UCART22 cells were resistant to CD8+ T-cell-mediated destruction. Although interferon-γ (IFN-γ) treatment significantly induced $β_2$ Microglobulin expression, promoting CD8+ T cell-mediated killing of control UCART22.

Demonstration of Effective Depletion of UCART22 Following Treatment with Rituximab UCART22 are allogeneic T-cells and thus should be eliminated upon recovery of the patient's immune system. In addition, UCART22 are engineered to co-express the CD22CAR and RQR8, a short membrane protein that provides two epitopes that bind rituximab (RTX), a therapeutic monoclonal antibody specific for human CD20. RQR8 provides therefore the possibility of depleting UCART22 through the administration of rituximab.

The ability to eliminate UCART22 cells through complement-dependent cytotoxicity (CDC) following treatment with RTX was examined. Frozen UCART22 (from 5 different development batches) were thawed and co-cultured with Raji CD22+ cells at a 1:0.25 ratio for 3 days. After this reactivation period, the CDC assay was performed (cells were incubated with RTX (100 μg/ml) for 2 hours in the presence or absence of baby rabbit complement (BRC)). The results demonstrate that ~85% of CAR+ cells are efficiently eliminated in vitro in the presence of both RTX and complement.

Another mechanism of action for RTX, by which depletion of RQR8+ cells can be achieved, is Antibody-Dependent Cell-mediated Cytotoxicity (ADCC) (Seidel et al., 2013). In this case, effector cells of the immune system (mainly Natural Killer -NK- cells) can actively lyse target cells whose membrane-surface antigens have been bound by a specific antibody.

Complementary experiments have been published by Martin Pule at UCL (Philip et al., 2014) demonstrating effective in vitro mediated elimination of RQR8+ T-cells by CDC and ADCC (primary human T-cells transduced with a bicistronic retroviral vector (SFG.RQR8.IRES.eGFP) encoding RQR8 and GFP and selected with Miltenyi QBEND-10 beads). Time course and RTX dose titration demonstrate that CDC is highly effective at RTX concentrations of 25 μg/mL and above, with killing occurring within 30 minutes. Similarly, ADCC mediated sensitivity has been demonstrated for RQR8+ T-cells.

In Vivo Studies

Rationale for Selection of Animal Species/Model

Because of the human specificity of UCART22, studies in standard immunocompetent animal models are not applicable due to the rapid targeting and elimination of human UCART22 cells by xenogeneic immune reactions.

Thus, two approaches may be envisaged for in vivo modelling of UCART22 activity: syngeneic animal models and human tumor xenograft models in immunodeficient animals.

A syngeneic animal model approach would involve the re-creation/re-development of a species specific-version of UCART22 for a model organism, followed by assessment of the functional properties of this species-specific UCART22 surrogate product when engrafted in a syngeneic host. This approach is not considered relevant due to the fact that the properties of individual CARs vary considerably, and because species-specific differences in immune function, physiology, and genetics significantly compromise extrapolation of activity of UCART22 in humans.

The immunodeficient murine xenograft model was chosen as it allows the engraftment of both UCART22 and human tumor CD22+ cells (B-ALL cell lines or primary samples). This animal model has been extensively used for the assessment of in vivo activity of CAR T-cell therapies. While these models have the same limitations as the above immunocompetent models with respect to on-target/off-tumor cytotoxicity and off-target cytotoxicity, and completely eliminate any role of MHC mismatch, they have proven to be extremely useful for assessing in vivo anti-tumor efficacy of CAR T-cells. They have emerged as the de-facto standard for assessment of in vivo activity of CAR T-cell products (see for example in Carpenito et al., 2009; Gade et al., 2005; Gill et al., 2014; Hudecek et al., 2010; Kenderian et al., 2015; Mardiros et al., 2013; Zhou et al., 2013 among many published articles). They have proven capable of discriminating the relative anti-tumor activity of different CARs, highlighting their capacity to capture and semi-quantitatively read out useful human in vivo T-cell functions (see for example Milone et al., 2009). Thus, human CD22+ tumor cells have been engrafted into immunodeficient mice (NSG mice) followed by administration of UCART22, with serial assessment of the tumor burden and survival time as an index of anti-tumor activity.

Selected Tumor Models

With respect to the tumor xenografts, UCART22 activity in vivo has been evaluated against Daudi cells, a CD22+ B-ALL cell line (CCL-213, ATCC®). The cell line has been modified to express the firefly luciferase (and GFP) by transduction with a lentiviral vector (amsbio LVP438-PBS) in order to follow the tumor burden by in vivo imaging (Daudi-Luc-GFP cells).

Selected Mouse Strains

The mouse strains used in the in vivo non-clinical studies were:
1/ Highly immunodeficient NSG mice (NOD.Cg-Prkdcscid Il2rgtm1Wjl/SzJ; The Jackson Laboratory strain #5557) lacking mature T cells, B cells and functional NK cells to demonstrate the anti-tumor activity.
2/ An immunocompetent mouse model (C57BL/6× BALB/c (F1) mice) to demonstrate the efficacy of the RQR8 depletion or R2 CD22CAR mechanism.

Methods of Analysis

The activity of UCART22 in vivo was evaluated using:
bioluminescence measurement of treated mice in respect to the control group (for the xenograft model with cell lines expressing the luciferase),
clinical signs,
overall survival of the mice.

Route of Administration

The route of administration of UCART22 in animals is the intravenous injection (single non-split dose). In human, UCART19 and UCART22 were also injected intravenously (non-split dose), once twice or three or four times, alone or one after the other one according to the following succession 19. 22 19 22 19 or 22 19 22 19 or 19/22 19/22.

Demonstration of Anti-Tumor Activity In Vivo of UCART22

UCART22 activity was demonstrated in immunodeficient mice engrafted with Daudi-Luc-GFP human tumor cells with several development batches of UCART22. An example of a study is shown FIG. 8. In addition, a confirmatory study is ongoing to evaluate the in vivo activity of a GMP batch of UCART22.

Briefly, NSG mice were intravenously injected with 0.5× 106 Daudi-Luc-GFP cells at Day −7 and treated at Day 0 with UCART22 (intravenous injection, 2 doses: 3×106 and 10×106 UCART22 cells/mouse, 5 mice/group) or left untreated (vehicle injection). Non-transduced T-cells double KO for TRAC and CD52 (NTD DKO) were injected as a control. The UCART22 doses administered were determined according to the doses of CAR+ T-cells used in the literature to demonstrate anti-tumor activity in vivo of other CD22CAR T-cells (Haso et al., 2013). UCART22 treatment resulted in the elimination of the tumor cells, as shown by in vivo imaging, and extended survival, with all the treated mice alive at the end of study (80 days post-UCART22 treatment). Those results demonstrated the anti-tumor activity of UCART22.

CD52− cells are resistant to alemtuzumab in vivo and CD52− CAR+ T-cells show activity in vivo in presence of alemtuzumab.

Studies performed during the development of UCART19, another UCART product containing the same TRAC/CD52 double knock-out, demonstrated that CD52− T-cells are resistant to alemtuzumab in vivo (Poirot et al., 2015).

In addition, the activity of UCART19 cells in presence of alemtuzumab was demonstrated in a tumor xenograft model in NSG mice. All mice receiving tumor cells but no UCART19 cells showed tumor progression leading to their sacrifice by 13 days post-injection. In 5 out of 7 mice receiving tumor and UCART19 cells, the tumor was completely controlled at day 13 and in the remaining two mice, partial responses were observed. In contrast, alemtuzumab treatment was observed to only delay progression of the tumor without UCART19 cell infusion (6/6 mice). In mice treated with alemtuzumab combined with UCART19 cells, the tumor cells were eliminated from the bone marrow, as assessed by luminometry or flow cytometry of cell suspensions obtained from bone marrow isolated at 13 days post-injection.

In conclusion, the mice that received alemtuzumab therapy 2 days before infusion of UCART19 cells, demonstrate anti-tumor efficacy of the UCART19 cells in the presence of alemtuzumab in vivo. In addition, spleen engraftment data at Day 13 show that CD52− T-cells are resistant to alemtuzumab in vivo.

Demonstration of Effective Rituximab-Induced Depletion of RQR8+ Cells In Vivo

The susceptibility of RQR8+ UCART22 to RTX depletion has been previously shown in vitro. Moreover, Martin Pule's group has shown that RTX was able to eliminate RQR8+ cells in an immunocompetent mouse model using a re-engineered RTX to a mouse IgG2a, the functional equivalent of human IgG1 (mRtx-IgG2a) (Philip et al., 2014). This antibody has been adapted for use in murine systems by transfer of the binding portions of RTX to a murine Fc allowing binding to murine Fc receptors with an affinity approximating that with which RTX binds to human Fc receptors. The study was performed using an immunocompetent haploidentical adoptive transfer model with RQR8 transduced C57BL/6 splenocytes transferred to non-lethally irradiated C57BL/6 x BALB/c cross (F1) recipients. This model allows good engraftment levels in all lymphoid tissue sustained by allogeneic stimulation, but also preserves endogenous lymphocytes.

At Day 1, 1.5×106 RQR8+ donor splenocytes from C57BL/6 mice (splenocytes transduced using a retrovirus encoding a RQR8-2A-GD2CAR construct and purified using Miltenyi CD34 beads) were intravenously injected into F1 mice (C57BL/6×BALB/c), 4 hours after a 5Gy X-ray irradiation pre-conditioning. On Day 7, the engraftment of donor cells has been confirmed by flow cytometry in the peripheral blood. Mice were treated three times with murinized RTX (ritux-mIgG2a 150 μg, intravenously injected by tail vein, at Day 7, Day 10 and Day 12) or PBS (untreated). Each cohort had 5 mice. Animals were sacrificed at Day 14 for flow cytometry analysis of the spleen, the bone marrow, the blood and the lymph nodes. In the RTX-treated mice, 50, 60 and 70% depletion of RQR8+ cells were observed in spleen, bone-marrow and blood respectively within 6 hours post ritux-mIgG2a therapy of the mice.

The same study was also performed with the anti-CD19 CAR used in the UCART19 product. UCART19 is also an allogeneic engineered CAR T-cells product containing the same RQR8 construct as UCART22.

Redosing

This study assessed anti-tumor activity of single or multiple injections of UCART22. A B-ALL tumor cell line expressing CD22 (Daudi expressing high level of CD22). Cells were transduced with a lentiviral vector in order to express the GFP and the firefly luciferase.

Tumor cells (0.5×106 Daudi-Luc-GFP) have been intravenously injected on Day −7 to NSG mice (NOD.Cg-Prkdcscid Il2rgtm1Wj1/SzJ, strain 005557, The Jackson Laboratory) via the tail vein. At Day 0, mice were randomized according to the bioluminescence signal measured at Day −1 and body weight into 11 groups of 6 mice.

1, 2 or 3 treatments of UCART22 (at 1 or 3 million of CAR+ cells/mouse) were administered. UCART22 was intravenously injected to mice on Day 0+/−Day 10+/−Day 20. Anti-tumor activity of UCART22 was evaluated by the tumor burden followed by bioluminescence imaging on Day −1, Day 7, Day 14, Day 21, Day 28 and Day 35, observation of the clinical signs and survival of the mice.

Daudi Model, Treatment at 1×106 UCART22 Cells/Mouse

Mice treated 2 or 3 times with 1×106 UCART22 show a better control of the tumor progression and longer survival compared to mice treated once with 1×106 UCART22 (80% survival at day 60 for 3 doses over 0% for one dose).

In one experiment UCART19 was intravenously injected to mice on Day 30. In these mice still alive, the level of cancer cells was below detection at day 90.

Summaries

The activity of UCART22 was demonstrated in vitro and in vivo against B-ALL cell lines and in vitro against primary B-ALL samples.

UCART22 are allogeneic T-cells and thus should be eliminated upon recovery of patients' immune system. In addition, UCART22 are engineered to co-express RQR8, a short membrane protein that provides two epitopes that bind to the monoclonal antibody rituximab. RQR8 provides therefore a means to deplete RQR8+ UCART22 by administration of rituximab in the event of a non-manageable UCART22-related toxicity such as Cytokine Release Syndrome (CRS) or GvHD or prior to allo-HSCT. The effectiveness of rituximab to eliminate RQR8+ cells in vitro was demonstrated using CDC and ADCC assays. Furthermore, the efficiency of the rituximab-induced depletion of RQR8+ cells was demonstrated in vivo in blood, spleen, bone marrow and lymph nodes using an immune-competent mouse model and a murinized version of the rituximab.

Similar results were obtained using R2 or QR3 anti-CD22 CAR expressed in TCR-deficient MHC CI-deficient T cells.

The resistance to alemtuzumab of CD52− cells was demonstrated in vitro and in vivo allowing the potential use of alemtuzumab in the lymphodepleting regimen.

Lastly, resistance to CD8+ T-cell-mediated destruction was observed using R2-anti-CD22 CAR expressed in TCR-deficient MHC CI-deficient T cells.

Additional studies performed to evaluate various risks are summarized in Table 23 below.

TABLE 23

List of in vitro toxicology studies performed.

| Study | Test item | Method | GLP/GMP study | Results |
|---|---|---|---|---|
| TALEN ® persistence | T-cells transfected with mRNA encoding TRAC and CD52 or B2M TALEN ® (GMP mRNA) | Western blot | No | Experiments examining the persistence of TALEN ® proteins within primary human T-cells have shown that high levels of TALEN ® proteins are detected only within the first 24 h post electroporation. |
| Off-target cleavage induced by TALEN ® | T-cells transfected with B2M, TRAC CD52 TALEN ® alone or combined | Guide Sequencing | No | GUIDE sequencing was performed to identify potential off-target sites by an unbiased genome wide analysis. |
|  | UCART22 | High throughput sequencing | No | High throughput sequencing of TRAC and CD52 TALEN ®-treated human T-cells confirmed an extremely low frequency (2.1-3.9 × 10−3) of modifications at three of the putative off-target sites identified by the GUIDE-seq method. |
|  | UCART22 |  | GMP | The level of modifications at the three confirmed off-target sites will be evaluated on all the GMP batches. |
| Genetic stability | UCART22 | Karyotype/ FISH analysis | No | Karyotyping and FISH analysis have been performed on development batches of UCART22 to evaluate the frequency of translocations. |
|  | UCART22 |  | GMP | Karyotyping will be performed in GMP on all the GMP batches as a release criterion. FISH analysis will be performed if translocations are detected by karyotyping. |
|  | UCART22 | IL-2 independent proliferation assay | No | No IL-2 independent proliferation after 18 days in culture was observed in development batches of UCART22 evaluated. |

TABLE 23-continued

List of in vitro toxicology studies performed.

| Study | Test item | Method | GLP/GMP study | Results |
|---|---|---|---|---|
| | UCART22 | | GMP | The IL2-independent proliferation release test aiming to detect any clonal advantage triggered by genes modifications will be performed on all the GMP batches as a release criterion. |
| | UCART22 | qPCR | GMP | Vector copy number will be measured in all the GMP batches. |
| Tissue cross-reactivity assay | Fusion peptide scFv-CD22(m971)-CD8-mFc: m971scFv-CD8 hinge-mouse IgG1 Fc fragment | Immuno-histo-chemical analysis against a panel of human tissues | GLP | In the human tissue panel, specific, plasma membrane scFv-CD22(971)-CD8-mFc binding was observed in lymphoid follicle compartments of lymphoid organs and within lymphoid mucosal aggregates/infiltrates of several other tissues. Based on morphology and distribution, the targeted cells were generally consistent with B lymphocytes. There was no significant unexpected off-target binding of scFv-CD22(971)-CD8-mFc in human tissues. |
| Retrogenix | | Cell microarray technology | No | The binding specificity of the scFv-CD22(m971)-CD8-mFc fusion protein is under evaluation using the Retrogenix platform. |

TABLE 24

List of in vivo toxicology studies.

| Study | Test item | Animal model | GLP study | Results |
|---|---|---|---|---|
| Potential GvHD | UCART22 and Previous UCART products (UCART19 and UCART123) or unmodified T-cells (NTD) in control | NSG mice irradiated at 2 Gy, 1 day before T-cells injection | GLP-like | All mice injected with TCRαβ-positive unmodified T-cells showed treatment-related changes considered probably suggestive of GvHD (weight loss and histopathological changes) with dose-relationship in severity and time of onset. But, UCART products did not elicit any sign of GvHD in the selected model and during a follow-up period of up to 80 days. |

The potential risk of GvHD, was assessed in immunodeficient mice during the development of previous UCART products. This animal model allows the efficient engraftment of human T-cells and has been previously shown to consistently develop xenogeneic GvHD following injection of human PBMCs or T-cells (Ali et al., 2012; Schroeder and DiPersio, 2011).

Off Target Activity of the CD22 CAR

The CD22 specificity of the CD22CAR was evaluated through a GLP-compliant tissue cross-reactivity study showing no significant unexpected off-target binding of the scFv component of the CD22CAR with human tissues and a RETROGENIX® screen is ongoing. Moreover, published clinical data on patient treated with m971 derived CAR T-cells showed no off-target toxicity (Fry et al., 2017).

As CD22 is expressed on normal B-cells, a risk of B-cell aplasia, resulting from on-target/off-tumor activity of UCART22, is anticipated as long as UCART22 will persist.

GVHD of the UCART22

An essential safety feature of UCART22 product is whether the potential of the UCART22 to mediate a GvH reaction has been abrogated by disruption of the TRAC gene and purification of TCRαβ– cells. This risk was assessed during the development of previous UCART products (UCART19 and UCART123) in in vivo preclinical studies. GvHD signs were observed in all NSG mice injected with unmodified T-cells with more severe findings at the highest dose, but no treatment related changes were observed in mice injected with UCART. In clinic, so far, among the fourteen patients treated with UCART19, four of them developed a skin GvHD which was mild to moderate (3 Grade 1 and 1 Grade 2 (Qasim et al., 2017) and data presented at ASH meeting 2017 by R. Benjamin et W. Qasim) and manageable without systemic treatment.

CRS

Other potential safety risks associated with administration of immunotherapy products and with underlying treated disease have been identified: infusion related reaction, cytokine release syndrome (CRS), tumor lysis syndrome, infections and neurotoxicity. CRS is a frequent adverse event in immunotherapy and especially in CAR T-cells trials. In autologous anti-CD19 CAR T-cells clinical trials, the intensity of the cytokine release observed was a result of a combination of several parameters such as the dose of CAR T-cells injected, the signaling domains of the CARs (4-1BB/CD28), the level of proliferation of the CAR T-cells and the tumor burden of the patient at the day of administration. These risks are evaluated in vivo in a model closed to that recently published (Taraseviciute, A., Kean, L., & Jensen, M. C. (2016). Creation of the First Non-Human Primate Model That Faithfully Recapitulates Chimeric Antigen Receptor (CAR) T Cell-Mediated Cytokine Release Syndrome (CRS) and Neurologic Toxicity Following B Cell-Directed CAR-T Cell Therapy. Blood, 128(22), 651. Accessed Mar. 28, 2018. Retrieved from bloodjournal.org/content/128/22/651).

Starting Dose Recommendation for FIH Studies

The standard methods for clinical dose determination are not transposable for CAR T-cell-based immunotherapy, due to the limited relevance of animal model(s), the biodynamic nature of the product and the immune-adoptive mechanism of action.

Therefore, the choice of the starting clinical dose has been mainly based on (i) previous experience gained with CAR T-cells administered in humans (literature on autologous CAR T-cells); (ii) the compassionate cases and patients treated in the ongoing clinical studies with UCART19 at University College London (UCL) and King's College London (KCL) (refer to (Qasim et al., 2017) and the presentations by R. Benjamin and W. Qasim at the ASH meeting 2017) and (iii) the doses currently investigated or approved in other B-ALL autologous CAR studies. The approach is described in the clinical section.

The first results of clinical studies show a huge debulking of tumoral mass in both assays, (>80%) in patients treated with UCART22. Further, the data are demonstrating that even short but efficient treatment (from two dozes) can interrupt and free from malignant B cell, (73% remission at 150 days) especially after redosing and/or use of UCART22 and 19.

```
                              SEQUENCE LISTING

Sequence total quantity: 69
SEQ ID NO: 1            moltype = AA  length = 21
FEATURE                 Location/Qualifiers
REGION                  1..21
                        note = misc_feature - CD8alpha signal peptide
source                  1..21
                        mol_type = protein
                        organism = Homo sapiens
SEQUENCE: 1
MALPVTALLL PLALLLHAAR P                                                   21

SEQ ID NO: 2            moltype = AA  length = 20
FEATURE                 Location/Qualifiers
REGION                  1..20
                        note = misc_feature - signal peptide
source                  1..20
                        mol_type = protein
                        organism = Homo sapiens
SEQUENCE: 2
METDTLLLWV LLLWVPGSTG                                                     20

SEQ ID NO: 3            moltype = AA  length = 16
FEATURE                 Location/Qualifiers
REGION                  1..16
                        note = misc_feature - FcgRIIIa hinge
source                  1..16
                        mol_type = protein
                        organism = Homo sapiens
SEQUENCE: 3
GLAVSTISSF FPPGYQ                                                         16

SEQ ID NO: 4            moltype = AA  length = 45
FEATURE                 Location/Qualifiers
REGION                  1..45
                        note = misc_feature - CD8alpha hinge
source                  1..45
                        mol_type = protein
                        organism = Homo sapiens
SEQUENCE: 4
TTTPAPRPPT PAPTIASQPL SLRPEACRPA AGGAVHTRGL DFACD                         45

SEQ ID NO: 5            moltype = AA  length = 231
FEATURE                 Location/Qualifiers
REGION                  1..231
                        note = misc_feature - IgG1 hinge
source                  1..231
                        mol_type = protein
                        organism = Homo sapiens
SEQUENCE: 5
EPKSPDKTHT CPPCPAPPVA GPSVFLFPPK PKDTLMIART PEVTCVVVDV SHEDPEVKFN   60
WYVDGVEVHN AKTKPREEQY NSTYRVVSVL TVLHQDWLNG KEYKCKVSNK ALPAPIEKTI  120
SKAKGQPREP QVYTLPPSRD ELTKNQVSLT CLVKGFYPSD IAVEWESNGQ PENNYKTTPP  180
VLDSDGSFFL YSKLTVDKSR WQQGNVFSCS VMHEALHNHY TQKSLSLSPG K           231
```

```
SEQ ID NO: 6              moltype = AA  length = 24
FEATURE                   Location/Qualifiers
source                    1..24
                          mol_type = protein
                          organism = Homo sapiens
SEQUENCE: 6
IYIWAPLAGT CGVLLLSLVI TLYC                                           24

SEQ ID NO: 7              moltype = AA  length = 27
FEATURE                   Location/Qualifiers
REGION                    1..27
                          note = misc_feature - 41BB transmembrane domain
source                    1..27
                          mol_type = protein
                          organism = Homo sapiens
SEQUENCE: 7
IISFFLALTS TALLFLLFFL TLRFSVV                                        27

SEQ ID NO: 8              moltype = AA  length = 42
FEATURE                   Location/Qualifiers
REGION                    1..42
                          note = misc_feature - Fragment of 4-1BB (residues 214-255)
source                    1..42
                          mol_type = protein
                          organism = Homo sapiens
SEQUENCE: 8
KRGRKKLLYI FKQPFMRPVQ TTQEEDGCSC RFPEEEEGGC EL                       42

SEQ ID NO: 9              moltype = AA  length = 112
FEATURE                   Location/Qualifiers
REGION                    1..112
                          note = misc_feature - fragment of T-cell surface
                            glycoprotein CD3 zeta chain
source                    1..112
                          mol_type = protein
                          organism = Homo sapiens
SEQUENCE: 9
RVKFSRSADA PAYQQGQNQL YNELNLGRRE EYDVLDKRRG RDPEMGGKPR RKNPQEGLYN     60
ELQKDKMAEA YSEIGMKGER RRGKGHDGLY QGLSTATKDT YDALHMQALP PR            112

SEQ ID NO: 10             moltype = AA  length = 15
FEATURE                   Location/Qualifiers
REGION                    1..15
                          note = G4Sx3 linker sequence
source                    1..15
                          mol_type = protein
                          organism = synthetic construct
SEQUENCE: 10
GGGGSGGGGS GGGGS                                                     15

SEQ ID NO: 11             moltype = DNA  length = 1532
FEATURE                   Location/Qualifiers
misc_feature              1..1532
                          note = UCART22
source                    1..1532
                          mol_type = other DNA
                          organism = synthetic construct
SEQUENCE: 11
tgatcctctt gtcccacaga tatccagaac cctgaccctg ccgtgtacca gctgagagaa     60
tggctctgcc cgtcaccgct ctgctgctgc cactggccct gctgctgcac gcagcaagac    120
cacaggtgca gctgcagcag agcggccctg gctggtgaa gccaagccag acactgtccc    180
tgacctgcgc catcagcggc gattccgtga gctccaactc cgccgcctgg aattggatca    240
ggcagtcccc ttctcggggc ctggagtggc tgggaaggac atactatcgg tctaagtggt    300
acaacgatta tgccgtgtct gtgaagagca gaatcacaat caaccctgac acctccaaga    360
atcagttctc tctgcagctg aatagcgtga caccagagga caccgccgtg tactattgcg    420
ccagggaggt gaccggcgac ctggaggatg cctttgacat ctggggccag ggcacaatgg    480
tgaccgtgtc tagcggagga ggaggatccg gaggaggagg atctggcggc ggcggcagcg    540
atatccagat gacacagtcc ccatcctctc tgagcgcctc cgtgggcgac agagtgacaa    600
tcacctgtag ggcctcccag accatctggt cttacctgaa ctggtatcag cagaggcccg    660
gcaaggcccc taatctgctg atctacgcag caagctccct gcagagcgga gtgccatcca    720
gattctctgg caggggctcc ggcacagact tcaccctgac catctctagc ctgcaggccg    780
aggacttcgc cacctactat tgccagcagt cttatagcat ccccagaca tttggccagg    840
gcaccaagct ggagatcaag accacaaccc cagccaccta cctgccaccaa                900
ccatcgcctc tcagccctg agcctgagac tgaggcatg taggccagca gcaggaggag       960
cagtccatac aagggggctg gattttgcat gcgacatcta catctgggca cctctggcag    1020
gaacatgtgt cgtgctcctg ctcagcctgg tcatcaccct gtactgcaag agaggcagga    1080
agaagctgct gtatatcttc aagcagccct tcatgcgccc cgtgcagaca acccaggagg    1140
aggatggctc ctcctgtagg ttcccagaag aggaggaggg aggatgtgag ctgcgcgtga    1200
```

-continued

```
agttttcccg gtctgccgac gcacctgcat accagcaggg ccagaaccag ctgtataacg 1260
agctgaatct gggccggaga gaggagtacg atgtgctgga caagaggcgc ggcagagatc 1320
cagagatggg cggcaagccc cggagaaaga acccctcagga gggcctgtac aatgagctgc 1380
agaaggataa gatggccgag gcctattctg agatcggcat gaaggagag aggcgccggg 1440
gcaagggaca cgcggactg taccaggac tgagcacagc caccaaggat acctatgacg 1500
ccctgcatat gcaggcactg cctccaaggt ga                               1532

SEQ ID NO: 12              moltype = AA  length = 124
FEATURE                    Location/Qualifiers
REGION                     1..124
                           note = 971- heavy chain
source                     1..124
                           mol_type = protein
                           organism = synthetic construct
SEQUENCE: 12
QVQLQQSGPG LVKPSQTLSL TCAISGDSVS SNSAAWNWIR QSPSRGLEWL GRTYYRSKWY  60
NDYAVSVKSR ITINPDTSKN QFSLQLNSVT PEDTAVYYCA REVTGDLEDA FDIWGQGTMV 120
TVSS                                                              124

SEQ ID NO: 13              moltype = AA  length = 107
FEATURE                    Location/Qualifiers
REGION                     1..107
                           note = 971- light chain
source                     1..107
                           mol_type = protein
                           organism = synthetic construct
SEQUENCE: 13
DIQMTQSPSS LSASVGDRVT ITCRASQTIW SYLNWYQQRP GKAPNLLIYA ASSLQSGVPS  60
RFSGRGSGTD FTLTISSLQA EDFATYYCQQ SYSIPQTFGQ GTKLEIK               107

SEQ ID NO: 14              moltype = AA  length = 461
FEATURE                    Location/Qualifiers
REGION                     1..461
                           note = 971-v1 polypeptide CAR sequence
source                     1..461
                           mol_type = protein
                           organism = synthetic construct
SEQUENCE: 14
MALPVTALLL PLALLLHAAR PQVQLQQSGP GLVKPSQTLS LTCAISGDSV SSNSAAWNWI  60
RQSPSRGLEW LGRTYYRSKW YNDYAVSVKS RITINPDTSK NQFSLQLNSV TPEDTAVYYC 120
AREVTGDLED AFDIWGQGTM VTVSSGGGGS GGGGSGGGGS DIQMTQSPSS LSASVGDRVT 180
ITCRASQTIW SYLNWYQQRP GKAPNLLIYA ASSLQSGVPS RFSGRGSGTD FTLTISSLQA 240
EDFATYYCQQ SYSIPQTFGQ GTKLEIKGLA VSTISSFFPP GYQIYIWAPL AGTCGVLLLS 300
LVITLYCKRG RKKLLYIFKQ PFMRPVQTTQ EEDGCSCRFP EEEEGGCELR VKFSRSADAP 360
AYQQGQNQLY NELNLGRREE YDVLDKRRGR DPEMGGKPRR KNPQEGLYNE LQKDKMAEAY 420
SEIGMKGERR RGKGHDGLYQ GLSTATKDTY DALHMQALPP R                     461

SEQ ID NO: 15              moltype = AA  length = 490
FEATURE                    Location/Qualifiers
REGION                     1..490
                           note = 971-v3 polypeptide CAR sequence
source                     1..490
                           mol_type = protein
                           organism = synthetic construct
SEQUENCE: 15
MALPVTALLL PLALLLHAAR PQVQLQQSGP GLVKPSQTLS LTCAISGDSV SSNSAAWNWI  60
RQSPSRGLEW LGRTYYRSKW YNDYAVSVKS RITINPDTSK NQFSLQLNSV TPEDTAVYYC 120
AREVTGDLED AFDIWGQGTM VTVSSGGGGS GGGGSGGGGS DIQMTQSPSS LSASVGDRVT 180
ITCRASQTIW SYLNWYQQRP GKAPNLLIYA ASSLQSGVPS RFSGRGSGTD FTLTISSLQA 240
EDFATYYCQQ SYSIPQTFGQ GTKLEIKTTT PAPRPPTPAP TIASQPLSLR PEACRPAAGG 300
AVHTRGLDFA CDIYIWAPLA GTCGVLLLSL VITLYCKRGR KKLLYIFKQP FMRPVQTTQE 360
EDGCSCRFPE EEEGGCELRV KFSRSADAPA YQQGQNQLYN ELNLGRREEY DVLDKRRGRD 420
PEMGGKPRRK NPQEGLYNEL QKDKMAEAYS EIGMKGERRR GKGHDGLYQG LSTATKDTYD 480
ALHMQALPPR                                                        490

SEQ ID NO: 16              moltype = AA  length = 530
FEATURE                    Location/Qualifiers
REGION                     1..530
                           note = TAL binding domainTRAC_T01-L
source                     1..530
                           mol_type = protein
                           organism = synthetic construct
SEQUENCE: 16
LTPQQVVAIA SNGGGKQALE TVQRLLPVLC QAHGLTPQQV VAIASNNGGK QALETVQRLL  60
PVLCQAHGLT PQQVVAIASN GGGKQALETV QRLLPVLCQA HGLTPEQVVA IASHDGGKQA 120
LETVQRLLPV LCQAHGLTPE QVVAIASHDG GKQALETVQR LLPVLCQAHG LTPEQVVAIA 180
SHDGGKQALE TVQRLLPVLC QAHGLTPEQV VAIASNIGGK QALETVQALL PVLCQAHGLT 240
PEQVVAIASH DGGKQALETV QRLLPVLCQA HGLTPEQVVA IASNIGGKQA LETVQALLPV 300
LCQAHGLTPQ QVVAIASNNG GKQALETVQR LLPVLCQAHG LTPEQVVAIA SNIGGKQALE 360
```

```
TVQALLPVLC QAHGLTPQQV VAIASNGGGK QALETVQRLL PVLCQAHGLT PEQVVAIASN    420
IGGKQALETV QALLPVLCQA HGLTPQQVVA IASNGGGKQA LETVQRLLPV LCQAHGLTPE    480
QVVAIASHDG GKQALETVQR LLPVLCQAHG LTPQQVVAIA SNGGGRPALE               530

SEQ ID NO: 17           moltype = AA   length = 530
FEATURE                 Location/Qualifiers
REGION                  1..530
                        note = TAL binding domain TRAC_T01-R
source                  1..530
                        mol_type = protein
                        organism = synthetic construct
SEQUENCE: 17
LTPEQVVAIA SHDGGKQALE TVQRLLPVLC QAHGLTPQQV VAIASNGGGK QALETVQRLL     60
PVLCQAHGLT PEQVVAIASH DGGKQALETV QRLLPVLCQA HGLTPEQVVA IASNIGGKQA    120
LETVQALLPV LCQAHGLTPQ QVVAIASNNG GKQALETVQR LLPVLCQAHG LTPEQVVAIA    180
SHDGGKQALE TVQRLLPVLC QAHGLTPQQV VAIASNGGGK QALETVQRLL PVLCQAHGLT    240
PQQVVAIASN NGGKQALETV QRLLPVLCQA HGLTPQQVVA IASNNGGKQA LETVQRLLPV    300
LCQAHGLTPQ QVVAIASNGG GKQALETVQR LLPVLCQAHG LTPEQVVAIA SNIGGKQALE    360
TVQALLPVLC QAHGLTPEQV VAIASHDGGK QALETVQRLL PVLCQAHGLT PEQVVAIASN    420
IGGKQALETV QALLPVLCQA HGLTPEQVVA IASHDGGKQA LETVQRLLPV LCQAHGLTPQ    480
QVVAIASNNG GKQALETVQR LLPVLCQAHG LTPQQVVAIA SNGGGRPALE               530

SEQ ID NO: 18           moltype = DNA   length = 49
FEATURE                 Location/Qualifiers
misc_feature            1..49
                        note = target TALEN TRAC_T01
source                  1..49
                        mol_type = other DNA
                        organism = synthetic construct
SEQUENCE: 18
ttgtcccaca gatatccaga accctgaccc tgccgtgtac cagctgaga                 49

SEQ ID NO: 19           moltype = AA   length = 9
FEATURE                 Location/Qualifiers
REGION                  1..9
                        note = Mimotope of CD20 antigen
source                  1..9
                        mol_type = protein
                        organism = synthetic construct
SEQUENCE: 19
CPYSNPSLC                                                              9

SEQ ID NO: 20           moltype = DNA   length = 1473
FEATURE                 Location/Qualifiers
misc_feature            1..1473
                        note = CAR 11 dis 16
source                  1..1473
                        mol_type = other DNA
                        organism = synthetic construct
SEQUENCE: 20
atggctctgc ccgtcaccgc tctgctgctg ccactggccc tgctgctgca cgcagcaaga     60
ccacaggtgc agctgcagca gagcggccct ggcctggtga agccaagcca gacactgtcc    120
ctgacctgcg ccatcagcgg cgattccgtg agctccaact ccgccgcctg gaattggatc    180
aggcagtccc cttctcgggg cctggagtgg ctgggaagga catactatcg gtctaagtgg    240
tacaacgatt atgccgtgtc tgtgaagagc agaatcacaa tcaaccctga cacctccaac    300
aatcagttct ctctgcagct gaatagcgtg acaccagagg acaccgccgt gtactattgc    360
gccagggagg tgaccggcga cctggaggat gcctttgaca tctggggcca gggcacaatg    420
gtgaccgtgt ctagcggagg aggaggatcc ggaggaggag gatctggcgg cggcggcagc    480
gatatccaga tgacacagtc cccatcctct ctgagcgcct ccgtgggcga cagagtgaca    540
atcacctgta gggcctccca gaccatctgg tcttacctga actggtatca gcagaagccc    600
ggcaaggccc ctaatctgct gatctacgca gcaagctccc tgcagagcgg agtgccatcc    660
agattctctg gcaggggctc cggcacagac ttcaccctga ccatctctag cctgcaggcc    720
gaggacttcg ccacctacta ttgccagcag tcttatagca tccccagac atttggccag    780
ggcaccaagc tggagatcaa gaccacaacc ccagcaccaa ggccacctac acctgcacca    840
accatcgcct ctcagcccct gagcctgaga cctgaggcat gtaggccagc agcaggagga    900
gcagtccata caagggtgtct ggattttgca tgcgacatct acatctgggc acctctggca    960
ggaacatgtg gcgtgctcct gctcagcctg gtcatcaccc tgtactgcaa gagaggcagg   1020
aagaagctgc tgtatatctt caagcagccc ttcatgcgcc ccgtgcagac aacccaggag   1080
gaggatggct gctcctgtag gttcccagaa gaggaggagg aggatgtga gctgcgcgtg   1140
aagttttccc ggtctgccga cgcacctgca taccagcagg ccagaacca gctgtataac   1200
gagctgaatc tgggccggag agaggagtac gatgtgctgg acaagaggcg cggcagagat   1260
ccagagatgg cggcaagcc ccggagaaag aaccctcagg agggcctgta caatgagctg   1320
cagaaggata gatggccga ggcctattct gagatcggca tgaagggaga gaggcgccgg   1380
ggcaaggac acgacggact gtaccaggga ctgagcacag ccaccaagga tacctatgac   1440
gccctgcata tgcaggcact gcctccaagg tga                                1473

SEQ ID NO: 21           moltype = DNA   length = 59
FEATURE                 Location/Qualifiers
misc_feature            1..59
```

```
                    note = TARGET TALEN(R)
source              1..59
                    mol_type = other DNA
                    organism = synthetic construct
SEQUENCE: 21
tgatcctctt gtcccacaga tatccagaac cctgaccctg ccgtgtacca gctgagaga    59

SEQ ID NO: 22       moltype = DNA  length = 1473
FEATURE             Location/Qualifiers
misc_feature        1..1473
                    note = 971-v3 polynucleotide CAR sequence
source              1..1473
                    mol_type = other DNA
                    organism = synthetic construct
SEQUENCE: 22
atggctctgc ccgtcaccgc tctgctgctg ccactggccc tgctgctgca cgcagcaaga    60
ccacaggtgt agctgcagca gagcggccct ggcctggtga agccaagcca gacactgtcc   120
ctgacctgcg ccatcagcgg cgattccgtg agctccaact ccgcgcctg gaattggatc   180
aggcagtccc cttctcgggg cctggagtgg ctgggaagga catactatcg gtctaagtgg   240
tacaacgatt atgccgtgtc tgtgaagagc agaatcacaa tcaaccctga cacctccaag   300
aatcagttct ctctgcagct gaatagcgtg acaccagagg acaccgccgt gtactattgc   360
gccaggagg tgaccggcga cctggaggat gcctttgaca tctggggcca gggcacaatg   420
gtgaccgtgt ctagcggagg aggaggatcc ggaggaggag gatctggcgg cggcggcagc   480
gatatccaga tgacacagtc cccatcctct ctgagcgccc ccgtgggcga cagagtgaca   540
atcacctgta gggcctccca gaccatctgg tcttacctga actggtatca gcagaggccc   600
ggcaaggccc ctaatctgct gatctacgca gcaagctccc tgcagagcgg agtgccatcc   660
agattctctg gcaggggctc cggcacagac ttcaccctga ccatctctag cctgcaggcc   720
gaggacttcg ccacctacta ttgccagcag tcttatagca tccccagac atttggccag   780
ggcaccaagc tggagatcaa gaccacaacc ccagcaccaa ggccacctac acctgcacca   840
accatcgcct ctcagccct gagcctgaga cctgaggcat gtaggccagc agcaggagga   900
gcagtccata caaggggtct ggattttgca tgcgacatct cacatctggc acctctggca   960
ggaacatgtg gcgtgctcct gctcagcctg gtcatcaccc tgtactgcaa gagaggcagg  1020
aagaagctgc tgtatatctt caagcagccc ttcatgcgcc ccgtgcagac aacccaggag  1080
gaggatggct gctcctgtag gttcccagaa gaggaggagg aggatgtgaa gctcgcgtg  1140
aagttttccc ggtctgccga cgcacctgca taccagcagg gccagaacca gctgtataac  1200
gagctgaatc tgggccggag agaggagtac gatgtgctgg acaagaggcg cggcagagat  1260
ccagagatgg gcggcaagcc ccggagaaag aaccctcagg agggcctgta caatgagctg  1320
cagaaggata agatggccga ggcctattct gagatcggca tgaagggaga gaggcgccgg  1380
ggcaagggac acgacggact gtaccagggc ctgagcacag ccaccaagga tacctatgac  1440
gccctgcata tgcaggcact gcctccaagg tga                                 1473

SEQ ID NO: 23       moltype = AA   length = 489
FEATURE             Location/Qualifiers
REGION              1..489
                    note = CAR distal CD22
source              1..489
                    mol_type = protein
                    organism = synthetic construct
SEQUENCE: 23
MALPVTALLL PLALLLHAAR PEVQLVESGG GLVKPGGSLK LSCAASGFAF SIYDMSWVRQ    60
TPEKRLEWVA YISSGGGTLV PDTVKGRFTI SRDNAKNTLY LQMSSLKSED TAMYYCARHS   120
GYGTHWGVLF AYWGQGTLVT VSAGGGGSGG GGSGGGGSDI QMTQTTSSLS ASLGDRVTIS   180
CRASQDISNY LNWYQQKPDG TVKLLIYYTS ILHSGVPSRF SGSGSGTDYS LTISNLEQED   240
FATYFCQQGN TLPWTFGGGT KLEIKATTTP APRPPTPAPT IASQPLSLRP EACRPAAGGA   300
VHTRGLDFAC DIYIWAPLAG TCGVLLLSLV ITLYCKRGRK KLLYIFKQPF MRPVQTTQEE   360
DGCSCRFPEE EEGGCELRVK FSRSADAPAY QQGQNQLYNE LNLGRREEYD VLDKRRGRDP   420
EMGGKPRRKN PQEGLYNELQ KDKMAEAYSE IGMKGERRRG KGHDGLYQGL STATKDTYDA   480
LHMQALPPR                                                            489

SEQ ID NO: 24       moltype = DNA  length = 1470
FEATURE             Location/Qualifiers
misc_feature        1..1470
                    note = CAR distal CD22
source              1..1470
                    mol_type = other DNA
                    organism = synthetic construct
SEQUENCE: 24
atggctctgc ccgtcaccgc tctgctgctg ccactggccc tgctgctgca cgcagcaagg    60
cctgaggtgc agctggtgga atccggagga ggcctggtga agcctggcgg ctctctgaag   120
ctgagctgtg ccgcctccgg cttcgccttt tccatctacg acatgtcttg ggtgaggcag   180
acccagaga agcgcctgga gtgggtggcc tatatcagct ccggcggcgg cacctactat   240
cccgacacag tgaagggccg gttcaccatc tctagagata cgccaagaa tacactgtac   300
ctgcagatgt ctagcctgaa gagcgaggat accgccatgt actattgcgc aaggcactcc   360
ggatacggaa cacactgggg cgtgctgttt gcctattggg gccagggcac cctggtgaca   420
gtgagcgccg gaggaggagg aagcggcgga ggaggctccg gcggcggcgg ctctgacatc   480
cagatgaccc agaccacatc ctctctgagc gcctccctgg gcgacagggt gacaatctct   540
tgtagagcca gcaggatat ctccaactac ctgaattggt atcagcagaa gcctgatggc   600
accgtgaagc tgctgatcta ctatacatct atcctgcaca gcggagtgcc atcccggttc   660
tctggaagcg gatccggaac cgactactct ctgacaatca gcaacctgga gcaggaggat   720
```

```
ttcgccacct attttttgcca gcagggcaat accctgcctt ggacatttgg cggcggcaca    780
aagctggaga tcaaggccac cacaacccct gcaccaaggc caccaacacc agcacctacc    840
atcgcatctc agcctctgag cctgagacca gaggcatgta ggccagcagc aggaggagca    900
gtgcacacaa ggggactgga ttttgcctgt gatatctaca tctgggcacc tctggcagga    960
acatgtggcg tgctcctgct cagcctggtc atcacctgt actgcaagag aggcaggaag   1020
aagctgctgt atatcttcaa gcagcccttc atgagacccg tgcagacaac ccaggaggag   1080
gacggctgct cctgtaggtt cccagaagag gaggagggag gatgtgagct gcgcgtgaag   1140
ttttcccggt ctgccgatgc acctgcatac cagcagggac agaatcagct gtataacgag   1200
ctgaatctgg gccggagaga ggagtacgac gtgctggata gaggagggg aagggaccca   1260
gagatgggag gcaagcctcg gagaaagaac ccacagaggg gcctgctacaa tgagctgcag   1320
aaggacaaga tggccgaggc ctattctgag atcggcatga agggagagag gcgccggggc   1380
aagggacacg atggcctgta ccagggcctg tccacagcca ccaaggacac ctatgatgcc   1440
ctgcatatgc aggcactgcc tccaaggtga                                    1470

SEQ ID NO: 25                  moltype = AA  length = 495
FEATURE                        Location/Qualifiers
REGION                         1..495
                               note = description of artificial sequence: synthetic
                                polypeptide
REGION                         1..495
                               note = misc_feature - 4G7-CAR version 1
source                         1..495
                               mol_type = protein
                               organism = synthetic construct
SEQUENCE: 25
MALPVTALLL PLALLLHAAR PEVQLQQSGP ELIKPGASVK MSCKASGYTF TSYVMHWVKQ     60
KPGQGLEWIG YINPYNDGTK YNEKFKGKAT LTSDKSSSTA YMELSSLTSE DSAVYYCARG    120
TYYYGSRVFD YWGQGTTLTV SSGGGGSGGG GSGGGGSDIV MTQAAPSIPV TPGESVSISC    180
RSSKSLLNSN GNTYLYWFLQ RPGQSPQLLI YRMSNLASGV PDRFSGSGSG TAFTLRISRV    240
EAEDVGVYYC MQHLEYPFTF GAGTKLELKR ADTTTPAPRP PTPAPTIASQ PLSLRPEACR    300
PAAGGAVHTR GLDFACDIYI WAPLAGTCGV LLLSLVITLY CKRGRKKLLY IFKQPFMRPV    360
QTTQEEDGCS CRFPEEEEGG CELRVKFSRS ADAPAYQQGQ NQLYNELNLG RREEYDVLDK    420
RRGRDPEMGG KPRRKNPQEG LYNELQKDKM AEAYSEIGMK GERRRGKGHD GLYQGLSTAT    480
KDTYDALHMQ ALPPR                                                    495

SEQ ID NO: 26                  moltype = AA  length = 495
FEATURE                        Location/Qualifiers
REGION                         1..495
                               note = description of artificial sequence: synthetic
                                polypeptide
REGION                         1..495
                               note = misc_feature - 4G7-CAR version 2
source                         1..495
                               mol_type = protein
                               organism = synthetic construct
SEQUENCE: 26
METDTLLLWV LLLWVPGSTG EVQLQQSGPE LIKPGASVKM SCKASGYTFT SYVMHWVKQK     60
PGQGLEWIGY INPYNDGTKY NEKFKGKATL TSDKSSSTAY MELSSLTSED SAVYYCARGT    120
YYYGSRVFDY WGQGTTLTVS SGGGGSGGGG SGGGGSDIVM TQAAPSIPVT PGESVSISCR    180
SSKSLLNSNG NTYLYWFLQR PGQSPQLLIY RMSNLASGVP DRFSGSGSGT AFTLRISRVE    240
AEDVGVYYCM QHLEYPFTFG AGTKLELKRS DPTTTPAPRP PTPAPTIASQ PLSLRPEACR    300
PAAGGAVHTR GLDFACDIYI WAPLAGTCGV LLLSLVITLY CKRGRKKLLY IFKQPFMRPV    360
QTTQEEDGCS CRFPEEEEGG CELRVKFSRS ADAPAYQQGQ NQLYNELNLG RREEYDVLDK    420
RRGRDPEMGG KPRRKNPQEG LYNELQKDKM AEAYSEIGMK GERRRGKGHD GLYQGLSTAT    480
KDTYDALHMQ ALPPR                                                    495

SEQ ID NO: 27                  moltype = DNA  length = 16
FEATURE                        Location/Qualifiers
misc_feature                   1..16
                               note = Synthetic
source                         1..16
                               mol_type = other DNA
                               organism = synthetic construct
SEQUENCE: 27
ttgtcccaca gatatc                                                    16

SEQ ID NO: 28                  moltype = DNA  length = 19
FEATURE                        Location/Qualifiers
misc_feature                   1..19
                               note = Synthetic
source                         1..19
                               mol_type = other DNA
                               organism = synthetic construct
SEQUENCE: 28
ttgtcccaca gatatccag                                                 19

SEQ ID NO: 29                  moltype = AA  length = 5
FEATURE                        Location/Qualifiers
REGION                         1..5
```

```
                        note = Synthetic
source                  1..5
                        mol_type = protein
                        organism = synthetic construct
SEQUENCE: 29
GGGGS                                                               5

SEQ ID NO: 30           moltype = AA  length = 24
FEATURE                 Location/Qualifiers
REGION                  1..24
                        note = Synthetic
source                  1..24
                        mol_type = protein
                        organism = synthetic construct
SEQUENCE: 30
NSELLSLIND MPITNDQKKL MSNN                                         24

SEQ ID NO: 31           moltype = AA  length = 12
FEATURE                 Location/Qualifiers
REGION                  1..12
                        note = Synthetic
source                  1..12
                        mol_type = protein
                        organism = synthetic construct
SEQUENCE: 31
CQFDLSTRRL KC                                                      12

SEQ ID NO: 32           moltype = AA  length = 12
FEATURE                 Location/Qualifiers
REGION                  1..12
                        note = Synthetic
source                  1..12
                        mol_type = protein
                        organism = synthetic construct
SEQUENCE: 32
CQYNLSSRAL KC                                                      12

SEQ ID NO: 33           moltype = AA  length = 12
FEATURE                 Location/Qualifiers
REGION                  1..12
                        note = Synthetic
source                  1..12
                        mol_type = protein
                        organism = synthetic construct
SEQUENCE: 33
CVWQRWQKSY VC                                                      12

SEQ ID NO: 34           moltype = AA  length = 12
FEATURE                 Location/Qualifiers
REGION                  1..12
                        note = Synthetic
source                  1..12
                        mol_type = protein
                        organism = synthetic construct
SEQUENCE: 34
CVWQRWQKSY VC                                                      12

SEQ ID NO: 35           moltype = AA  length = 25
FEATURE                 Location/Qualifiers
REGION                  1..25
                        note = Synthetic
source                  1..25
                        mol_type = protein
                        organism = synthetic construct
SEQUENCE: 35
SFVLNWYRMS PSNQTDKLAA FPEDR                                        25

SEQ ID NO: 36           moltype = AA  length = 19
FEATURE                 Location/Qualifiers
REGION                  1..19
                        note = Synthetic
source                  1..19
                        mol_type = protein
                        organism = synthetic construct
SEQUENCE: 36
SGTYLCGAIS LAPKAQIKE                                               19

SEQ ID NO: 37           moltype = AA  length = 24
FEATURE                 Location/Qualifiers
```

```
REGION                    1..24
                          note = Synthetic
source                    1..24
                          mol_type = protein
                          organism = synthetic construct
SEQUENCE: 37
ELPTQGTFSN VSTNVSPAKP TTTA                                           24

SEQ ID NO: 38             moltype = AA  length = 12
FEATURE                   Location/Qualifiers
REGION                    1..12
                          note = Synthetic
source                    1..12
                          mol_type = protein
                          organism = synthetic construct
SEQUENCE: 38
GQNDTSQTSS PS                                                        12

SEQ ID NO: 39             moltype = AA  length = 12
FEATURE                   Location/Qualifiers
REGION                    1..12
                          note = Synthetic
source                    1..12
                          mol_type = protein
                          organism = synthetic construct
SEQUENCE: 39
CMWDRFSRWY KC                                                        12

SEQ ID NO: 40             moltype = AA  length = 15
FEATURE                   Location/Qualifiers
REGION                    1..15
                          note = Synthetic
source                    1..15
                          mol_type = protein
                          organism = synthetic construct
SEQUENCE: 40
GGGGSGGGGS GGGGS                                                     15

SEQ ID NO: 41             moltype = AA  length = 18
FEATURE                   Location/Qualifiers
REGION                    1..18
                          note = Synthetic
source                    1..18
                          mol_type = protein
                          organism = synthetic construct
SEQUENCE: 41
GGSSRSSSSG GGGSGGGG                                                  18

SEQ ID NO: 42             moltype = AA  length = 15
FEATURE                   Location/Qualifiers
REGION                    1..15
                          note = Synthetic
source                    1..15
                          mol_type = protein
                          organism = synthetic construct
SEQUENCE: 42
RGRGRGRGRS RGGGS                                                     15

SEQ ID NO: 43             moltype = AA  length = 4
FEATURE                   Location/Qualifiers
REGION                    1..4
                          note = Synthetic
source                    1..4
                          mol_type = protein
                          organism = synthetic construct
SEQUENCE: 43
SGGS                                                                 4

SEQ ID NO: 44             moltype = AA  length = 5
FEATURE                   Location/Qualifiers
REGION                    1..5
                          note = Synthetic
source                    1..5
                          mol_type = protein
                          organism = synthetic construct
SEQUENCE: 44
SSGGS                                                                5

SEQ ID NO: 45             moltype = AA  length = 4
```

-continued

```
FEATURE              Location/Qualifiers
REGION               1..4
                     note = Synthetic
source               1..4
                     mol_type = protein
                     organism = synthetic construct
SEQUENCE: 45
GGGG                                                                     4

SEQ ID NO: 46        moltype = AA  length = 5
FEATURE              Location/Qualifiers
REGION               1..5
                     note = Synthetic
source               1..5
                     mol_type = protein
                     organism = synthetic construct
SEQUENCE: 46
SGGGG                                                                    5

SEQ ID NO: 47        moltype = AA  length = 6
FEATURE              Location/Qualifiers
REGION               1..6
                     note = Synthetic
source               1..6
                     mol_type = protein
                     organism = synthetic construct
SEQUENCE: 47
SGGGGS                                                                   6

SEQ ID NO: 48        moltype = AA  length = 6
FEATURE              Location/Qualifiers
REGION               1..6
                     note = Synthetic
source               1..6
                     mol_type = protein
                     organism = synthetic construct
SEQUENCE: 48
GGGGGS                                                                   6

SEQ ID NO: 49        moltype = AA  length = 7
FEATURE              Location/Qualifiers
REGION               1..7
                     note = Synthetic
source               1..7
                     mol_type = protein
                     organism = synthetic construct
SEQUENCE: 49
SGGGGGS                                                                  7

SEQ ID NO: 50        moltype = AA  length = 6
FEATURE              Location/Qualifiers
REGION               1..6
                     note = Synthetic
source               1..6
                     mol_type = protein
                     organism = synthetic construct
SEQUENCE: 50
SGGGGG                                                                   6

SEQ ID NO: 51        moltype = AA  length = 7
FEATURE              Location/Qualifiers
REGION               1..7
                     note = Synthetic
source               1..7
                     mol_type = protein
                     organism = synthetic construct
SEQUENCE: 51
GSGGGGS                                                                  7

SEQ ID NO: 52        moltype = AA  length = 8
FEATURE              Location/Qualifiers
REGION               1..8
                     note = Synthetic
source               1..8
                     mol_type = protein
                     organism = synthetic construct
SEQUENCE: 52
GGGGGGGS                                                                 8
```

```
SEQ ID NO: 53          moltype = AA   length = 8
FEATURE                Location/Qualifiers
REGION                 1..8
                       note = Synthetic
source                 1..8
                       mol_type = protein
                       organism = synthetic construct
SEQUENCE: 53
SGGGGGGG                                                                    8

SEQ ID NO: 54          moltype = AA   length = 9
FEATURE                Location/Qualifiers
REGION                 1..9
                       note = Synthetic
source                 1..9
                       mol_type = protein
                       organism = synthetic construct
SEQUENCE: 54
SGGGGGGGS                                                                   9

SEQ ID NO: 55          moltype = AA   length = 11
FEATURE                Location/Qualifiers
REGION                 1..11
                       note = Synthetic
source                 1..11
                       mol_type = protein
                       organism = synthetic construct
SEQUENCE: 55
SGGGGSGGGG S                                                               11

SEQ ID NO: 56          moltype = AA   length = 4
FEATURE                Location/Qualifiers
REGION                 1..4
                       note = Synthetic
source                 1..4
                       mol_type = protein
                       organism = synthetic construct
SEQUENCE: 56
GGGS                                                                        4

SEQ ID NO: 57          moltype = AA   length = 5
FEATURE                Location/Qualifiers
REGION                 1..5
                       note = Synthetic
source                 1..5
                       mol_type = protein
                       organism = synthetic construct
SEQUENCE: 57
GGGGS                                                                       5

SEQ ID NO: 58          moltype = AA   length = 20
FEATURE                Location/Qualifiers
REGION                 1..20
                       note = Synthetic
source                 1..20
                       mol_type = protein
                       organism = synthetic construct
SEQUENCE: 58
GGGGSGGGGS GGGGSGGGGS                                                      20

SEQ ID NO: 59          moltype = AA   length = 15
FEATURE                Location/Qualifiers
REGION                 1..15
                       note = Synthetic
source                 1..15
                       mol_type = protein
                       organism = synthetic construct
SEQUENCE: 59
GGGGSGGGGS GGGGS                                                           15

SEQ ID NO: 60          moltype = AA   length = 157
FEATURE                Location/Qualifiers
REGION                 1..157
                       note = Synthetic
source                 1..157
                       mol_type = protein
                       organism = synthetic construct
SEQUENCE: 60
MGTSLLCWMA LCLLGADHAD ACPYSNPSLC SGGGGSELPT QGTFSNVSTN VSPAKPTTTA          60
```

```
CPYSNPSLCS GGGGSPAPRP PTPAPTIASQ PLSLRPEACR PAAGGAVHTR GLDFACDIYI    120
WAPLAGTCGV LLLSLVITLY CNHRNRRRVC KCPRPVV                             157

SEQ ID NO: 61           moltype = AA  length = 454
FEATURE                 Location/Qualifiers
REGION                  1..454
                        note = Synthetic
source                  1..454
                        mol_type = protein
                        organism = synthetic construct
SEQUENCE: 61
METDTLLLWV LLLWVPGSTG EVQLVQSGGG VVRPGGSLRL PCAASGFTFD DYGMSWVRQA    60
PGKGLEWVSG INWNGGSTGY ADSVKGRFTI SRDNAKNSLY LQMNSLRAED TALYHCARGG    120
DDAFDIWGQG TMVTVSSGGG GSGGGGSGGG GSRIVMTQSP GTLSVSPGET ATLSCRASQS    180
FSNMLAWYQQ KSGQPPRLLI YGVSTRAAGV PARFSGSGSG TEFTLTISNL QSEDFAVYYC    240
QQYGDWPRYT FGQGTKVERK GLAVSTISSF FPPGYQIYIW APLAGTCGVL LLSLVITLYC    300
KRGRKKLLYI FKQPFMRPVQ TTQEEDGCSC RFPEEEEGGC ELRVKFSRSA DAPAYQQGQN    360
QLYNELNLGR REEYDVLDKR RGRDPEMGGK PRRKNPQEGL YNELQKDKMA EAYSEIGMKG    420
ERRRGKGHDG LYQGLSTATK DTYDALHMQA LPPR                                454

SEQ ID NO: 62           moltype = AA  length = 483
FEATURE                 Location/Qualifiers
REGION                  1..483
                        note = Synthetic
source                  1..483
                        mol_type = protein
                        organism = synthetic construct
SEQUENCE: 62
METDTLLLWV LLLWVPGSTG EVQLVQSGGG VVRPGGSLRL PCAASGFTFD DYGMSWVRQA    60
PGKGLEWVSG INWNGGSTGY ADSVKGRFTI SRDNAKNSLY LQMNSLRAED TALYHCARGG    120
DDAFDIWGQG TMVTVSSGGG GSGGGGSGGG GSRIVMTQSP GTLSVSPGET ATLSCRASQS    180
FSNMLAWYQQ KSGQPPRLLI YGVSTRAAGV PARFSGSGSG TEFTLTISNL QSEDFAVYYC    240
QQYGDWPRYT FGQGTKVERK TTTPAPRPPT PAPTIASQPL SLRPEACRPA AGGAVHTRGL    300
DFACDIYIWA PLAGTCGVLL LSLVITLYCK RGRKKLYIF KQPFMRPVQT TQEEDGCSCR    360
FPEEEEGGCE LRVKFSRSAD APAYQQGQNQ LYNELNLGRR EEYDVLDKRR GRDPEMGGKP    420
RRKNPQEGLY NELQKDKMAE AYSEIGMKGE RRRGKGHDGL YQGLSTATKD TYDALHMQAL    480
PPR                                                                  483

SEQ ID NO: 63           moltype = AA  length = 460
FEATURE                 Location/Qualifiers
REGION                  1..460
                        note = Synthetic
source                  1..460
                        mol_type = protein
                        organism = synthetic construct
SEQUENCE: 63
METDTLLLWV LLLWVPGSTG QVQLQQSGPG LVKPSQTLSL TCAISGDSVS SNSAAWNWIR    60
QSPSRGLEWL GRTYYRSKWY NDYAVSVKSR ITINPDTSKN QFSLQLNSVT PEDTAVYYCA    120
REVTGDLEDA FDIWGQGTMV TVSSGGGGSG GGGSGGGGSD IQMTQSPSSL SASVGDRVTI    180
TCRASQTIWS YLNWYQQRPG KAPNLLIYAA SSLQSGVPSR FSGRGSGTDF TLTISSLQAE    240
DFATYYCQQS YSIPQTFGQG TKLEIKGLAV STISSFFPPG YQIYIWAPLA GTCGVLLLSL    300
VITLYCKRGR KKLLYIFKQP FMRPVQTTEE DGCSCRFPE EEEGGCELRV KFSRSADAPA    360
YQQGQNQLYN ELNLGRREEY DVLDKRRGRD PEMGGKPRRK NPQEGLYNEL QKDKMAEAYS    420
EIGMKGERRR GKGHDGLYQG LSTATKDTYD ALHMQALPPR                          460

SEQ ID NO: 64           moltype = AA  length = 489
FEATURE                 Location/Qualifiers
REGION                  1..489
                        note = Synthetic
source                  1..489
                        mol_type = protein
                        organism = synthetic construct
SEQUENCE: 64
METDTLLLWV LLLWVPGSTG QVQLQQSGPG LVKPSQTLSL TCAISGDSVS SNSAAWNWIR    60
QSPSRGLEWL GRTYYRSKWY NDYAVSVKSR ITINPDTSKN QFSLQLNSVT PEDTAVYYCA    120
REVTGDLEDA FDIWGQGTMV TVSSGGGGSG GGGSGGGGSD IQMTQSPSSL SASVGDRVTI    180
TCRASQTIWS YLNWYQQRPG KAPNLLIYAA SSLQSGVPSR FSGRGSGTDF TLTISSLQAE    240
DFATYYCQQS YSIPQTFGQG TKLEIKTTTP APRPPTPAPT IASQPLSLRP EACRPAAGGA    300
VHTRGLDFAC DIYIWAPLAG TCGVLLLSLV ITLYCKRGRK KLLYIFKQPF MRPVQTTQEE    360
DGCSCRFPEE EEGGCELRVK FSRSADAPAY QQGQNQLYNE LNLGRREEYD VLDKRRGRDP    420
EMGGKPRRKN PQEGLYNELQ KDKMAEAYSE IGMKGERRRG KGHDGLYQGL STATKDTYDA    480
LHMQALPPR                                                            489

SEQ ID NO: 65           moltype = AA  length = 469
FEATURE                 Location/Qualifiers
REGION                  1..469
                        note = Synthetic
source                  1..469
                        mol_type = protein
```

```
                        organism = synthetic construct
SEQUENCE: 65
QVQLQQSGPG LVKPSQTLSL TCAISGDSVS SNSAAWNWIR QSPSRGLEWL GRTYYRSKWY    60
NDYAVSVKSR ITINPDTSKN QFSLQLNSVT PEDTAVYYCA REVTGDLEDA FDIWGQGTMV   120
TVSSGGGGSG GGGSGGGGSD IQMTQSPSSL SASVGDRVTI TCRASQTIWS YLNWYQQRPG   180
KAPNLLIYAA SSLQSGVPSR FSGRGSGTDF TLTISSLQAE DFATYYCQQS YSIPQTFGQG   240
TKLEIKTTTP APRPPTPAPT IASQPLSLRP EACRPAAGGA VHTRGLDFAC DIYIWAPLAG   300
TCGVLLLSLV ITLYCKRGRK KLLYIFKQPF MRPVQTTQEE DGCSCRFPEE EEGGCELRVK   360
FSRSADAPAY QQGQNQLYNE LNLGRREEYD VLDKRRGRDP EMGGKPRRKN PQEGLYNELQ   420
KDKMAEAYSE IGMKGERRRG KGHDGLYQGL STATKDTYDA LHMQALPPR              469

SEQ ID NO: 66           moltype = AA   length = 453
FEATURE                 Location/Qualifiers
REGION                  1..453
                        note = Synthetic
source                  1..453
                        mol_type = protein
                        organism = synthetic construct
SEQUENCE: 66
MALPVTALLP LALLLHAARP EVQLVQSGGG VVRPGGSLRL PCAASGFTFD DYGMSWVRQA    60
PGKGLEWVSG INWNGGSTGY ADSVKGRFTI SRDNAKNSLY LQMNSLRAED TALYHCARGG   120
DDAFDIWGQG TMVTVSSGGG SGGGGSGGGG SRIVMTQSPG TLSVSPGETA TLSCRASQSF   180
SNMLAWYQQK SGQPPRLLIY GVSTRAAGVP ARFSGSGSGT EFTLTISNLQ SEDFAVYYCQ   240
QYGDWPRYTF GQGTKVERKG LAVSTISSFF PPGYQIYIWA PLAGTCGVLL LSLVITLYCK   300
RGRKKLLYIF KQPFMRPVQT TQEEDGCSCR FPEEEEGGCE LRVKFSRSAD APAYQQGQNQ   360
LYNELNLGRR EEYDVLDKRR GRDPEMGGKP RRKNPQEGLY NELQKDKMAE AYSEIGMKGE   420
RRRGKGHDGL YQGLSTATKD TYDALHMQAL PPR                               453

SEQ ID NO: 67           moltype = AA   length = 483
FEATURE                 Location/Qualifiers
REGION                  1..483
                        note = Synthetic
source                  1..483
                        mol_type = protein
                        organism = synthetic construct
SEQUENCE: 67
MALPVTALLP LALLLHAARP EVQLVQSGGG VVRPGGSLRL PCAASGFTFD DYGMSWVRQA    60
PGKGLEWVSG INWNGGSTGY ADSVKGRFTI SRDNAKNSLY LQMNSLRAED TALYHCARGG   120
DDAFDIWGQG TMVTVSSGGG GSGGGGSGGG GSRIVMTQSP GTLSVSPGET ATLSCRASQS   180
FSNMLAWYQQ KSGQPPRLLI YGVSTRAAGV PARFSGSGSG TEFTLTISNL QSEDFAVYYC   240
QQYGDWPRYT FGQGTKVERK TTTPAPRPPT PAPTIASQPL SLRPEACRPA AGGAVHTRGL   300
DFACDIYIWA PLAGTCGVLL LSLVITLYCK RGRKKLLYIF KQPFMRPVQT TQEEDGCSCR   360
FPEEEEGGCE LRVKFSRSAD APAYQQGQNQ LYNELNLGRR EEYDVLDKRR GRDPEMGGKP   420
RRKNPQEGLY NELQKDKMAE AYSEIGMKGE RRRGKGHDGL YQGLSTATKD TYDALHMQAL   480
PPR                                                                483

SEQ ID NO: 68           moltype = AA   length = 461
FEATURE                 Location/Qualifiers
REGION                  1..461
                        note = Synthetic
source                  1..461
                        mol_type = protein
                        organism = synthetic construct
SEQUENCE: 68
MALPVTALLL PLALLLHAAR PQVQLQQSGP GLVKPSQTLS LTCAISGDSV SSNSAAWNWI    60
RQSPSRGLEW LGRTYYRSKW YNDYAVSVKS RITINPDTSK NQFSLQLNSV TPEDTAVYYC   120
AREVTGDLED AFDIWGQGTM VTVSSGGGGS GGGGSGGGGS DIQMTQSPSS LSASVGDRVT   180
ITCRASQTIW SYLNWYQQRP GKAPNLLIYA ASSLQSGVPS RFSGRGSGTD FTLTISSLQA   240
EDFATYYCQQ SYSIPQTFGQ GTKLEIKGLA VSTISSFFPP GYQIYIWAPL AGTCGVLLLS   300
LVITLYCKRG RKKLLYIFKQ PFMRPVQTTQ EEDGCSCRFP EEEEGGCELR VKFSRSADAP   360
AYQQGQNQLY NELNLGRREE YDVLDKRRGR DPEMGGKPRR KNPQEGLYNE LQKDKMAEAY   420
SEIGMKGERR RGKGHDGLYQ GLSTATKDTY DALHMQALPP R                      461

SEQ ID NO: 69           moltype = AA   length = 489
FEATURE                 Location/Qualifiers
REGION                  1..489
                        note = Synthetic
source                  1..489
                        mol_type = protein
                        organism = synthetic construct
SEQUENCE: 69
MALPVTALLL PLALLLHAAR PQVQLQQSGP GLVKPSQTLS LTCAISGDSV SSNSAAWNWI    60
RQSPSRGLEW LGRTYYRSKW YNDYAVSVKS RITINPDTSK NQFSLQLNSV TPEDTAVYYC   120
AREVTGDLED AFDIWGQGTM VTVSSGGGGS GGGGSGGGGS DIQMTQSPSS LSASVGDRVT   180
ITCRASQTIW SYLNWYQQRP GKAPNLLIYA ASSLQSGVPS RFSGRGSGTD FTLTISSLQA   240
```

```
EDFATYYCQQ SYSIPQTFGQ GTKLEIKTTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YQQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPP                                                         489
```

What is claimed:

1. An engineered human Universal Chimeric Antigen Receptor (CAR) T Cell specific for CD22 (UCART22) comprising a Chimeric Antigen Receptor specific for CD22 (anti-CD22 CAR) and a safety switch, wherein:
   (a) said anti-CD22 CAR comprises amino acid residues 22-490 of SEQ ID NO: 15, and
   (b) said safety switch comprises a sequence of SEQ ID NO: 60, and wherein the UCART22 comprises an inactivated CD52 gene and an inactivated T cell receptor alpha constant (TRAC) gene.

2. The UCART22 of claim 1, wherein both alleles of the CD52 gene are inactivated.

3. The UCART22 of claim 1, wherein both alleles of the TRAC gene are inactivated.

4. The UCART22 of claim 1, wherein both alleles of the CD52 gene are inactivated and both alleles of the TRAC gene are inactivated.

5. The UCART22 of claim 1, wherein the UCART22 comprises a polynucleotide having a sequence of SEQ ID NO: 11 inserted into its genome and further comprises an inactivated TRAC gene comprising an insertion, deletion, or mutation within the sequence of SEQ ID NO: 18.

6. The UCART22 of claim 5, wherein said polynucleotide having a sequence of SEQ ID NO: 11 is inserted into the TRAC gene within the sequence of SEQ ID NO: 18.

7. The UCART22 of claim 1, wherein the UCART22 exhibits an undetectable level of TCR expression at its cell surface as measured by flow cytometry.

8. The UCART22 of claim 1, wherein the UCART22 exhibits an undetectable level of CD52 expression at its cell surface as measured by flow cytometry.

9. A population of cells comprising the UCART22 of claim 1.

10. A pharmaceutical composition comprising the UCART22 of claim 1 and a pharmaceutically acceptable excipient.

11. A pharmaceutical composition comprising the population of cells of claim 9 and a pharmaceutically acceptable excipient.

12. A method of treating a cancer in a subject in need thereof, comprising administering to the subject an engineered human Universal Chimeric Antigen Receptor (CAR) T Cell specific for CD22 (UCART22) comprising a Chimeric Antigen Receptor specific for CD22 (anti-CD22 CAR) and a safety switch, wherein:
   (a) said anti-CD22 CAR comprises amino acid residues 22-490 of SEQ ID NO: 15, and
   (b) said safety switch comprises a sequence of SEQ ID NO: 60, and wherein the UCART22 comprises an inactivated CD52 gene and an inactivated T cell receptor alpha constant (TRAC) gene.

13. The method of claim 12, wherein both alleles of the CD52 gene are inactivated.

14. The method of claim 12, wherein both alleles of the TRAC gene are inactivated.

15. The method of claim 12, wherein both alleles of the CD52 gene are inactivated and both alleles of the TRAC gene are inactivated.

16. The method of claim 12, wherein the UCART22 comprises a polynucleotide having a sequence of SEQ ID NO: 11 inserted into its genome and further comprises an inactivated TRAC gene comprising an insertion, deletion, or mutation within the sequence of SEQ ID NO: 18.

17. The method of claim 16, wherein said polynucleotide having a sequence of SEQ ID NO: 11 is inserted into the TRAC gene within the sequence of SEQ ID NO: 18.

18. The method of claim 12, wherein the UCART22 exhibits an undetectable level of TCR expression at its cell surface as measured by flow cytometry.

19. The method of claim 12, wherein the UCART22 exhibits an undetectable level of CD52 expression at its cell surface as measured by flow cytometry.

20. The method of claim 12, wherein the cancer is a CD22 expressing hematological cancer selected from lymphoma, Hodgkin lymphoma, non Hodgkin lymphoma, leukemia, multiple myeloma, B-chronic lymphocytic leukemia, hairy cell leukemia, acute lymphocytic leukemia (ALL), Burkitt's lymphoma, acute lymphocytic cancer, and acute myeloid leukemia.

21. The method of claim 12, wherein the cancer is refractory or relapse B-ALL.

22. The method of claim 20, wherein the cancer comprises a relapse refractory CD22-expressing hematological cancer.

23. The method of claim 22, wherein the CD22-expressing hematological cancer comprises an aggressive form of said CD22-related hematological cancer.

24. The method of claim 21, wherein the cancer is a pediatric cancer.

* * * * *